US009492341B2

(12) United States Patent
Huster et al.

(10) Patent No.: US 9,492,341 B2
(45) Date of Patent: Nov. 15, 2016

(54) HOSPITAL BED WITH GRAPHICAL USER INTERFACE HAVING ADVANCED FUNCTIONALITY

(75) Inventors: Keith A. Huster, Sunman, IN (US); Dan R. Tallent, Hope, IN (US); Brian J. Kendall, Batesville, IN (US); William G. Pittenger, Aurora, IN (US); Stephen C. Flint, Fortville, IN (US); Robert M. Zerhusen, Cincinnati, OH (US); Matthew W. Crane, Prospect, KY (US); James M. Allen, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 575 days.

(21) Appl. No.: 13/249,336

(22) Filed: Sep. 30, 2011

(65) Prior Publication Data
US 2012/0089419 A1 Apr. 12, 2012

Related U.S. Application Data

(60) Provisional application No. 61/391,261, filed on Oct. 8, 2010.

(51) Int. Cl.
*G06Q 50/00* (2012.01)
*A61G 7/05* (2006.01)
(Continued)

(52) U.S. Cl.
CPC ........... *A61G 7/0507* (2013.01); *A61B 5/1115* (2013.01); *A61G 7/012* (2013.01); *A61G 7/015* (2013.01); *A61G 7/018* (2013.01); *A61G 7/05776* (2013.01); *G06F 19/322* (2013.01); *G06F 19/3406* (2013.01); *G06Q 50/24* (2013.01); *A61G 2007/0524* (2013.01); *A61G 2007/0527* (2013.01); *A61G 2203/16* (2013.01); *A61G 2203/20* (2013.01); *A61G 2203/42* (2013.01);
(Continued)

(58) Field of Classification Search
CPC ................... G06Q 50/22–50/24; A61G 7/0507
USPC .......................................................... 705/2–3
See application file for complete search history.

(56) References Cited

U.S. PATENT DOCUMENTS 5,181,288 A 1/1993 Heaton et al.
5,403,251 A 4/1995 Belsito et al.
(Continued)

FOREIGN PATENT DOCUMENTS

WO WO 01/86575 A2 11/2001
WO WO 03/014871 A2 2/2003
(Continued)

OTHER PUBLICATIONS

Extended European Search Report for EP 11 18 4041.9, dated Jan. 10, 2014, 13 pages.

*Primary Examiner* — Robert Sorey
(74) *Attorney, Agent, or Firm* — Barnes & Thornburg LLP

(57) ABSTRACT

A patient support apparatus, such as a hospital bed, communicates with an electronic medical record (EMR) system in healthcare facility. The hospital bed includes a patient support structure to support a patient, a graphical user interface coupled to the patient support structure, and control circuitry coupled to the graphical user interface. The graphical user interface displays at least one input that may be used by a caregiver to chart data into an electronic medical record (EMR) of a patient supported by the patient support structure.

31 Claims, 26 Drawing Sheets

(51) Int. Cl.

| | | |
|---|---|---|
| *A61B 5/11* | (2006.01) | |
| *A61G 7/012* | (2006.01) | |
| *A61G 7/015* | (2006.01) | |
| *A61G 7/018* | (2006.01) | |
| *A61G 7/057* | (2006.01) | |
| *G06Q 50/24* | (2012.01) | |
| *G06F 19/00* | (2011.01) | |

(52) U.S. Cl.
CPC ....... *A61G 2205/50* (2013.01); *A61G 2205/60* (2013.01); *G06F 19/3456* (2013.01)

(56) References Cited

U.S. PATENT DOCUMENTS

| | | |
|---|---|---|
| 5,542,138 A | 8/1996 | Williams et al. |
| 5,611,096 A | 3/1997 | Bartlett et al. |
| 5,664,270 A | 9/1997 | Bell et al. |
| 5,713,856 A | 2/1998 | Eggers et al. |
| 5,833,623 A | 11/1998 | Mann et al. |
| 5,859,390 A | 1/1999 | Stafford et al. |
| 6,014,784 A | 1/2000 | Taylor et al. |
| 6,146,523 A | 11/2000 | Kenley et al. |
| 6,279,183 B1 | 8/2001 | Kummer et al. |
| 6,339,410 B1 | 1/2002 | Milner et al. |
| 6,353,950 B1 | 3/2002 | Bartlett et al. |
| 6,371,123 B1 | 4/2002 | Stark et al. |
| 6,384,728 B1 | 5/2002 | Kanor et al. |
| 6,409,662 B1 | 6/2002 | Lloyd et al. |
| 6,487,735 B1 | 12/2002 | Jacques, II et al. |
| 6,493,568 B1 | 12/2002 | Bell et al. |
| 6,536,056 B1 | 3/2003 | Vrzalik et al. |
| 6,566,833 B2 | 5/2003 | Bartlett |
| 6,611,979 B2 | 9/2003 | Welling et al. |
| 6,658,680 B2 | 12/2003 | Osborne et al. |
| 6,680,443 B2 | 1/2004 | Dixon |
| 6,691,346 B2 | 2/2004 | Osborne et al. |
| 6,735,551 B2 | 5/2004 | Voegeli et al. |
| 6,771,181 B1 | 8/2004 | Hughen, Jr. |
| 6,824,052 B2 | 11/2004 | Walsh |
| 6,829,796 B2 | 12/2004 | Salvatini et al. |
| 6,924,441 B1 | 8/2005 | Mobley et al. |
| 6,956,572 B2 | 10/2005 | Zaleski |
| 6,957,461 B2 | 10/2005 | Osborne et al. |
| 7,033,539 B2 | 4/2006 | Krensky et al. |
| 7,038,588 B2 | 5/2006 | Boone et al. |
| 7,076,818 B2 | 7/2006 | Kummer et al. |
| 7,176,391 B2 | 2/2007 | Metz et al. |
| 7,213,009 B2 | 5/2007 | Pestotnik et al. |
| 7,225,408 B2 | 5/2007 | O'Rourke |
| 7,237,287 B2 | 7/2007 | Weismiller et al. |
| 7,253,366 B2 | 8/2007 | Bhai |
| 7,296,312 B2 | 11/2007 | Menkedick et al. |
| 7,319,386 B2 | 1/2008 | Collins, Jr. et al. |
| 7,480,951 B2 | 1/2009 | Weismiller et al. |
| 7,529,685 B2 | 5/2009 | Davies et al. |
| 7,538,659 B2 | 5/2009 | Ulrich et al. |
| 7,594,889 B2 | 9/2009 | St. Ores et al. |
| 7,610,637 B2 | 11/2009 | Menkedick et al. |
| 7,612,679 B1 | 11/2009 | Fackler et al. |
| 7,612,999 B2 | 11/2009 | Clark et al. |
| 7,664,659 B2 | 2/2010 | Lancaster et al. |
| 7,711,579 B2 | 5/2010 | Lancaster et al. |
| 7,737,827 B2 | 6/2010 | Perkins et al. |
| 7,746,218 B2 | 6/2010 | Collins, Jr. et al. |
| 7,769,598 B2 | 8/2010 | Denholm |
| 7,791,866 B2 | 9/2010 | Clark et al. |
| 7,801,740 B1 | 9/2010 | Lesser |
| 7,801,743 B2 | 9/2010 | Graves et al. |
| 7,835,925 B2 | 11/2010 | Roe et al. |
| 7,852,208 B2 | 12/2010 | Collins, Jr. et al. |
| 7,868,740 B2 | 1/2011 | McNeely et al. |
| 7,912,733 B2 | 3/2011 | Clements et al. |
| 7,962,981 B2 | 6/2011 | Lemire et al. |
| 7,966,678 B2 | 6/2011 | Ten Eyck et al. |
| 7,974,924 B2 | 7/2011 | Holla et al. |
| 7,990,691 B2 | 8/2011 | Clark et al. |
| 8,000,977 B2 | 8/2011 | Achan |
| 8,005,686 B2 | 8/2011 | Smith |
| 8,027,849 B2 | 9/2011 | Johnson et al. |
| 8,031,057 B2 | 10/2011 | McNeely et al. |
| 8,082,160 B2 | 12/2011 | Collins, Jr. et al. |
| 2002/0059679 A1 | 5/2002 | Weismiller et al. |
| 2002/0111701 A1 | 8/2002 | Borders |
| 2002/0147390 A1 | 10/2002 | Markis |
| 2003/0052787 A1* | 3/2003 | Zerhusen et al. ......... 340/573.1 |
| 2004/0148055 A1* | 7/2004 | Shoenfeld ................. 700/237 |
| 2004/0227737 A1 | 11/2004 | Novak et al. |
| 2004/0249673 A1* | 12/2004 | Smith ........................ 705/2 |
| 2005/0128184 A1 | 6/2005 | McGreevy |
| 2005/0166324 A1 | 8/2005 | Dixon et al. |
| 2005/0172405 A1 | 8/2005 | Menkedick et al. |
| 2005/0273940 A1 | 12/2005 | Petrosenko et al. |
| 2005/0288571 A1 | 12/2005 | Perkins et al. |
| 2006/0049936 A1* | 3/2006 | Collins et al. ......... 340/539.11 |
| 2006/0101581 A1 | 5/2006 | Blanchard et al. |
| 2006/0103636 A1 | 5/2006 | Parsons |
| 2006/0229557 A1 | 10/2006 | Fathallah et al. |
| 2007/0066866 A1 | 3/2007 | Noguchi et al. |
| 2007/0163045 A1 | 7/2007 | Becker et al. |
| 2007/0164871 A1 | 7/2007 | Dionne et al. |
| 2007/0174964 A1 | 8/2007 | Lemire et al. |
| 2007/0194939 A1* | 8/2007 | Alvarez et al. .......... 340/573.1 |
| 2007/0210917 A1 | 9/2007 | Collins, Jr. et al. |
| 2008/0172789 A1 | 7/2008 | Elliot et al. |
| 2008/0235872 A1 | 10/2008 | Newkirk et al. |
| 2009/0012820 A1* | 1/2009 | Bishop et al. ................ 705/3 |
| 2009/0093688 A1* | 4/2009 | Mathur ........................ 600/300 |
| 2009/0112630 A1* | 4/2009 | Collins et al. ................ 705/3 |
| 2009/0212925 A1 | 8/2009 | Schuman, Sr. et al. |
| 2009/0212926 A1 | 8/2009 | Du et al. |
| 2009/0216556 A1* | 8/2009 | Martin et al. ................ 705/3 |
| 2009/0217080 A1 | 8/2009 | Ferguson et al. |
| 2010/0079276 A1 | 4/2010 | Collins, Jr. et al. |
| 2010/0198622 A1* | 8/2010 | Gajic et al. ................. 705/3 |
| 2010/0212087 A1 | 8/2010 | Leib et al. |
| 2010/0223070 A1 | 9/2010 | Kelly et al. |
| 2010/0228565 A1* | 9/2010 | Rosow et al. ............... 705/2 |
| 2010/0231421 A1 | 9/2010 | Rawls-Meehan |
| 2010/0324380 A1* | 12/2010 | Perkins et al. ............ 600/301 |
| 2011/0144548 A1 | 6/2011 | Elliott et al. |
| 2011/0245630 A1* | 10/2011 | St. Pierre ............. G06F 19/322 600/301 |
| 2011/0277242 A1 | 11/2011 | Dionne et al. |
| 2012/0065994 A1* | 3/2012 | Carter et al. ................ 705/3 |
| 2012/0116803 A1* | 5/2012 | Reid et al. .................. 705/2 |

FOREIGN PATENT DOCUMENTS

| | | |
|---|---|---|
| WO | 2004/021952 | 3/2004 |
| WO | 2007/008830 | 1/2007 |
| WO | 2007/008831 | 1/2007 |
| WO | WO 2007/075701 A2 | 7/2007 |
| WO | WO 2009/065109 A1 | 5/2009 |

\* cited by examiner

HOSPITAL BED WITH GRAPHICAL USER INTERFACE HAVING ADVANCED FUNCTIONALITY

CROSS REFERENCE TO RELATED APPLICATIONS

The present application claims the benefit, under 35 U.S.C. §119(e), of U.S. Provisional Application No. 61/391,261 which was filed Oct. 8, 2010 and which is hereby incorporated by reference herein.

BACKGROUND

The present disclosure relates to patient support apparatuses such as hospital beds. More particularly, the present disclosure relates to patient support apparatuses having graphical user interfaces for viewing data and entering commands.

Patient support apparatus having graphical user interfaces or display screens are known in the art. The graphical user interfaces of hospital beds oftentimes are touch screens that display icons which are used to control functions of the hospital bed or to display information of possible interest to caregivers concerning bed functions and features. See, for example, U.S. Patent Application Publication No. 2008/0235872 A1 which is titled "User Interface for Hospital Bed." See also U.S. Patent Application Publication No. 2008/0172789 A1 which is titled "Patient Support with Improved Control." While sophisticated beds with graphical display screens are known, a need persists in enhancing the connectivity between hospital beds and other computer systems and applications, such as an electronic medical record (EMR) system, in a healthcare facility.

SUMMARY

The present invention comprises one or more of the features recited in the appended claims and/or the following features which, alone or in any combination, may comprise patentable subject matter:

A patient support apparatus, such as a hospital bed, may be provided for use in a healthcare facility which may have an electronic medical record (EMR) system. The hospital bed may include a patient support structure to support a patient, a graphical user interface coupled to the patient support structure, and control circuitry coupled to the graphical user interface. The graphical user interface may display at least one input that may be used by a caregiver to chart data into an electronic medical record (EMR) of a patient supported by the patient support structure.

In some embodiments, the control circuitry may require verification of the caregiver's identity prior to sending data to the EMR system for charting in the patient's EMR. In connection with requiring verification of the caregiver's identity, the control circuitry may display a screen on the graphical display screen that may require the caregiver to enter a personal identification number (PIN) in response to the at least one input being used. Entry of the PIN by the caregiver may provide the verification required by the control circuitry prior to sending data to the EMR system.

Alternatively or additionally, a card reader may be coupled to the control circuitry and the control circuitry may require the caregiver to engage the card reader with an identification (ID) card in response to the at least one input being used. For example, a caregiver may engage the card reader by inserting the ID card in a slot or swiping the ID card through a slot. In any event, engaging the card reader with the ID card by the caregiver may provide the verification required by the control circuitry prior to sending data to the EMR system. The ID card may be of the type having a magnetic strip and the card reader may be a magnetic card reader, for example.

Further alternatively or additionally, a wireless tag reader may be coupled to the control circuitry. The control circuitry may determine whether a wireless tag assigned to the caregiver is in communication with the wireless tag reader in response to the at least one input being used. Thus, communication between the wireless tag and the wireless tag reader may provide the verification required by the control circuitry prior to sending data to the EMR system. Also contemplated by this disclosure as alternative is the use of a biometric sensor that is coupled to the control circuitry and that receives an input that provides the verification required by the control circuitry prior to sending data to the EMR system. In such embodiments, the biometric sensor may comprise one or more fingerprint readers or retinal scanners that are used to identify the caregiver by reading a caregiver's fingerprint (e.g., a thumb print) or by scanning a caregiver's retina.

In some embodiments, the graphical user interface may display a bed status charting icon that may be selectable to display current bed status data that the caregiver may have the option of charting to the patient's EMR. Selection of the bed status charting icon may result in at least one of the following bed status data being displayed on the graphical user interface: an angle of a head section of the patient support structure, whether or not caster brakes of the patient support structure are set, whether or not an upper frame of the patient support structure is in a low position relative to a base of the patient support structure, whether a patient position monitoring system of the hospital bed is armed, and whether a head of bed monitoring system of the hospital bed is armed. The graphical user interface may display a chart button that may be touched to send the current bed status data to the patient's EMR. Alternatively or additionally, the graphical user interface may display a chart button that, when touched, may result in the graphical user interface displaying a confirmation screen which the caregiver may use to confirm that the current bed status data is to be charted to the patient's EMR. The graphical user interface may display a history button that may be touched to access a history of bed status data that has been charted to the patient's EMR previously.

In some embodiments, the graphical user interface may display a vital signs charting icon that may be selectable to display a patient information screen that the caregiver may use to enter the patient's vital signs data for subsequent charting to the patient's EMR. The patient information screen may include fields for entering at least one of the following patient's vital signs data: heart rate, respiration rate, blood pressure, pulse oximetry, and temperature. The graphical user interface may display a chart button that may be touched to send the patient's vital signs data to the patient's EMR. Alternatively or additionally, the graphical user interface may display a chart button that, when touched, may result in the graphical user interface displaying a confirmation screen which the caregiver may use to confirm that the patient's vital signs data is to be charted to the patient's EMR. The graphical user interface may display a history button that is touched to access a history of the patient's vital signs data that has been charted to the patient's EMR previously.

In some embodiments, the graphical user interface may display a weigh patient button that may be touched to command the control circuitry to weigh the patient supported on the patient support structure and to display a charting icon that the caregiver has the option of touching to initiate the charting of the patient's weight to the patient's EMR. A history button may be provided on the graphical display screen that may be selected to access a history of the patient's weight that has been charted to the patient's EMR previously.

In some embodiments, the graphical user interface may display a patient activity icon that may be selectable to display an activity screen that may have a menu of patient activities that the caregiver has the option of selecting for charting to the patient's EMR. The menu of patient activities may include, for example, at least one of the following activities: whether the patient is lying on their back, whether the patient is light on their right side, whether the patient is lying on their left side, whether the patient has moved out of the hospital bed and is sitting on a chair, and whether the patient support structure has been moved to a chair position to support the patient in a sitting position. The graphical user interface may display a chart button that may be touched to send patient activities data to the patient's EMR. Alternatively or additionally, the graphical user interface may display a chart button that, when touched, may result in the graphical user interface displaying a confirmation screen which the caregiver may use to confirm that patient activities data is to be charted to the patient's EMR. The graphical user interface may display a history button that may be touched to access a history of the patient activities data that has been charted to the patient's EMR previously.

In some embodiments, the graphical user interface may be used to display contraindications for a patient. For example, the graphical user interface may display at least one of the following: a list of a patient's drug allergies, a list of a patient's food allergies, a contraindication relating to a needle stick, and a contraindication relating to patient egress.

Alternatively or additionally, the graphical user interface may be used to display information regarding a patient's intakes and outputs. The information regarding a patient's intakes may include, for example, at least one of the following: a percent of the amount of food eaten by a patient during a meal or snack, a volume of liquid consumed by a patient, an amount of eating or drinking assistance provided by a caregiver to a patient, and a time at which a patient ate or drank. The information regarding a patient's outputs may include at least one of the following: an amount of urine output by a patient, an amount of stool output by a patient, an amount of emesis output by a patient, and a time at which a patient output occurred.

In some embodiments, the graphical user interface is used to display a rounding checklist which may have, for example, a list of tasks or functions to be performed by a caregiver. The list of tasks or functions may include one or more of the following: putting siderails up, setting brakes, putting an upper frame of the hospital bed in its lowest position, raising a head section of the hospital bed to a position above 30° of elevation, making sure a pathway to a bathroom is clear, making sure a night light is on, arming a bed exit system, assessing a pain level of a patient, making sure entertainment or nurse call controls are with reach of a patient, checking a patient's vital signs, checking whether IV pump bag or drainage receptacle needs to be replaced or emptied, turning a patient, making sure no trip hazards are present in a room, checking or changing bandages, checking to see if a patient needs drinking water, and checking to see if a patient needs to go to a bathroom.

In some embodiments, the graphical user interface is used to display a list of procedures which, in turn, each may include a list of steps of the associated procedure. In some contemplated embodiments, the graphical user interface is used to link to video clips which demonstrate on the graphical user interface at least a portion of a procedure. For example, a video clip of each step of a procedure may be shown on the graphical user interface.

According to this disclosure, the graphical user interface may be used to show information about network connectivity and/or information about a patient that is likely to be associated with the hospital bed. In such embodiments, a button or icon may be provided on the graphical user interface for selection by a caregiver to accept association of the patient with the hospital bed.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
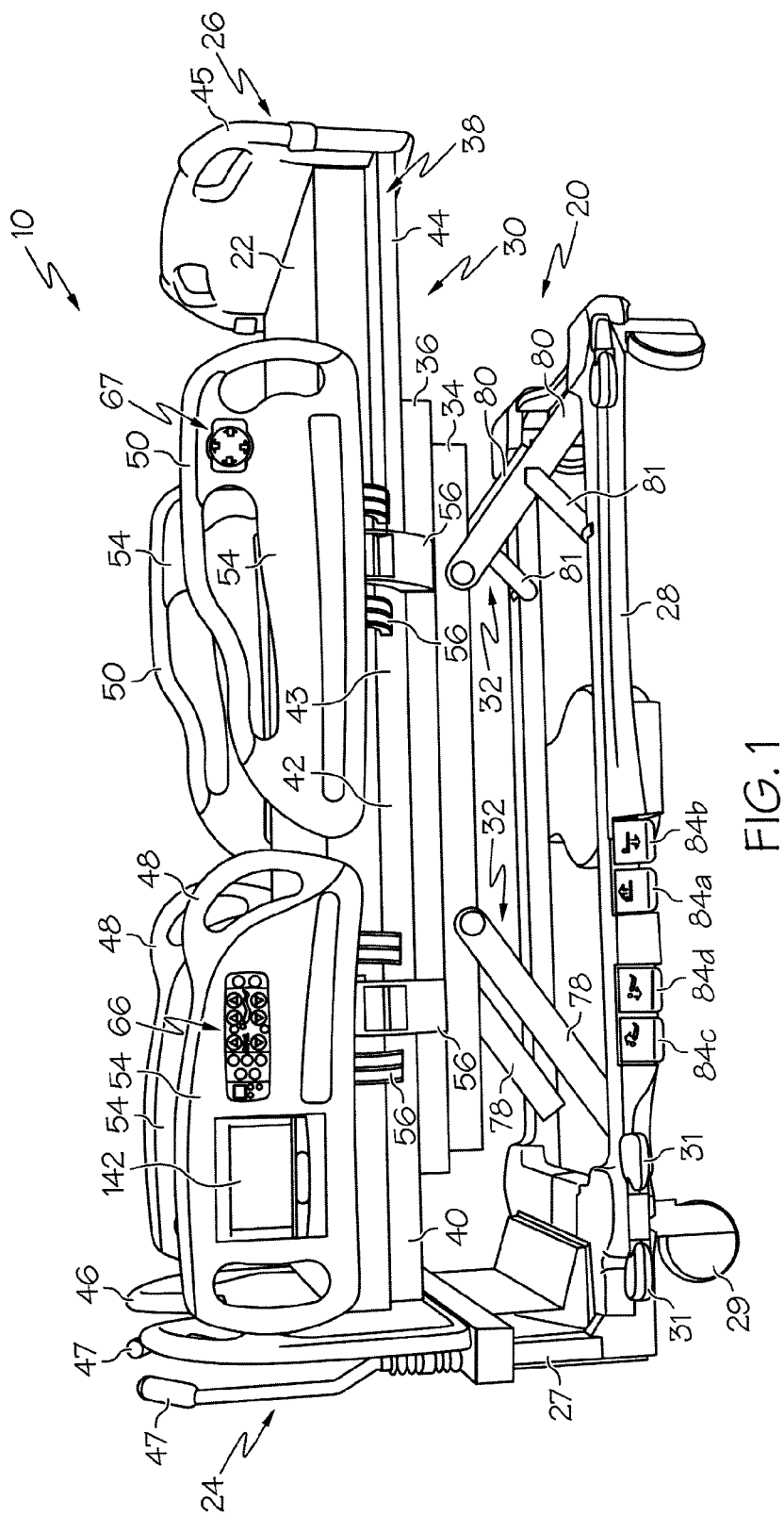
FIG. 1 is a perspective view of a hospital bed having a graphical user interface or display screen coupled to a siderail of the hospital bed.
Figure 2:
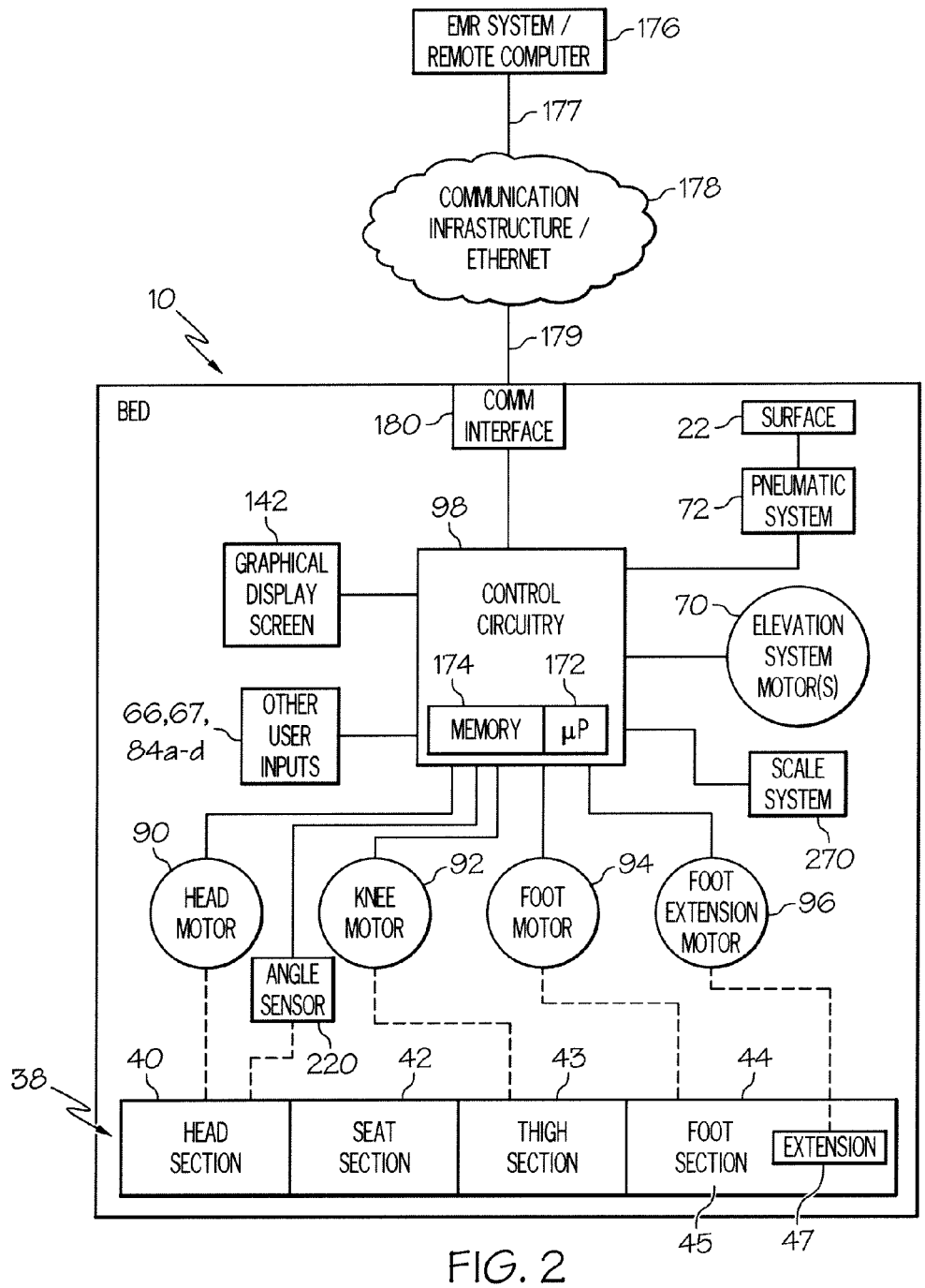
FIG. 2 is a block diagram showing electrical circuitry of the hospital bed in communication with a remote computer of an EMR system.

A patient support apparatus, such as illustrative hospital bed 10, includes a patient support structure such as a frame 20 that supports a surface or mattress 22 as shown in FIG. 1. As compared to prior art beds, bed 10 includes electronic medical record (EMR) charting capability that permits information or data to be charted into a patient's EMR via commands entered on bed 10 without the need for subsequent confirmatory actions by personnel at separate or remote computers. The screens shown in FIGS. 3-40 relate to the entry of data from bed 10 into a patient's EMR. FIGS. 1 and 2 show some details of one possible bed 10 having EMR charting capability. However, this disclosure is applicable to other types of patient support apparatuses, including other types of beds, surgical tables, examination tables, stretchers, and the like.

Referring now to FIG. 1, bed 10 has a frame 20 which includes a base 28, an upper frame assembly 30 and a lift system 32 coupling upper frame assembly 30 to base 28. Lift system 32 is operable to raise, lower, and tilt upper frame assembly 30 relative to base 28. Bed 10 has a head end 24 and a foot end 26. Hospital bed 10 further includes a footboard 45 at the foot end 26 and a headboard 46 at the head end 24. Illustrative bed 10 includes a pair of push handles 47 coupled to an upstanding portion 27 of base 28 at the head end 24 of bed 10. Headboard 46 is coupled to upstanding portion 27 of base as well. Foot board 45 is coupled to upper frame assembly 30. Base 28 includes wheels or casters 29 that roll along floor (not shown) as bed 10 is moved from one location to another. A set of foot pedals 31 are coupled to base 31 and are used to brake and release casters 29.

Illustrative hospital bed 10 has four siderail assemblies coupled to upper frame assembly 30 as shown in FIG. 1. The four siderail assemblies include a pair of head siderail assemblies 48 (sometimes referred to as head rails) and a pair of foot siderail assemblies 50 (sometimes referred to as foot rails). Each of the siderail assemblies 48 and 50 is movable between a raised position, as shown in FIG. 1, and a lowered position (not shown). Siderail assemblies 48, 50 are sometimes referred to herein as siderails 48, 50. Each siderail 48, 50 includes a barrier panel 54 and a linkage 56. Each linkage 56 is coupled to the upper frame assembly 30 and is configured to guide the barrier panel 54 during movement of siderails 48, 50 between the respective raised and lowered positions. Barrier panel 54 is maintained by the linkage 56 in a substantially vertical orientation during movement of siderails 48, 50 between the respective raised and lowered positions.

Upper frame assembly 30 includes a lift frame 34, a weigh frame 36 supported with respect to lift frame 34, and a patient support deck 38. Patient support deck 38 is carried by weigh frame 36 and engages a bottom surface of mattress 22. Patient support deck 38 includes a head section 40, a seat section 42, a thigh section 43 and a foot section 44 in the illustrative example as shown in FIG. 1 and as shown diagrammatically in FIG. 2. Sections 40, 43, 44 are each movable relative to weigh frame 36. For example, head section 40 pivotably raises and lowers relative to seat section 42 whereas foot section 44 pivotably raises and lowers relative to thigh section 43. Additionally, thigh section 43 articulates relative to seat section 42. Also, in some embodiments, foot section 44 is extendable and retractable to change the overall length of foot section 44 and therefore, to change the overall length of deck 38. For example, foot section 44 includes a main portion 45 and an extension 47 in some embodiments as shown diagrammatically in FIG. 2.

In the illustrative embodiment, seat section 42 is fixed in position with respect to weigh frame 36 as patient support deck 38 moves between its various patient supporting positions including a horizontal position, shown in FIG. 1, to support the patient in a supine position, for example, and a chair position (not shown) to support the patient in a sitting up position. In other embodiments, seat section 42 also moves relative to weigh frame 36, such as by pivoting and/or translating. Of course, in those embodiments in which seat section 42 translates along upper frame 42, the thigh and foot sections 43, 44 also translate along with seat section 42. As bed 10 moves from the bed position to the chair position, foot section 44 lowers relative to thigh section 43 and shortens in length due to retraction of the extension 47 relative to main portion 45. As bed 10 moves from the chair position to the bed position, foot section 44 raises relative to thigh section 43 and increases in length due to extension of the extension relative to main portion 45. Thus, in the chair position, head section 40 extends upwardly from weigh frame 36 and foot section extends downwardly from thigh section 43.

As shown diagrammatically in FIG. 2, bed 10 includes a head motor or actuator 90 coupled to head section 40, a knee motor or actuator 92 coupled to thigh section 43, a foot motor or actuator 94 coupled to foot section 44, and a foot extension motor or actuator 96 coupled to foot extension 47. Motors 90, 92, 94, 96 may include, for example, an electric motor of a linear actuator. In those embodiments in which seat section 42 translates along upper frame 30 as mentioned above, a seat motor or actuator (not shown) is also provided. Head motor 90 is operable to raise and lower head section 40, knee motor 92 is operable to articulate thigh section 43 relative to seat section 42, foot motor 94 is operable to raise and lower foot section 44 relative to thigh section 43, and foot extension motor 96 is operable to extend and retract extension 47 of foot section 44 relative to main portion 44 of foot section 44.

In some embodiments, bed 10 includes a pneumatic system 72 that controls inflation and deflation of various air bladders or cells (some of which are shown diagrammatically as icons in FIGS. 37, 39 and 40) of mattress 22. The pneumatic system 72 is represented in FIG. 2 as a single block but that block 72 is intended to represent one or more air sources (e.g., a fan, a blower, a compressor) and associated valves, manifolds, air passages, air lines or tubes, pressure sensors, and the like, as well as the associated electric circuitry, that are typically included in a pneumatic system for inflating and deflating air bladders of mattresses.

As also shown diagrammatically in FIG. 2, lift system 32 of bed 10 includes one or more elevation system motors or actuators 70, which in some embodiments, comprise linear actuators with electric motors. Thus, actuators 70 are sometimes referred to herein as motors 70. Alternative actuators or motors contemplated by this disclosure include hydraulic cylinders and pneumatic cylinders, for example. The motors 70 of lift system 32 are operable to raise, lower, and tilt upper frame assembly 30 relative to base 28. In the illustrative embodiment, one of motors 70 is coupled to, and acts upon, a set of head end lift arms 78 and another of motors 70 is coupled to, and acts upon, a set of foot end lift arms 80 to accomplish the raising, lowering and tilting functions of upper frame 30 relative to base 28. Guide links 81 are coupled to base 28 and to lift arms 80 in the illustrative example as shown in FIG. 1. Lift system of bed 10 is substantially similar to the lift system of the VERSACARE® bed available from Hill-Rom Company, Inc. Other aspects of bed 10 are also substantially similar to the VERSACARE® bed and are described in more detail in U.S. Pat. Nos. 6,658,680; 6,611,979; 6,691,346; 6,957,461; and 7,296,312, each of which is hereby expressly incorporated by reference herein.

In the illustrative example, bed 10 has four foot pedals 84a, 84b, 84c, 84d coupled to base 28 as shown in FIG. 1. Foot pedal 84a is used to raise upper frame assembly 30 relative to base 28, foot pedal 84b is used to lower frame assembly 30 relative to base 28, foot pedal 84c is used to raise head section 40 relative to frame 36, and foot pedal 84d is used to lower head section 40 relative to frame 36. In other embodiments, foot pedals 84a-d are omitted.

Each of siderails 48 includes a first user control panel 66 coupled to the outward side of the associated barrier panel 54 and each of siderails 50 include a second user control panel 67 coupled to the outward side of the associated barrier panel 54. Controls panels 66, 67 include various buttons that are used by a caregiver (not shown) to control associated functions of bed 10. For example, control panel 66 includes buttons that are used to operate head motor 90 to raise and lower the head section 40, buttons that are used to operate knee motor to raise and lower the thigh section, and buttons that are used to operate motors 70 to raise, lower, and tilt upper frame assembly 30 relative to base 28. In the illustrative embodiment, control panel 67 includes buttons that are used to operate motor 94 to raise and lower foot section 44 and buttons that are used to operate motor 96 to extend and retract foot extension 47 relative to main portion 45. In some embodiments, the buttons of control panels 66, 67 comprise membrane switches.

As shown diagrammatically in FIG. 2, bed 10 includes control circuitry 98 that is electrically coupled to motors 90, 92, 94, 96 and to motors 70 of lift system 32. Control circuitry 98 is represented diagrammatically as a single block 98 in FIG. 6, but control circuitry 98 in some embodiments comprises various circuit boards, electronics modules, and the like that are electrically and communicatively interconnected. Control circuitry 98 includes one or more microprocessors 172 or microcontrollers that execute software to perform the various control functions and algorithms described herein. Thus, circuitry 98 also includes memory 174 for storing software, variables, calculated values, and the like as is well known in the art.

As also shown diagrammatically in FIG. 2, a user inputs block represents the various user inputs such as buttons of control panels 66, 67 and pedals 84a-d, for example, that are used by the caregiver or patient to communicate input signals to control circuitry 98 of bed 10 to command the operation of the various motors 70, 90, 92, 94, 96 of bed 10, as well as commanding the operation of other functions of bed 10. Bed 10 includes at least one graphical user input or display screen 142 coupled to a respective siderail 48 as shown in FIG. 1. Display screen 142 is coupled to control circuitry 142 as shown diagrammatically in FIG. 2. In some embodiments, two graphical user interfaces 142 are provided and are coupled to respective siderails 48. Alternatively or additionally, one or more graphical user interfaces are coupled to siderails 50 and/or to one or both of the headboard 46 and footboard 45. Control circuitry 98 receives user input commands from graphical display screen 142 as will be described in further detail below with regard to FIGS. 3-40.

According to this disclosure, control circuitry 98 of bed 10 communicates with a remote computer device 176 via communication infrastructure 178 such as an Ethernet of a healthcare facility in which bed 10 is located and via communications links 177, 179 as shown diagrammatically in FIG. 2. Computer device 176 is sometimes simply referred to as a "computer" herein. Remote computer 176 is part of an electronic medical records (EMR) system according to this disclosure. However, it is within the scope of this disclosure for circuitry 98 of bed 10 to communicate with other computers such as those included as part of a nurse call system, a physician ordering system, an admission/discharge/transfer (ADT) system, or some other system used in a healthcare facility in other embodiments. Ethernet 178 in FIG. 2 is illustrated diagrammatically and is intended to represent all of the hardware and software that comprises a network of a healthcare facility.

In the illustrative embodiment, bed 10 has a communication interface or port 180 which provides bidirectional communication via link 179 with infrastructure 178 which, in turn, communicates bidirectionally with computer 176 via link 177. Link 179 is a wired communication link in some embodiments and is a wireless communications link in other embodiments. Thus, communications link 179, in some embodiments, comprises a cable that connects bed 10 to a wall mounted jack that is included as part of a bed interface unit (BIU) or a network interface unit (NIU) of the type shown and described in U.S. Pat. Nos. 7,538,659 and 7,319,386 and in U.S. Patent Application Publication Nos. 2009/0217080 A1, 2009/0212925 A1 and 2009/0212926 A1, each of which are hereby expressly incorporated by reference herein. In other embodiments, communications link 179 comprises wireless signals sent between bed 10 and a wireless interface unit of the type shown and described in U.S. Patent Application Publication No. 2007/0210917 A1 which is hereby expressly incorporated by reference herein. Communications link 177 comprises one or more wired links and/or wireless links as well according to this disclosure.

As mentioned above, bed 10 includes EMR charting capability so that information can be charted into a patient's EMR via commands entered on bed 10 without the need for subsequent confirmatory actions by personnel at remote computers. In some embodiments contemplated by this disclosure, subsequent confirmatory actions may be required at EMR system computer 176 prior to entry of data into a patient's EMR. However, systems in which information is charted or stored in a patient's EMR via caregiver actions at bed 10 without the need for subsequent actions at remote computer 176 by the same or a different caregiver is seen as being more efficient.

In the description of FIGS. 3-40 that follows, screens that appear on graphical user interface 142 are discussed. The images and functions associated with each of these screens are controlled by the software that is stored in memory, such as memory 174 shown diagrammatically in FIG. 2, and executed by a microprocessor or microcontroller, such as microprocessor 172 shown diagrammatically in FIG. 2. In some implementations, multiple microprocessors or microcontrollers and multiple memory devices are used in connection with displaying the various screens on graphical user interface 142 and carrying out the various functions associated with those screens. For example, in some embodiments, graphical user interface 142 includes its own display driver circuitry that includes its own microprocessor or microcontroller and its own memory. Thus, software is stored in multiple memory locations in some embodiments and is executed by associated microprocessors or microcontrollers to perform the overall functionality discussed below.

Figure 3:
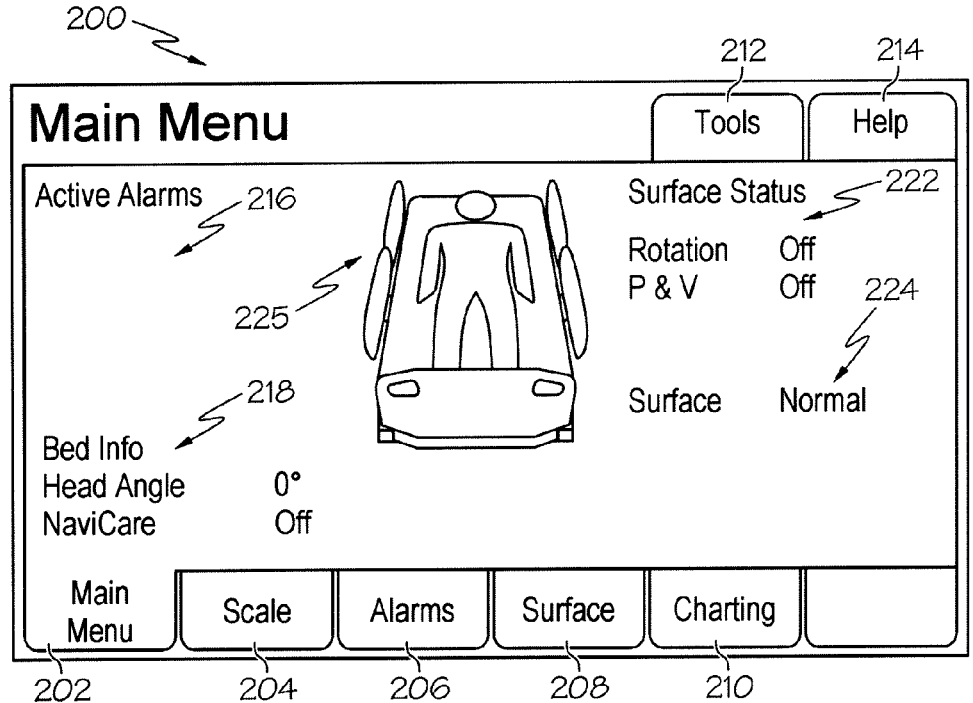
FIG. 3 is an example of a Main Menu screen that appears on the graphical user interface as a default screen.

Referring now to FIG. 3, an example of a Main Menu screen 200 that appears on the graphical user interface 142 as a default screen is shown. Screen 200 includes a Main Menu tab 202 which is associated with screen 200. Screen 200 also has a Scale tab 204, an Alarms tab 206, a Surface tab 208, a Charting tab 210, a Tools tab 212, and a Help tab 214. Tabs 202, 204, 206, 208, 210, 212, 214 are selected or touched to call up an associated screen or set of screens. Thus, when navigating on screens associated with tabs 204, 206, 208, 210, 212, 214, the user simply selects tab 202 if the user wishes to return to the Main Menu screen 200. In addition to the details provided herein, further details of graphical user interface 142 and the screens that appear thereon can be found in U.S. Patent Application Publication No. 2008/0235872 A1 which is hereby expressly incorporated by reference herein.

Main menu screen 200 includes an Active Alarms field 216 in which any alarms associated with bed 10 are listed. In the illustrative example, there are no alarm conditions occurring with respect to bed 10 and so field 216 is empty. A Bed Info field 218 appears on screen 200 beneath field 216 and displays information such as the head angle of bed 10 (i.e., the angle at which head section 40 is raised with respect to frame 36 or with respect to horizontal depending upon the type of angle sensor used). Bed 10 includes an angle sensor 220 which is coupled to head section 40 and to control circuitry 98 as shown diagrammatically in FIG. 2. Examples of suitable angle sensors include, for example, potentiometers, inclinometers, ball switches, and accelerometers, just to name a few. In the illustrative example of FIG. 3, the head angle is 0°.

In the Bed Info field 218 of screen 200 there is also a line of text that indicates that nurse call alerting is turned off. That is, for the particular bed 10, no bed conditions are being monitored by a remote nurse call system for alerting caregivers of any alarm conditions. In the given example, the line of text states "NaviCare OFF." The term NaviCare in field 218 refers to the NAVICARE® Nurse Call (NNC) system available from Hill-Rom Company, Inc. In some embodiments, the ability of bed 10 to chart information to the EMR system 176 is independent of whether bed 10 is connected to a nurse call system and is independent of whether, if connected, the alerting functions of bed 10 to the nurse call system are turned on or off. In other embodiments, bed 10 may communicate with the EMR system 176 via a nurse call system, ADT system, or other system and therefore, connectivity to the intermediate system or systems is required in those particular embodiments.

Screen 200 also has a Surface Status field 222 that conveys information about the status of mattress 22. In the illustrative example, field 222 indicates that a rotation therapy feature of mattress 22 is off and that a percussion and vibration (P&V) feature of mattress 22 is off. Screen further has a Surface mode field 224 that conveys information about the mode in which mattress 22 is operating. In the illustrative example, the surface 22 is operating in the normal mode. Other modes include, for example, a pressure redistribution mode, a max-inflate mode, a right turn mode, a left turn mode, and a seat deflate mode. Screen 200 has a bed icon 225 that visually conveys further information about bed 10 in some embodiments. For example, there are four siderails of icon 225 are color coded red to indicate that the respective siderail has been lowered and indicia appears on a mattress portion of icon 225 to indicate different types of surface therapy or mode information.

Figure 4:
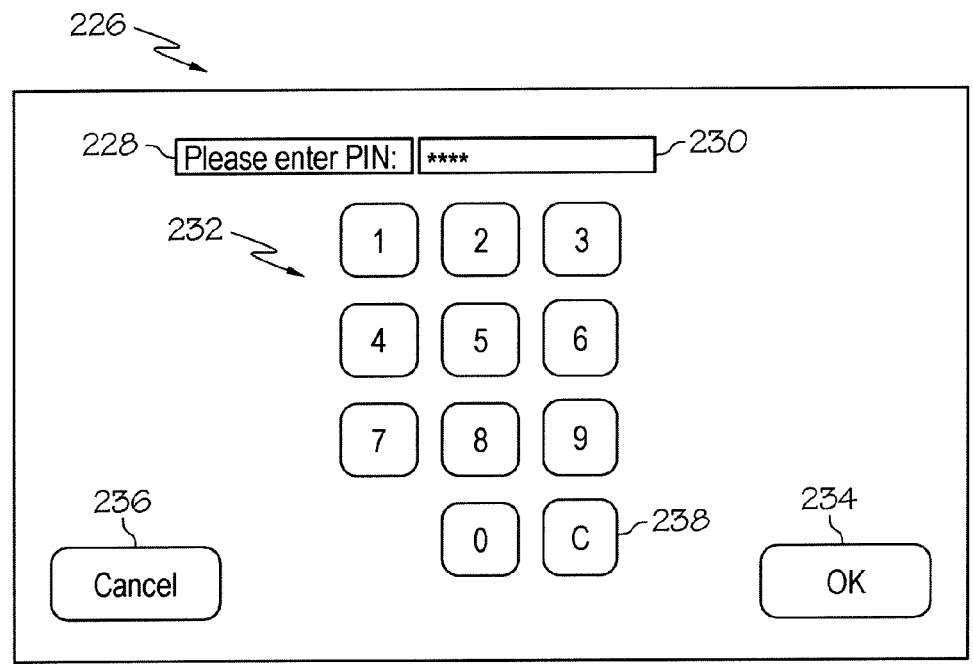
FIG. 4 is a screen shot of a Log In screen that appears on the graphical user interface in response to a user touching a Charting tab so that the user can verify their identity as being a person authorized to chart data to the EMR system.
Figure 5:
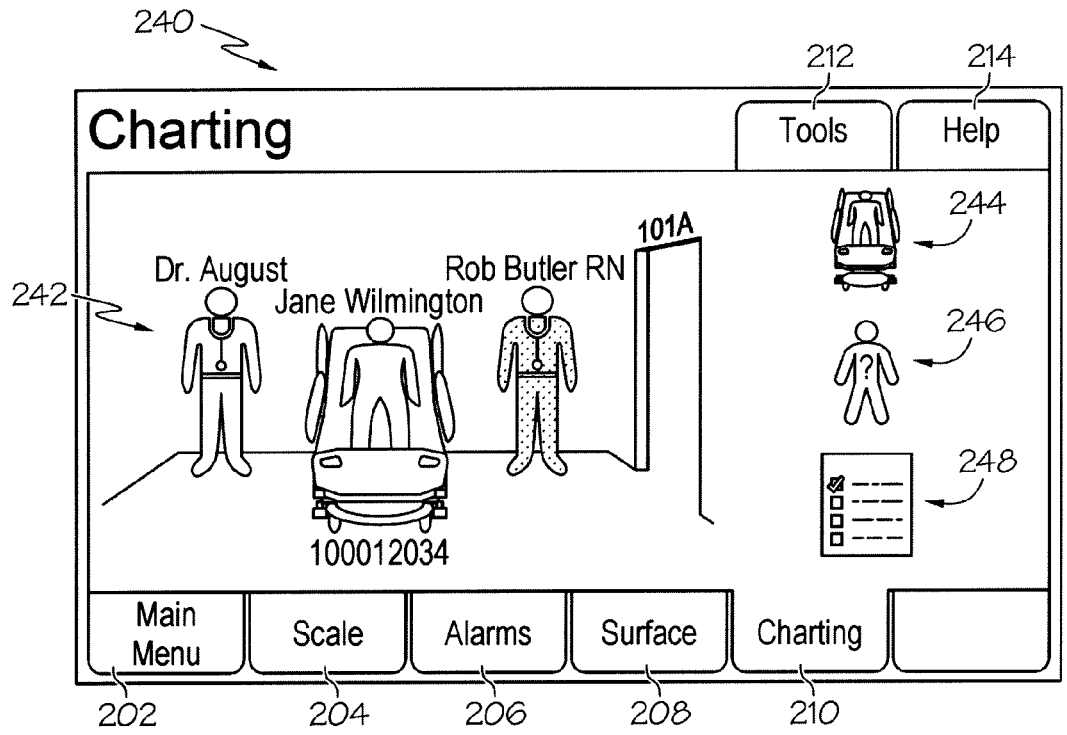
FIG. 5 is an example of a Charting Home screen that appears on the graphical user interface after the user has successfully verified their identity using the Log In screen, the Log In screen having information regarding the patient, the doctor and nurse assigned to the patient, the bed serial number of the patient's bed, and the patient's room assignment, and the Log In screen having Bed Status, Patient Info, and Activity icons on the right hand side of the screen shot.

If a caregiver selects or touches Charting tab 210, a Log In screen or pop-up window 226, an example of which appears in FIG. 4, appears on the graphical user interface 142. Screen 226 has user inputs and fields that are used by the caregiver to verify their identity as being a person authorized to chart data to the EMR system 176. For example, in the illustrative embodiment, screen 226 includes a field 228 with the text "Please enter PIN" to prompt the caregiver to use a numeric keyboard 232 having buttons corresponding to integers 0-9 to type a personal identification number (PIN). As the caregiver uses keyboard 228 to type the associated PIN, asterisks appear in a PIN field 230. Once the entire correct PIN is entered into field 230, the caregiver touches or selects an OK button or icon 234 and a Charting Home screen 240, an example of which is shown in FIG. 5, appears on graphical user interface 142. If a user selects a Cancel button 236 on screen 226, then Main Menu screen 200 is displayed on graphical user interface 142. Keyboard 232 includes a C button 238 that is pressed to clear the PIN being entered into field 230. Thus, button 238 is used if the caregiver makes an inadvertent error while typing his or her PIN into field 230.

While the illustrative embodiment uses a PIN that is typed on Log In screen 226 to verify that a caregiver is authorized to chart data to EMR system 176, other possibilities for verifying the caregiver's identity are within the scope of this disclosure. For example, bed 10 includes a token reader that reads a token in some embodiments. One type of token is a card with a magnetic strip and one type of token reader is a magnetic card reader which is engaged by the card, such as by swiping the card through a slot or by inserting the card into a slot or opening. Another type of token is a radio frequency identification (RFID) tag and another type of token reader is an RFID tag reader. The RFID tag and associated RFID tag reader include transmitters, receivers, and/or transceivers that are appropriately arranged for communicating with each other. To give one example, bed 10 has an RFID transceiver that sends out a wireless signal that, if received by an RFID tag in proximity to the transceiver, responds with a wireless message including a unique code associated with the RFID tag. The unique code of the RFID tag is associated with an assigned caregiver and is used to verify the identity of the caregiver in proximity to the bed 10.

Another alternative to the use of a PIN typed on Log In screen 226 for caregiver identification is the use of a biometric sensor that is coupled to the control circuitry 98 and that receives an input that provides the verification required by the control circuitry 98 prior to sending data to the EMR system 176. In such embodiments, the biometric sensor may comprise one or more fingerprint readers or retinal scanners that are used to identify the caregiver by reading a caregiver's fingerprint (e.g., a thumb print) or by scanning a caregiver's retina. The biometric sensor is mounted on one or both siderails 48 adjacent the associated display screen 142 in some embodiments, but the biometric sensor may just as well be mounted on some other portion of bed 10 such as the head board 46, foot board 45, one or both of siderails 50, or on an arm, pole, or pod that extends upwardly from upper frame 38, for example.

Referring to FIG. 5, Charting Home screen 240, which appears on graphical user interface 142 after the user has successfully verified their identity using the Log In screen 226 as discussed above, has a dynamic field 242 conveying information regarding the patient, the doctor and nurse assigned to the patient, the bed serial number of the patient's bed, and the patient's room assignment. In the illustrative example, the patient is Jane Wilmington, the patient's doctor is Dr. August, the primary caregiver currently assigned to the patient is Rob Butler, RN, the bed serial number is 100012034, and the patient's room assignment is room 101A. The information concerning the patient's name, the room location, the patient's doctor and assigned caregiver are retrieved from remote computer devices, such as those of the EMR system 176 or another system, such as a nurse call system, an ADT system, or the like. In some embodiments, screens are presented on graphical user interface 142 to enable a caregiver to verify the information in field 242, particularly, to verify the identity of the patient. The patient's name is displayed in a coded format, such as a HIPAA compliant format, in some embodiments.

Still referring to FIG. 5, Charting Home screen 240 has a Bed Status icon 244, a Patient Info icon 246, and an Activity icon 248. In response to the caregiver selecting Bed Status icon 244, a Bed Status screen is displayed on graphical user interface 142. Depending upon the status of various bed features, the Bed Status screen will convey different types of information. In the present disclosure, five examples of a Bed Status screen 250*a*, 250*b*, 250*c*, 250*d*, 250*e* are provided in FIGS. 6-10, respectively. Each Bed Status screen 250*a*, 250*b*, 250*c*, 250*d*, 250*e* has a partial bed indicia 252 located beneath a line of text 254 indicating "Current Bed Status" and indicating the room number, "101A" in the illustrative example. Partial bed indicia 252 includes a head angle alarm status bubble 256, a current head angle read out field 257, a caster brake status bubble 258, an elevation system status bubble 260, and a patient position monitoring (PPM) system status bubble 262.

Figure 6:
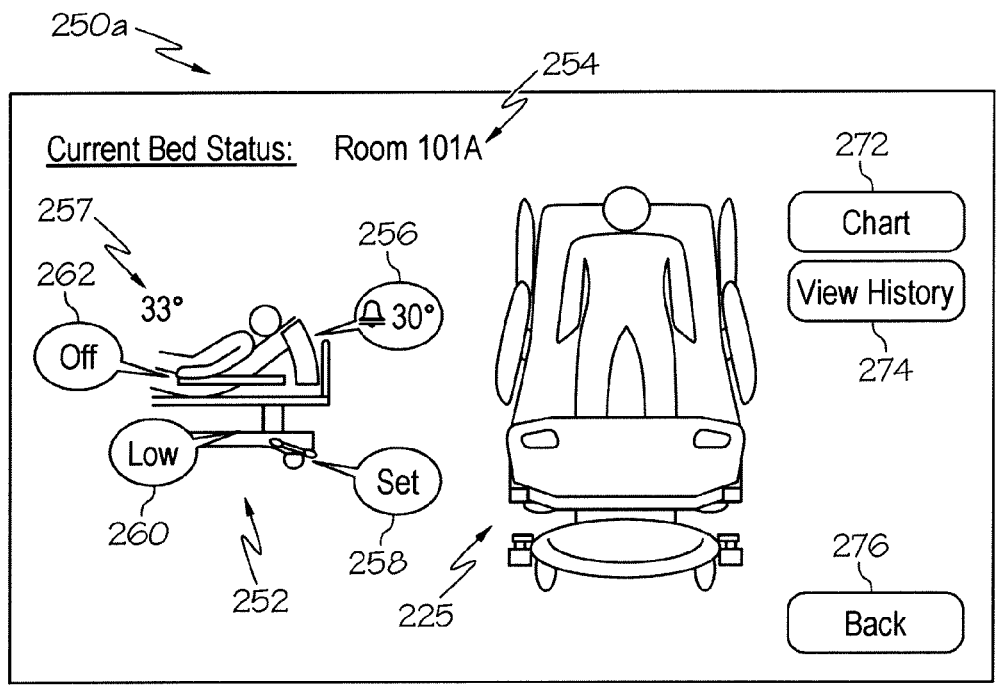
FIG. 6 is a first example of a Bed Status screen that appears on the graphical user interface in response to the Bed Status icon being touched on the Charting Home screen and, in the first example, an angle of a head section of the patient's bed is above a threshold angle and an upper frame of the bed is in a low position relative to a base of the bed.

Referring to FIG. 6, the first example of a Bed Status screen 250*a* is shown. In the first example, head angle alarm status bubble 256 indicates that a head angle alarm feature of bed 10 is armed and current head angle read out field 257 indicates that the head section 40 of bed 10 is at 33° which is not below the 30° threshold of the head angle alarm system in the illustrative example. Thus, head section 40 of bed 10 is raised sufficiently that a head of bed angle alarm condition does not exist in connection with the screen 250*a* example. Also on screen 250*a*, caster brake status bubble 258 indicates that the caster brakes are set, elevation system status bubble 260 indicates that upper frame assembly 30 is in its lowest position relative to base 28, and PPM system status bubble 262 indicates that the PPM system is turned off.

Figure 7:
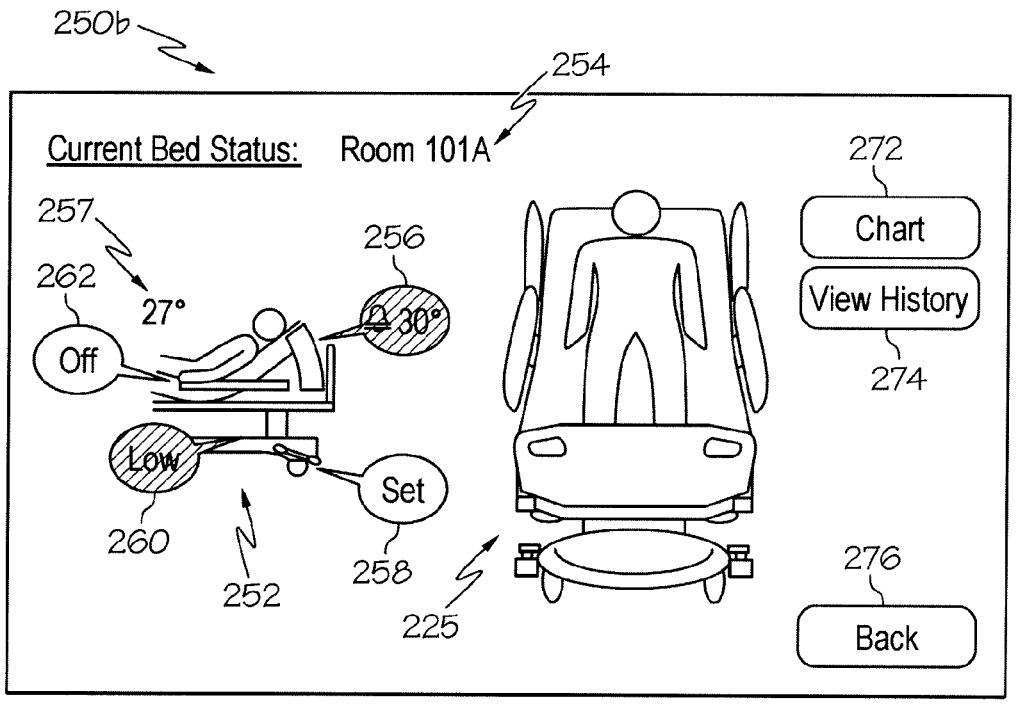
FIG. 7 is a second example of a Bed Status screen that appears on the graphical user interface in response to the Bed Status icon being touched and, in the second example, the angle of the head section of the patient's bed is below the threshold angle such that an angle alert icon is color coded yellow to indicate the alert condition and the upper frame of the bed is not in the low position relative to a base of the bed such that a low icon is color coded yellow to indicate the alert condition.

Referring to FIG. 7, the second example of a Bed Status screen 250*b* is shown. In the second example, head angle alarm status bubble 256 indicates that the head angle alarm feature of bed 10 is armed and current head angle read out field 257 indicates that the head section 40 of bed 10 is at 27° which is below the 30° threshold of the head angle alarm system in the illustrative example. Thus, head section 40 of bed 10 is not raised sufficiently which means that a bed angle alarm condition exists in connection with the screen 250*b* example. Because of the head angle alarm condition, bubble 256 is color coded (indicated by cross hatching in FIG. 7), such as being colored yellow or red, for example, to visually indicate the alarm condition. Also on screen 250a, caster brake status bubble 258 indicates that the caster brakes are set, elevation system status bubble 260 indicates that upper frame assembly 30 is not in its lowest position relative to base 28 and so is color coded to indicate the alarm condition, and PPM system status bubble 262 indicates that the PPM system is turned off.

Figure 8:
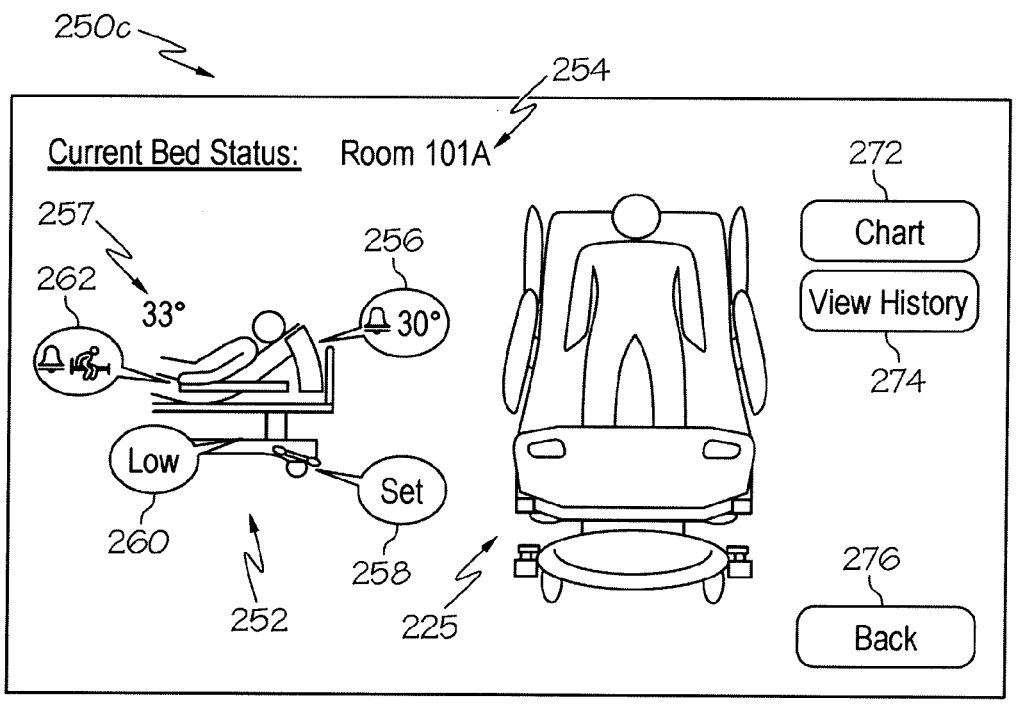
FIG. 8 is a third example of a Bed Status screen that appears on the graphical user interface in response to the Bed Status icon being touched and, in the third example, a patient position monitoring (PPM) system of the bed is armed in an Exiting mode as indicated by an Exiting mode icon appearing on the left side of the screen.
Figure 9:
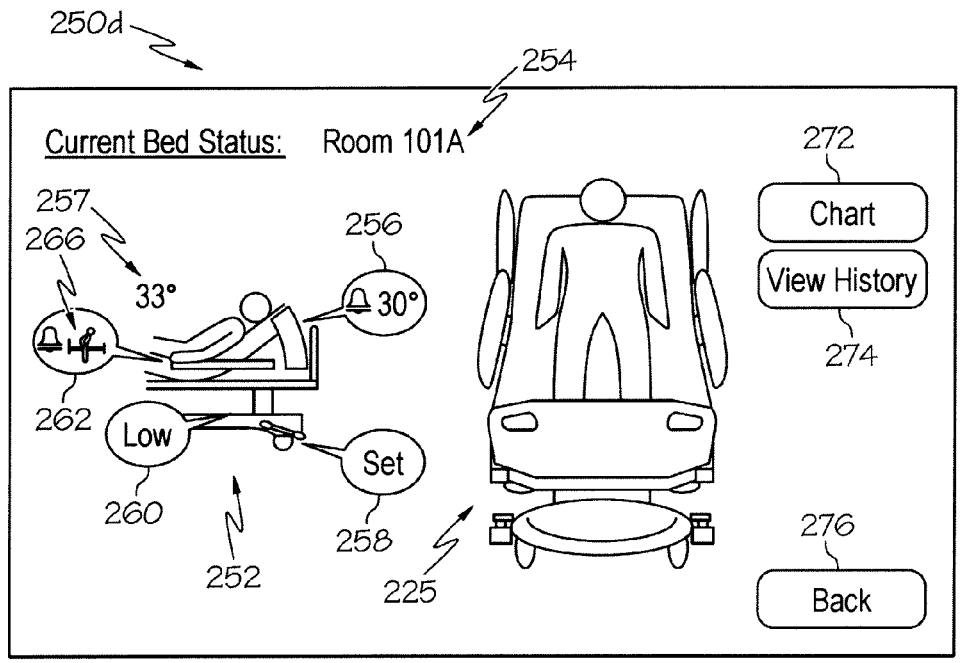
FIG. 9 is a fourth example of a Bed Status screen that appears on the graphical user interface in response to the Bed Status icon being touched and, in the fourth example, the PPM system of the bed is armed in an Out-of-Bed mode as indicated by an Out-of-Bed mode icon appearing on the left side of the screen.
Figure 10:
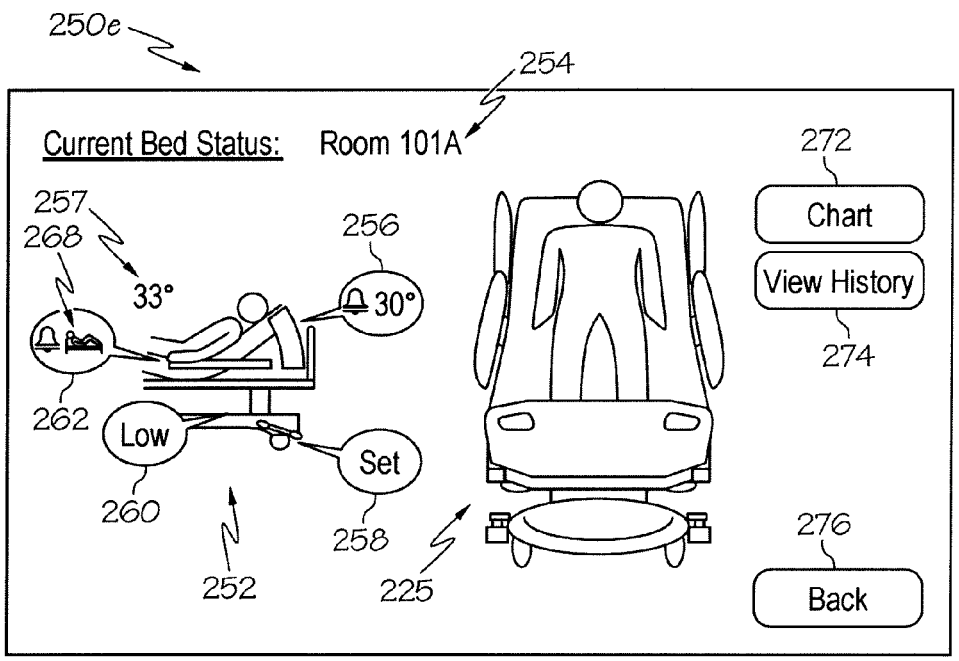
FIG. 10 is a fifth example of a Bed Status screen that appears on the graphical user interface in response to the Bed Status icon being touched and, in the fifth example, the PPM system of the bed is armed in a Patient Position mode as indicated by a Patient Position mode icon appearing on the left side of the screen.

Referring to FIGS. 8-10, the third, fourth and fifth examples of a Bed Status screen 250c, 250d, 250e are each the same as the first example of Bed Status screen 250a except that PPM system status bubble 262 has a different icon in each of screens 250c, 250d, 250e than in screen 250a to indicate a respective mode in which the PPM system of bed 10 is armed. In the illustrative examples, the PPM system of bed 10 is armed in an Exiting mode in connection with screen 250c as indicated by an Exiting mode icon 264 appearing in bubble 262 in FIG. 8, the PPM system of bed 10 is armed in an Out-of-Bed mode in connection with screen 250d as indicated by an Out-of-Bed mode icon 266 appearing in bubble 262 in FIG. 9, and the PPM system of bed 10 is armed in an Patient Portion mode in connection with screen 250e as indicated by a Patient Position mode icon 268 appearing in bubble 262 in FIG. 10.

Bed 10 includes a scale system 270 as shown diagrammatically in FIG. 2. Scale system 270 includes one or more weight sensors that are indicative of the weight of the patient on bed 10. In some embodiments, the scale system includes four load cells (e.g., load beams with strain gages) that interconnect lift frame 34 with weigh frame 36 adjacent the four corners of frame 34. In addition to sensing an amount of weight of the patient, the data from the sensors of scale system 270 is also used by control circuitry 98 to determine the patient's position relative to mattress 22 and/or upper frame assembly 22. Thus, in the illustrative example, data from the sensors of weigh scale system 270 is compared to thresholds associated with the Exiting, Out-of-Bed, and Patient Position modes of the PPM system to determine if an alarm condition exists. Examples of scale systems used on hospital beds are shown and described in U.S. Pat. Nos. 7,610,637; 7,253,366; 7,176,391; 6,924,441; 6,680,443; and 5,859,390, each of which is hereby incorporated by reference herein. See particularly U.S. Pat. No. 7,253,366 for a discussion of a load cell based PPM system having Exiting, Out-of-Bed, and Patient Position modes.

Figure 12:
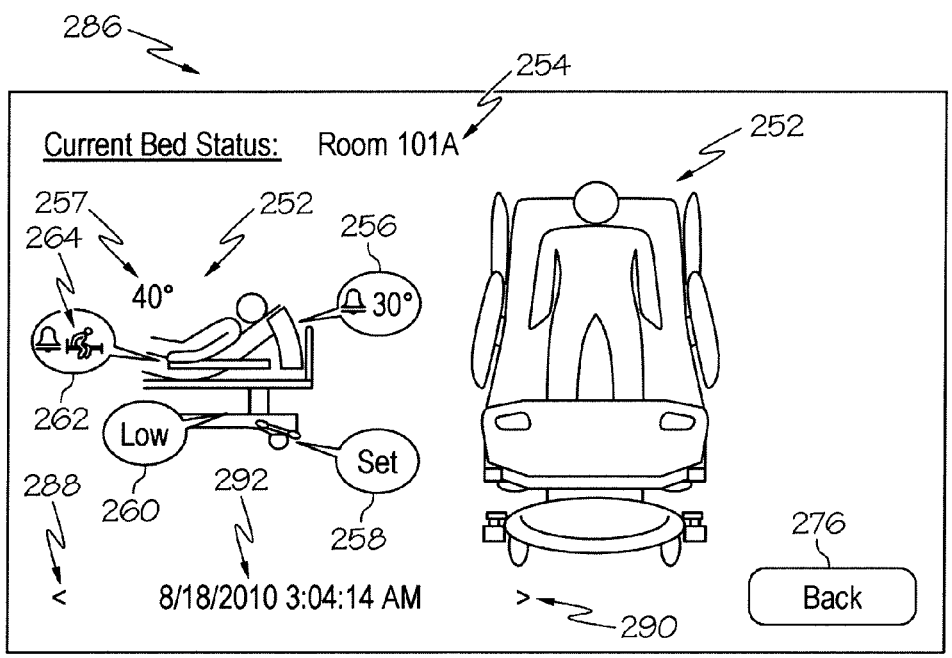
FIG. 12 is an example of a Bed Status History screen that appears on the graphical user interface in response to a Yes button or field being selected on the Charting Confirmation pop up window and the Bed Status History screen having left and right scroll arrows that are selected to scroll through Bed Status data that has been charted to the EMR system for the particular patient.

The Bed Status screen includes a Chart button or icon 272, a View History button or icon 274, and a Back button or icon 276 as shown in FIGS. 6-10. The Bed Status screen also has bed icon 225 that is substantially similar to bed icon 225 of screen 200 and that visually conveys further information about bed 10 in some embodiments as also shown in FIGS. 6-10. In response to selection of Back button 276 on the Bed Status screen, the Charting Home screen 240 is displayed on graphical user interface 142 without any of the bed status data on the Bed Status screen being charted or sent to the EMR system 176. In response to selection of the View History button 274 on the Bed Status screen, a Bed Status History screen 286, an example of which is shown in FIG. 12, appears on graphical user interface 142. Screen 286 is discussed in further detail below.

Figure 11:
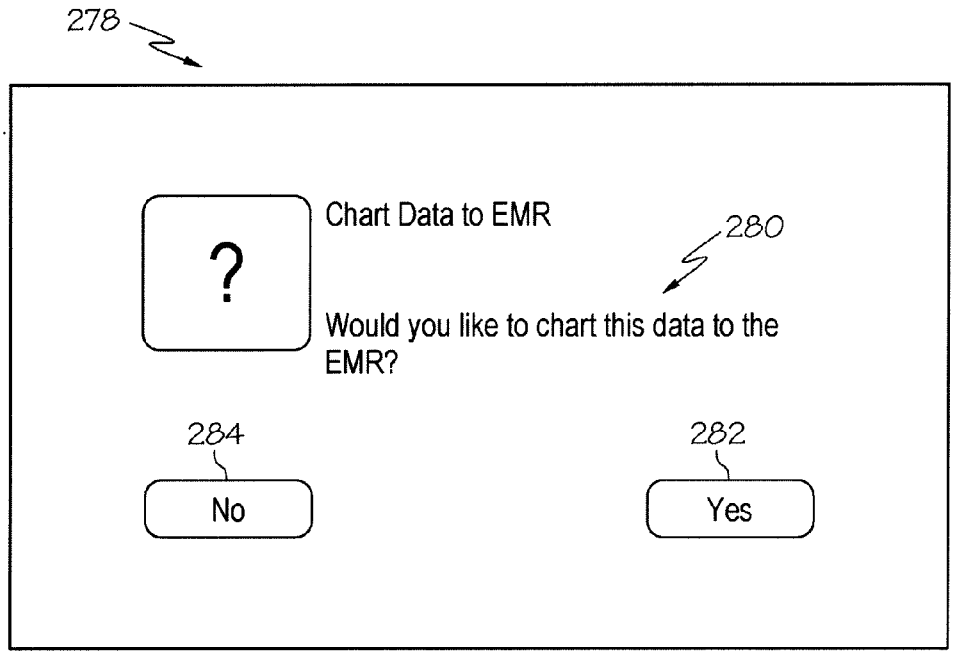
FIG. 11 is a Charting Confirmation pop up window that appears on the graphical user interface in response to a Chart button or field being touched on the Bed Status screen.

In response to selection of Chart button 272 on the Bed Status screen, a Charting Confirmation pop up window 278 appears on the graphical user interface 142 as shown in FIG. 11. Window 278 has text 280 which asks whether the caregiver wants to chart the bed status data appearing in bubbles 256, 258, 260, 262 and read out field 257 to the EMR of the associated patient. A Yes button or icon 282 and a No button or icon 284 are provided in window 278. In response to the selection of No button 284 of window 278, Charting Home screen 240 is once again displayed on graphical user interface 142 and none of the bed status data appearing on the Bed Status screen is charted or sent to the EMR system 176.

In response to the selection of Yes button 282 of window 278, the bed status data appearing in bubbles 256, 258, 260, 262 and read out field 257 is charted to the EMR of the associated patient and the Bed Status History screen 286 automatically appears on the graphical user interface 143 thereafter as shown, for example, in FIG. 12. The Bed Status History screen 286 has a left scroll arrow 288 and a right scroll arrow 290 that are selected to scroll through Bed Status data that has been charted to the EMR system for the particular patient. If the Yes button 282 was selected on window 278, then screen 286 initially shows the data that has just been charted to the EMR system 176 along with an associated date and time stamp 292. As arrows 288, 290 are used to scroll to data that was charted at different times, the date and time stamp 292 changes to match the date and time at which the particular data, which appears in bubbles 256, 258, 260, 262 and field 257 of partial bed indicia 252, was charted.

If Bed History screen 286 is arrived at in response to pressing the View History button 274 of the Bed Status screen, then screen 286 initially shows the most recent bed status data that has been previously been charted to the EMR system 176 and scroll arrows 288, 290 are used in the same manner as just described. Screen 286 also has back button 276 that, when selected, results in the Charting Home screen 240 shown in FIG. 5 for example, being displayed on the graphical user interface 142.

Figure 13:
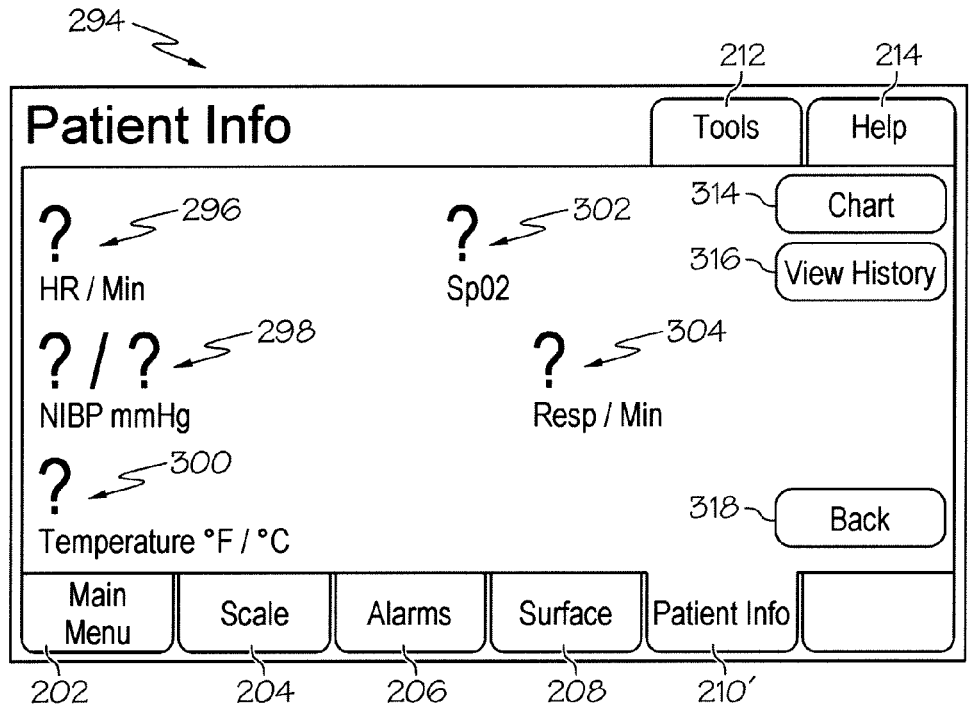
FIG. 13 is a Patient Info screen that appears on the graphical user interface in response to the Patient Info icon being touched on the Charting Home screen, the Patient Info screen having a number of question marks that are selectable for subsequent manual entry of patient information regarding heart rate, blood pressure, temperature, pulse oximitry and respiration rate.

In response to the caregiver selecting Patient Info icon 246 on the Charting Home screen 249, shown in FIG. 5, a Patient Info screen 294 is displayed on graphical user interface 142 as shown for example in FIG. 13. Charting tab 210 changes title from "Charting" to "Patient Info" on screen 294 and so is indicated as Patient Info tab 210'. A similar title change for tab 210 occurs in some embodiments when Bed status icon 244 is selected on screen 240. That is, in some embodiments, tab 210 changes title from "Charting" to "Bed Status" in response to selection of tab 244 on screen 240.

Screen 294 includes a heart rate field 296, a non-invasive blood pressure (NIBP) field 298, a temperature field 300, a pulse oximetry (SpO2) field 302, and a respiration rate field 304. In FIG. 13, all of fields 296, 298, 300, 302, 304 have question marks in them to indicate that none of the patient data has been entered into those fields by a caregiver yet. Thus, in the illustrative embodiment, a caregiver manually enters data into fields 296, 298, 300, 302, 304 for eventual charting to the EMR system 176 as will be discussed below. In other embodiments in which bed 10 has integrated sensors for sensing some or all of the patient data associated with fields 296, 298, 300, 302, 304, then fields 296, 298, 300, 302, 304 are auto-populated with the sensed patient data. In still other embodiments, in which control circuitry 98 of bed 10 is in communication with other patient care equipment, either via in-room connections (wired and/or wireless) between bed 10 and the other equipment or via communication infrastructure 178, then fields 296, 298, 300, 302, 304 are auto-populated with the corresponding patient data received by bed 10 from the other patient care equipment that gathers the patient data initially.

To manually enter patient data into fields 296, 298, 300, 302, 304 of Patient Info screen 294, the caregiver touches the particular field 296, 298, 300, 302, 304 into which the data is to be entered manually. In the discussion that follows concerning FIGS. 14-18, an example is given regarding the various options for manually entering the patient's heart rate data into field 296. A similar process is followed for entering the corresponding types of data into the other fields 298, 300, 302, 304. When entering data manually into fields 296, 298, 300, 302, 304, the caregiver may have measured the data himself or herself with a handheld or portable medical instrument or the caregiver may be viewing the data on some other device that is monitoring the patient, such as a vital signs monitor like an electrocardiograph (EKG), electronic blood pressure cuff, or pulse oximeter, just to name a few.

Figure 14:
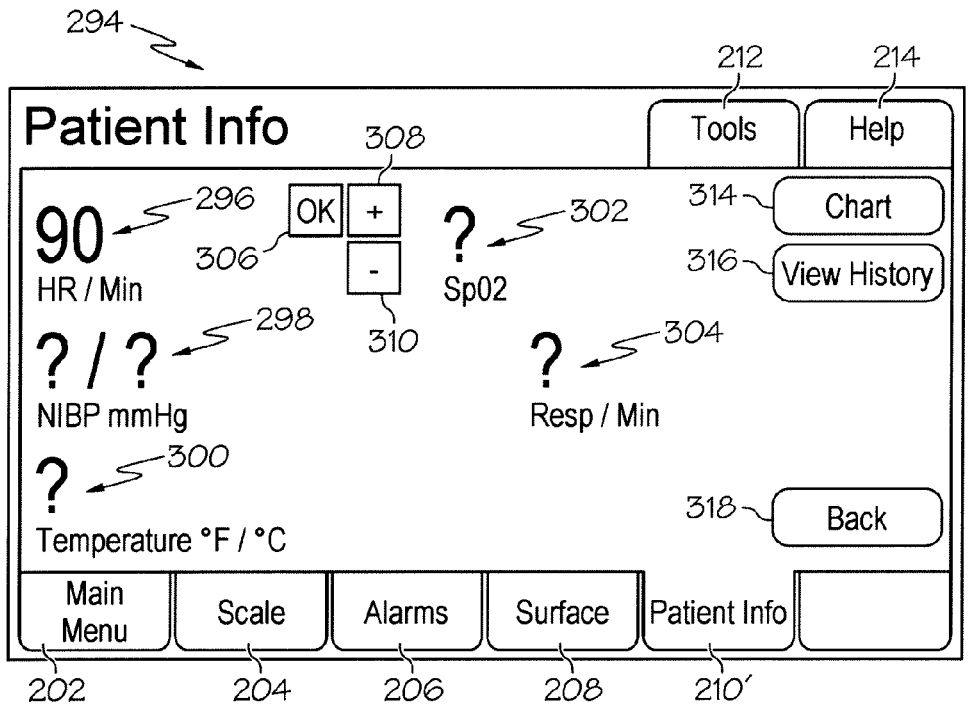
FIG. 14 is an example of the Patient Info screen after the heart rate question mark has been touched, the question mark being replaced with either a default heart rate or the last heart rate stored in the EMR system or in circuitry of the hospital bed and OK, plus and minus buttons or fields being displayed for manually changing the heart rate information.

If on Patient Info screen 294, the caregiver selects or touches heart rate field 296, then field 296 becomes populated with a default value in those instances when no data has been previously charted to the EMR system 176 and becomes populated with the data value most recently charted to the EMR system 176. In some embodiments, bed 10 retrieves the previously charted data from the EMR system 176 and in other embodiments, bed 10 stores the charted data locally, such as in memory 174, for subsequent retrieval. In the illustrative example, after field 296 is touched the number 90 appears in field 296 as shown in FIG. 14 to indicate that the previously charted heart rate, in beats per minute, for the associated patient on bed 10 is 90 beats per minute. An OK icon or button 306, a plus icon or button 308 and a minus icon or button 310 also appears on screen 294 to the right of field 296 in response to field 296 being touched as also shown in FIG. 14.

Figure 15:
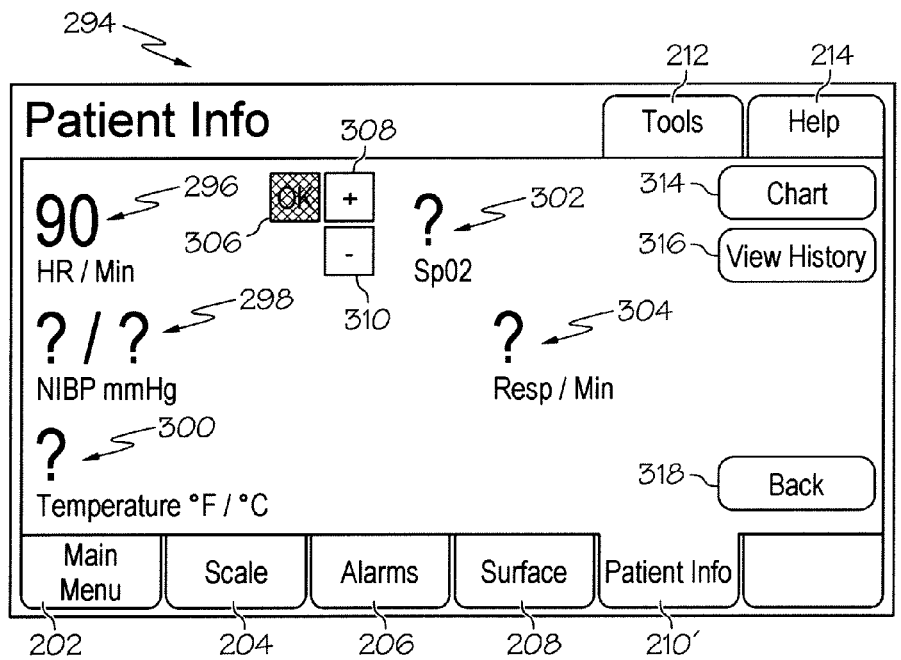
FIG. 15 is an example of the Patient Info screen in which the OK button is touched or pressed.
Figure 16:
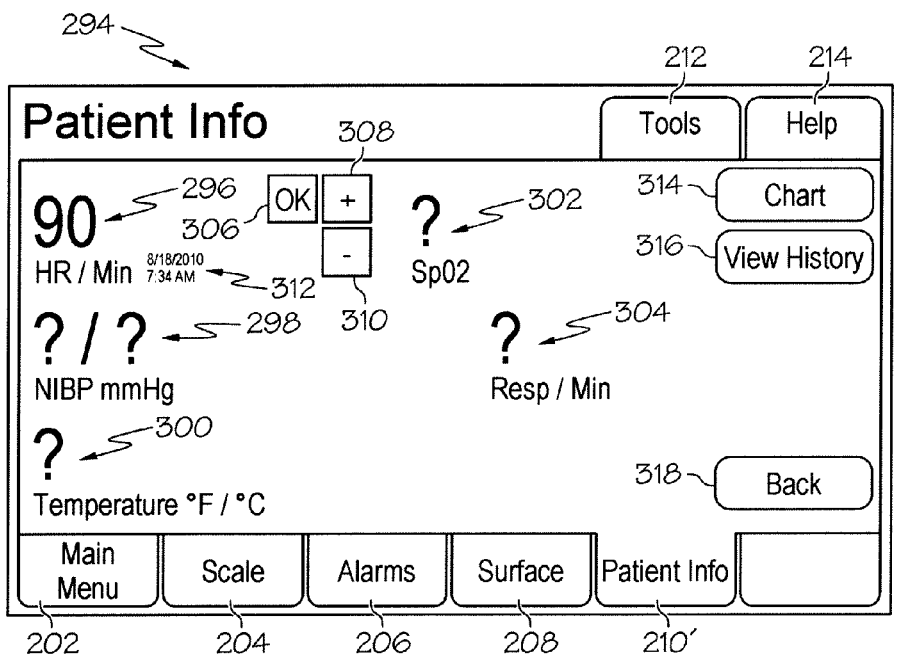
FIG. 16 is an example of the Patient Info screen after the OK button is released, a date stamp and time stamp being shown on the Patient Info screen adjacent the heart rate information in response to the OK field being pressed and released.
Figure 17:
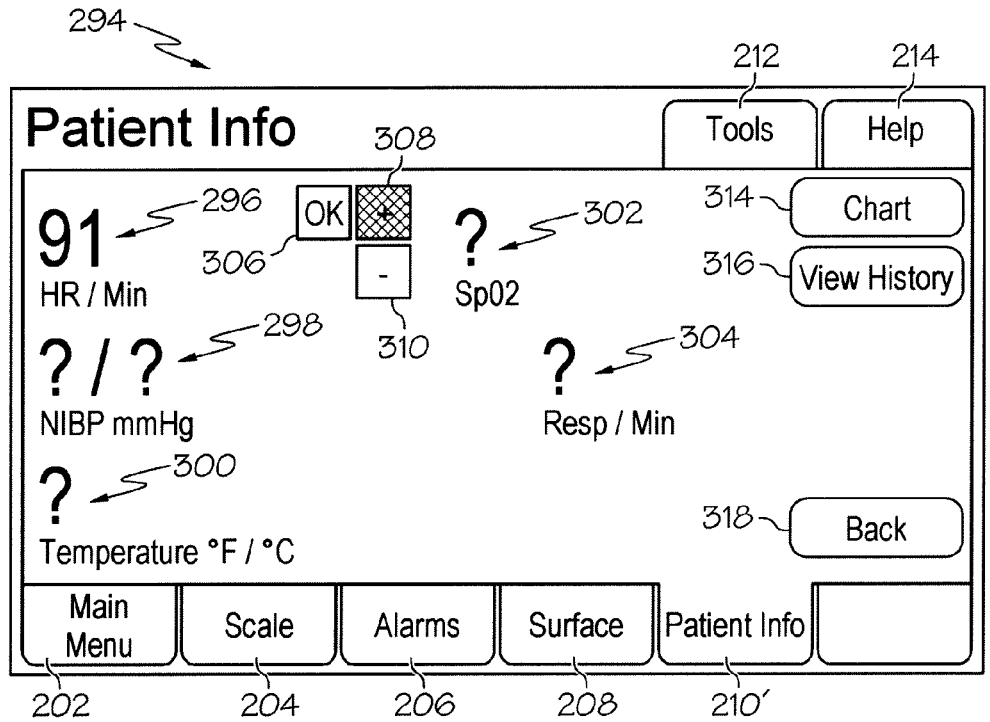
FIG. 17 is an example of the Patient Info screen in which the plus button is touched or pressed.

If the patient's heart rate is still 90 beats per minute, then the caregiver presses or touches the OK icon 306 at which point the OK icon 306 become highlighted, such as by changing color, as indicated by the cross hatching in FIG. 15, to provide the caregiver with visual feedback that icon 306 has been successfully pressed and then the caregiver stops pressing or touching icon 306. After the caregiver releases icon 306, the highlighting from icon 306 disappears and a date and time stamp 312 appears adjacent to field 296 to indicate the date and time that the particular patient data, the heart rate in this instance, was measured.

Figure 18:
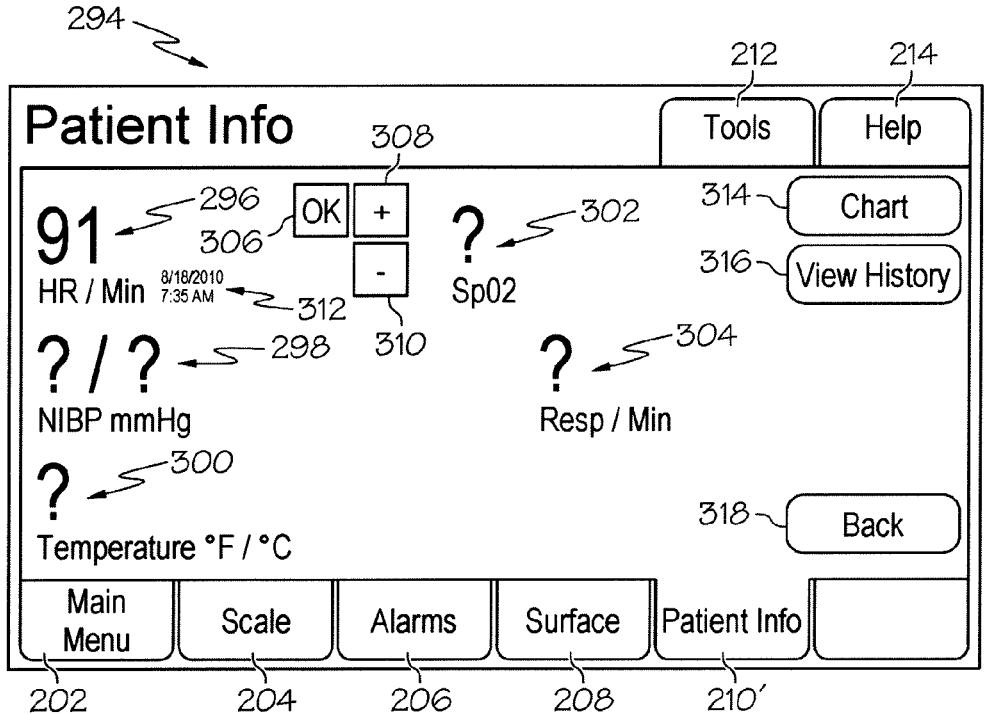
FIG. 18 is an example of the Patient Info screen after the plus button is released, the heart rate information being increased by one beat per minute in response to the plus field being pressed and released.
Figure 19:
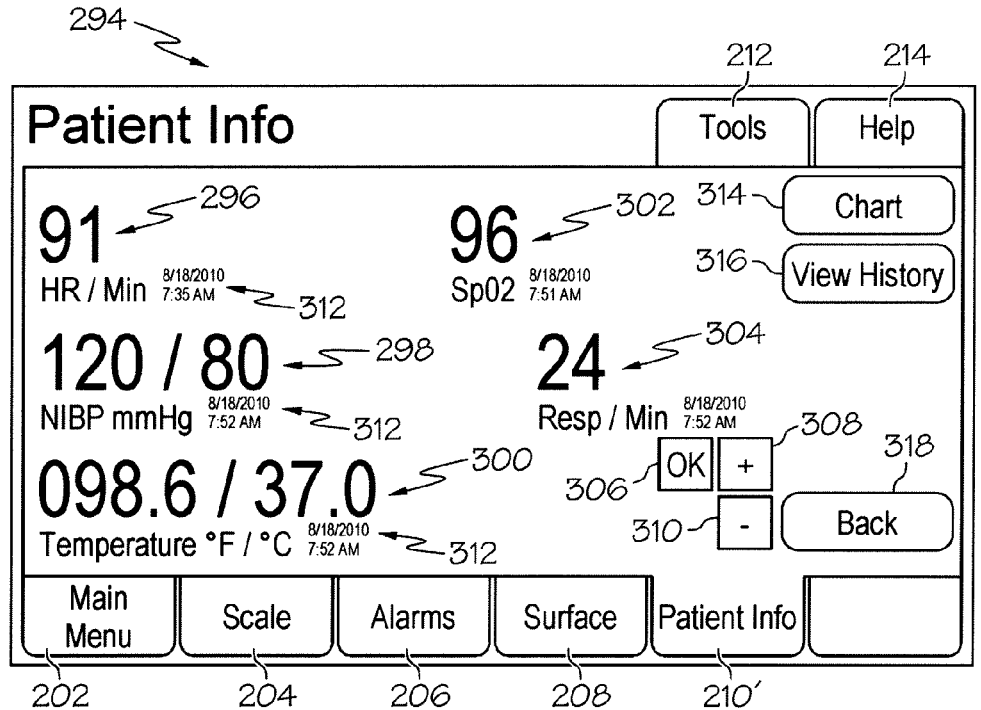
FIG. 19 is an example of the Patient Info screen after patient information has been manually entered into all of the available fields once occupied by the question marks of FIG. 13.

If the patient's heart rate is no longer 90 beats per minute and the caregiver wishes to change the heart rate data value, the plus icon 308 or the minus icon 310 are pressed by the caregiver to increase or decrease, respectively, the data value. For example, if the caregiver touches the plus icon 308, the plus icon 308 becomes highlighted, such as by changing color, as indicated by the cross hatching in FIG. 17, to provide the caregiver with visual feedback that icon 308 has been successfully pressed and the heart rate is then increased. To increase the heart rate data by additional integers, the caregiver simply continues pressing or touching icon 308 while the data value increments. Once the data value reaches the desired value, the caregiver stops pressing or touching icon 308. After the caregiver releases icon 308, the highlighting from icon 308 disappears and the associated date and time stamp 312 appears adjacent to field 296 to indicate the date and time that the particular patient data, the heart rate in this instance, was measured as shown in FIG. 18. The minus icon 310 works in a similar fashion to decrement the data value.

The same process is used by the caregiver to enter and change the data values in each of fields 298, 300, 302, 304. If desired, the caregiver can leave one or more of fields 296, 298, 300, 302, 304 blank if the associated data is not available or is not being monitored for the particular patient. In the example shown in FIG. 19, each of fields 296, 298, 300, 302, 304 has had data manually entered by the caregiver and there is a date and time stamp 312 adjacent to each field 296, 298, 300, 302, 304. It should be noted that, if one of fields 296, 298, 300, 302, 304 is selected by the caregiver to replace the associated question mark with a default value or previously charted value, but then the caregiver does not subsequently touch the OK icon 306 or use the plus or minus icons 308, 310 to change the value within a threshold period of time (e.g., 2 to 15 seconds), the value shown in the corresponding field 296, 298, 300, 302, 304 will disappear and the question mark will reappear in the corresponding field 296, 298, 300, 302, 304.

In the illustrative example, patient data corresponding to heart rate in beats per minute (HR/Min), blood pressure in millimeters of Mercury (mmHg), temperature in both degrees Fahrenheit and degrees Celsius (° F./° C.), pulse oximetry as a percentage of saturation of peripheral oxygen (SpO2) which corresponds to a percentage saturation of hemoglobin with oxygen, and respiration rate in breaths per minute (Resp/Min) can be entered manually on Patient Info screen 294. In other embodiments, other types of patient data can be entered manually on screen 294 in addition to or in lieu of the data discussed above. Invasive blood pressure and patient height are examples of another type of patient data. It should also be noted that use of other units of measure for the entered data is within the scope of this disclosure.

As shown in FIGS. 13-19, Patient Info screen 294 includes a Chart button or icon 314, a View History button or icon 316, and a Back button or icon 318. After one or more of fields 296, 298, 300, 302, 304 are populated with the relevant patient data, the caregiver presses Chart icon 314 and the Chart data screen or window 278 shown in FIG. 11 appears on the graphical user interface 142. The caregiver then selects the Yes icon 282 on screen 278 to send the patient data shown on screen 294 to the EMR system 176 for charting in the patient's medical record. If the caregiver does not wish to chart the data to the EMR system 176, then the caregiver selects the No icon 284 of screen 278 to return to screen 294 without the patient data being sent to the EMR system 176.

If the caregiver selects the Back button 318 on screen 294, then Charting Home screen 240, an example of which is shown in FIG. 5, appears on graphical user interface 142. In response to the caregiver selecting the Chart icon 314 on screen 294 and then Yes icon 282 on screen 278, a Patient Info History screen 320 appears on the graphical user interface 142 as shown, for example, in FIG. 20. Patient Info History screen 320 has a left scroll arrow 322 and right scroll arrow 324 that are selected to scroll through patient data that has been charted to the EMR system for the particular patient. The left scroll arrow 322 is selected to scroll back in time and the right scroll arrow 324 is used to scroll forward in time. As the scroll arrows 322, 324 are used to retrieve data charted to the EMR system 176 at different times, fields 296, 298, 300, 302, 304 are populated with the charted data and a date and time stamp 326 is shown in the area between arrows 322, 324 to indicate the date and time at which the associated data was charted to the EMR system 176.

Figure 20:
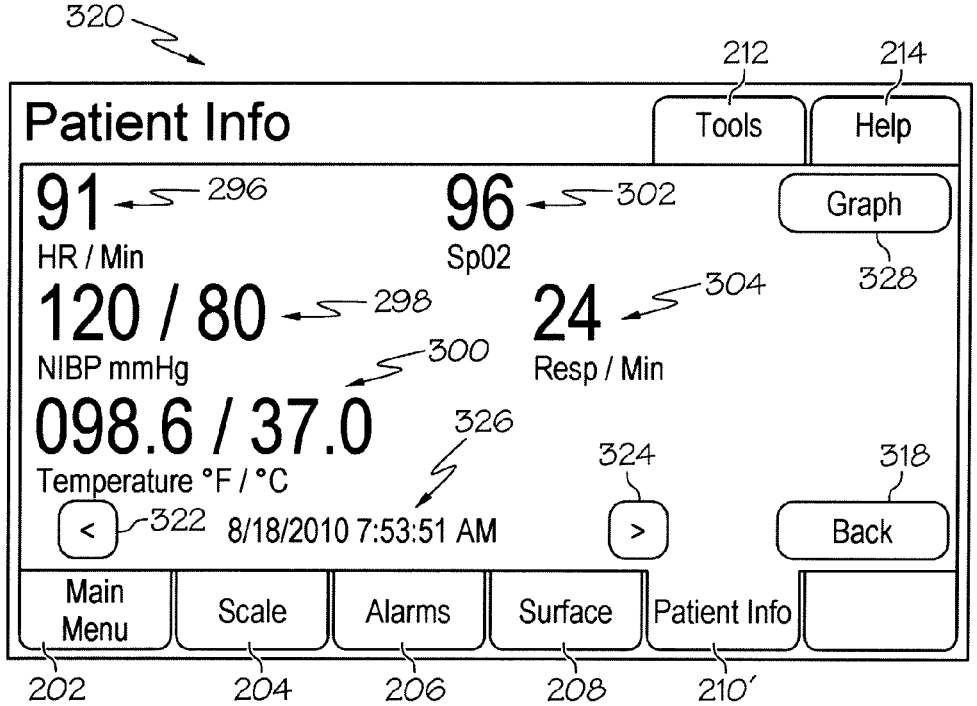
FIG. 20 is an example of a Patient Info History screen that appears on the graphical user interface after a Chart button, shown in FIG. 19, has been pressed and after pressing the yes button of a Charting Confirmation pop up window that is identical to the one shown in FIG. 11, the Patient Info History screen having left and right scroll arrows that are selected to scroll through patient data that has been charted to the EMR system for the particular patient.
Figure 21:
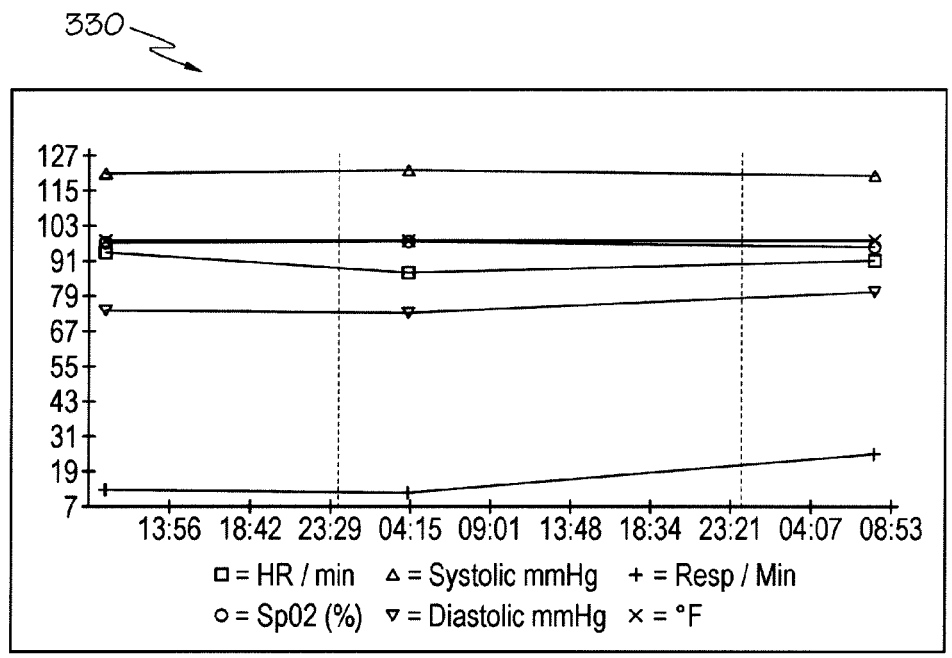
FIG. 21 is an example of a Patient Info History Graph screen that appears on the graphical user interface after a Graph button is touched on the Patient Info History screen, the Patient Info History Graph screen graphically representing the patient data stored in the EMR system at different times.

Patient Info History screen 320 includes a Graph button or icon 328 as shown in FIG. 20. In response to the caregiver selecting Graph button 328, a Patient Info History Graph screen 330, an example of which is shown in FIG. 21, appears on the graphical user interface 142. Patient Info History Graph screen 330 includes a graphical representation of the patient data stored in the EMR system at different times. In some embodiments, the caregiver double taps on screen 330 to return to the Patient Info History screen 320.

In other embodiments, a Close button or Back button is provided. Selection of the Back of Close icon returns the caregiver to the Patient Info History screen 320 and then Back button 318 is used on screen 320 to return the caregiver to the Charting Home screen 240 as mentioned above. In some embodiments, left and right scroll arrows are provided on screen 330 so that the caregiver is able to scroll to other portions of the patient info history graph if not all of the graph is able to fit on screen 330.

Figure 22:
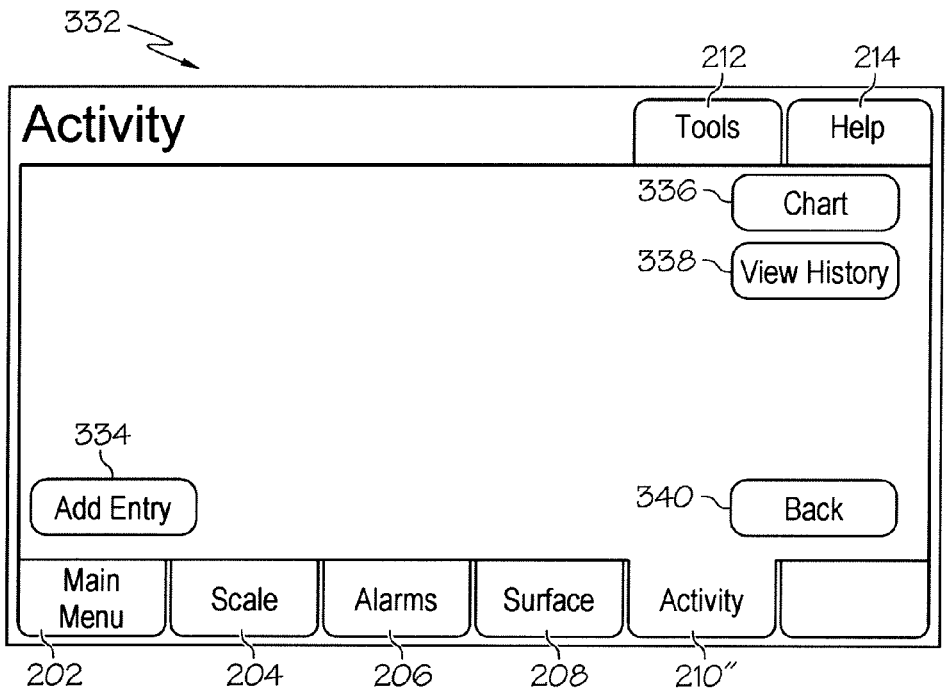
FIG. 22 is an example of an Activity screen that appears on the graphical user interface in response to the Activity icon being touched on the Charting Home screen and the Activity screen having an Add Entry button.

In response to the Activity icon 248 being selected on the Charting Home screen 240, an Activity screen 332 appears on the graphical user interface 142 as shown, for example in FIG. 22. When Activity screen 332 appears on interface 142, the Charting tab 210 changes its title from "Charting" to "Activity" and so is indicated as Activity tab 210". Activity screen 332 has an Add Entry button or icon 334, a Chart button or icon 336, a View History button or icon 338, and a Back button or icon 340.

Figure 23:
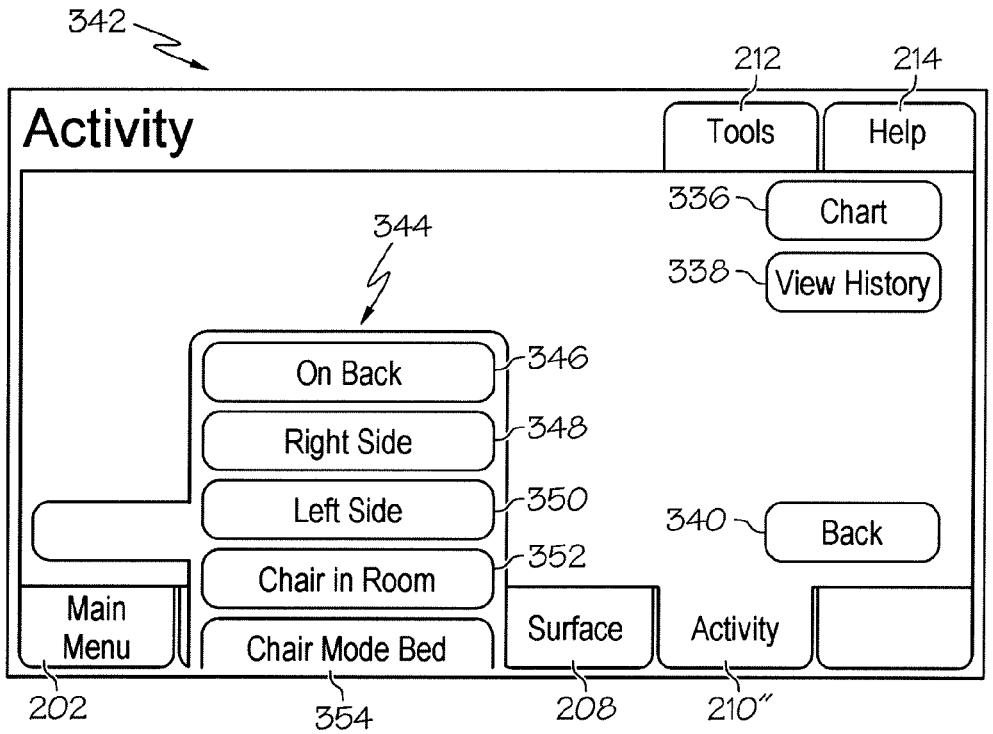
FIG. 23 is an example of an Activity Add Entry screen that appears on the graphical user interface in response to the Add Entry button being touched, the Activity Add Entry screen having a menu of activities including On Back, Right Side, Left Side, Chair in Room, and Chair Mode Bed fields or buttons.

If the caregiver selects Add Entry icon 334 on screen 332, an Activity Add Entry screen 342 appears on the graphical user interface 142 as shown, for example, in FIG. 23. The Activity Add Entry screen 342 has a menu 344 of activities in the form of selectable buttons or icons including On Back icon 346, Right Side icon 348, Left Side icon 350, Chair in Room icon 352, and Chair Mode Bed icon 354. On Back means that the patient has been turned onto their back, Right Side means that the patient has been turned on their right side, and Left Side means that the patient has been turned on their left side. Chair in Room means that the patient has been moved out of bed 10 and is sitting in a chair in the patient's room and Chair Mode Bed means that the bed has been moved into a chair position. Thus, in the illustrative example, the activities listed on menu 344 are mutually exclusive of each other. That is, the patient can only be doing one of those activities at a time. The description below of FIGS. 24-26 relates to selection of the On Back icon 346 from menu 344. However, a similar process is followed and a similar set of screens as those of FIGS. 24-26 result in response to selection of the other icons 348, 350, 352, 354 from menu 344 on screen 342.

Figure 24:
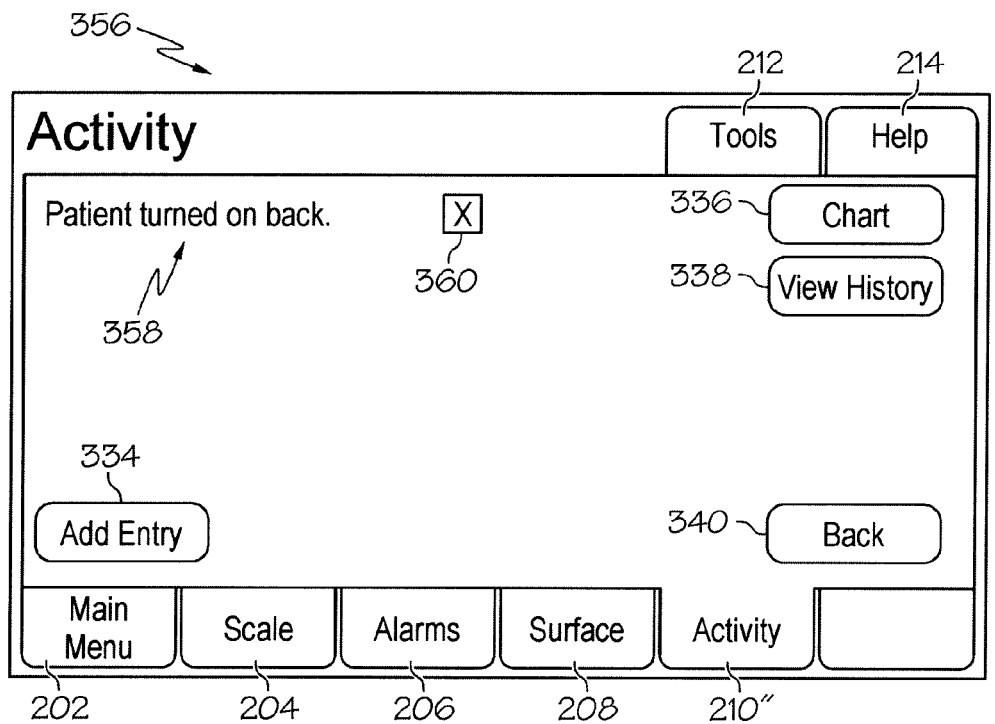
FIG. 24 is an example of an Activity On Back screen that appears on the graphical user interface in response to the On Back field of the Activity Add Entry screen being touched, the Activity On Back screen having a field containing the text "Patient turned on back" and an "x" icon.

In response to selection of On Back button 346 on menu 344 of screen 342, an Activity On Back screen 356 appears on the graphical user interface 142 as shown, for example, in FIG. 24. The Activity On Back screen 356 has a field 358 containing the text "Patient turned on back" and an "x" icon 360. At this point, the caregiver is able to select Chart icon 336 and the Chart Confirmation window 278 of FIG. 11 appears on interface 142. The caregiver then selects Yes icon 282 to chart the activity data to the patient's EMR in the EMR system 176 or selects the No icon 284 to return to screen 356 without charting the activity data. After the Yes icon 282 is selected on screen 278, Activity screen 332 once again appears on interface 142.

Figure 25:
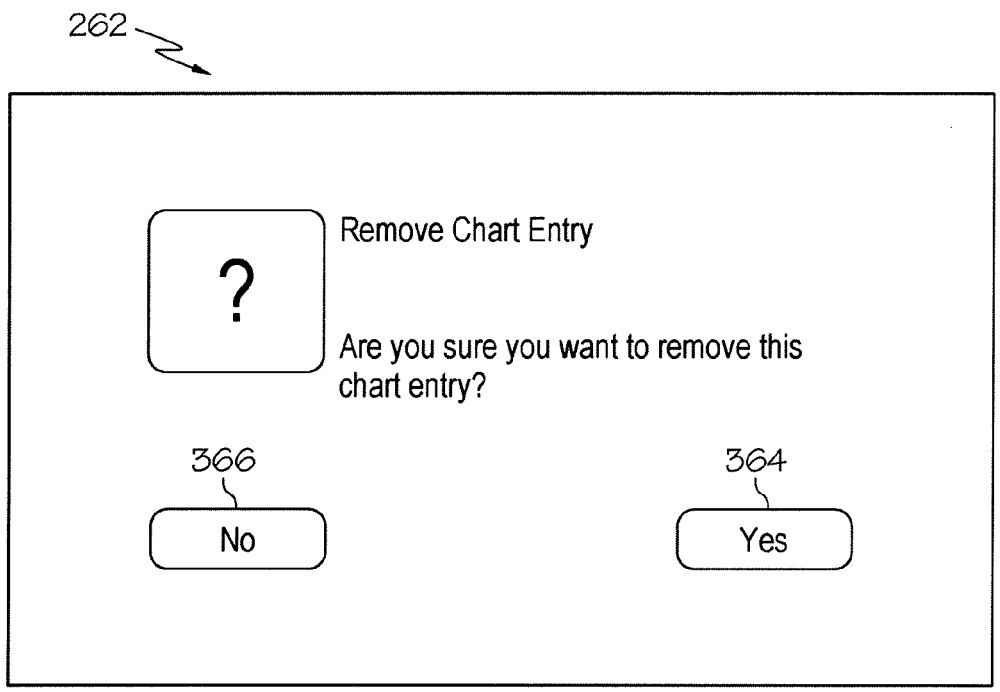
FIG. 25 is an example of an Activity Remove Entry screen that appears on the graphical user interface in response to the "x" icon being touched on the Activity On Back screen, the Activity Remove Entry screen having Yes and No fields or buttons that are selected depending upon whether or not the activity is to be removed.

While viewing screen 356, if the caregiver wishes to remove the activity without charting it to the patient's EMR, the caregiver selects the "x" icon 360 which results in an Activity Remove Entry screen 362 appearing on the graphical user interface 142 as shown in FIG. 25. The Activity Remove Entry screen 362 has a Yes icon or button 364 and a No icon or button 366 along with the text "Are you sure you want to remove this chart entry?" If the caregiver selects the No icon 366 on screen 362, the caregiver returns to screen 356 of FIG. 24. If the caregiver selects the Yes icon 364 on screen 362, then activity appearing on screen 356 is erased and the caregiver is returned to screen 332 of FIG. 22.

Figure 26:
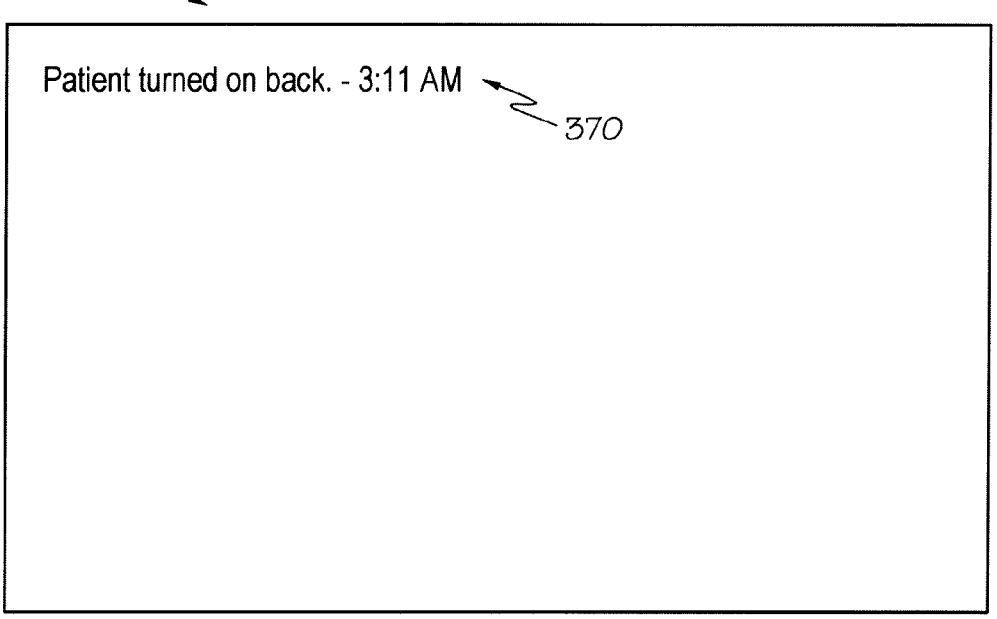
FIG. 26 is an example of an Activity View History screen that appears on the graphical user interface after a Chart button has been touched on the Activity On Back screen of FIG. 24, after the Yes button has been touched on the resulting Charting Confirmation pop up window, and after a View History button or field has been touched on the Activity screen of FIG. 22.

If the caregiver selects the View History icon 338 on screen 332, for example, an Activity View History screen 368 appears on the graphical user interface 142 as shown, for example, in FIG. 26. In the illustrative example, a line of text 370 stating "Patient turned on back.—3:11 AM" appears on screen 368. If additional activities had been charted to the EMR system 176 for the associated patient in the past, then additional lines of text, similar to text 370 would also be shown on screen 368. If so many activities had been charted for the patient that all of the lines of text could not fit on screen 368, then Up and Down scroll arrows are provided, in some embodiments, to permit the caregiver to scroll to the other activities entries.

Figure 27:
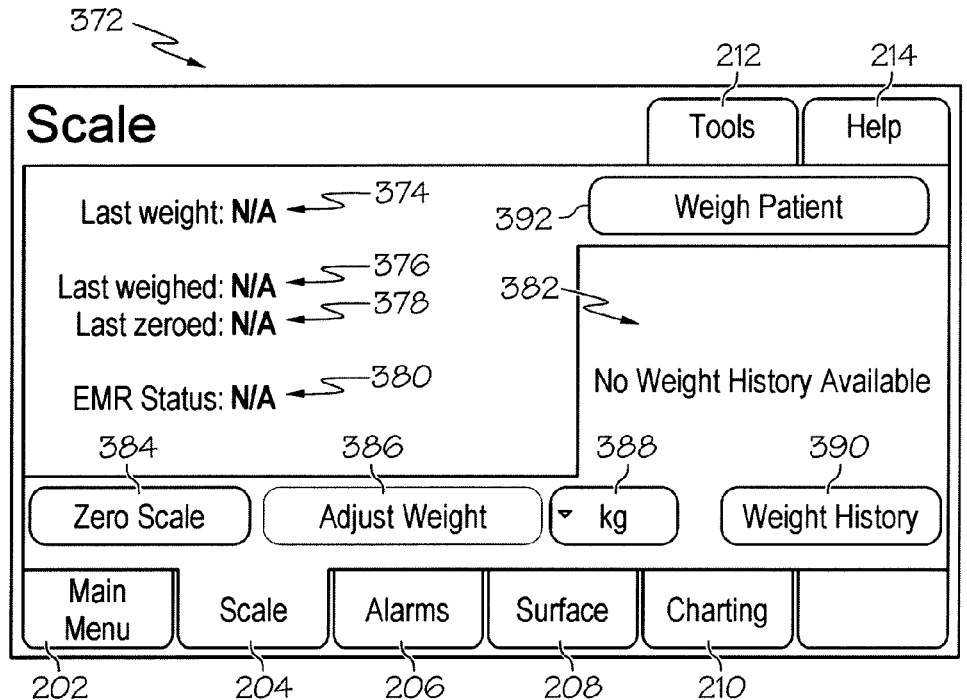
FIG. 27 is an example of a Scale screen that appears on the graphical user interface in response to the user touching a Scale tab.

Referring now to FIG. 27, if the scale tab 204 is selected, a Scale screen 372 appears on the graphical user interface 142. Screen 372 includes a Last Weight field 374, a Last Weighed field 376, a Last Zeroed field 378, an EMR Status field 380, and a Weight History Graph field 382. In the illustrative example of screen 372, each of fields 374, 376, 378, 380 has N/A to indicate that the patient has not yet been weighed and therefore, no data is available for those fields and field 382 does not have a weight graph since the patient has not yet been weighed.

Screen 372 also has a Zero Scale button or icon 384, an Adjust weight button or icon 386, a kg button or icon 388, a Weight History button or icon 390, and a Weigh Patient button or icon 392. The Zero Scale button 384 is used to set the tare weight of the scale system 270. The Adjust Weight button 386 is used to adjust the patient's weight reading up or down using plus and minus keys that appear on interface 142 after button 386 is selected. The kg button 388 is used to indicate whether the caregiver wishes to display the patient's weight in kilograms (kg) or pounds (lb). If button 388 is pressed, the scale system 270 switches to pounds units and the units "lb" appear in button 388 to indicate that the weight units are being display in lbs. The Weight History button 390 is pressed to cause a weight graph to appear in field 382.

Figure 28:
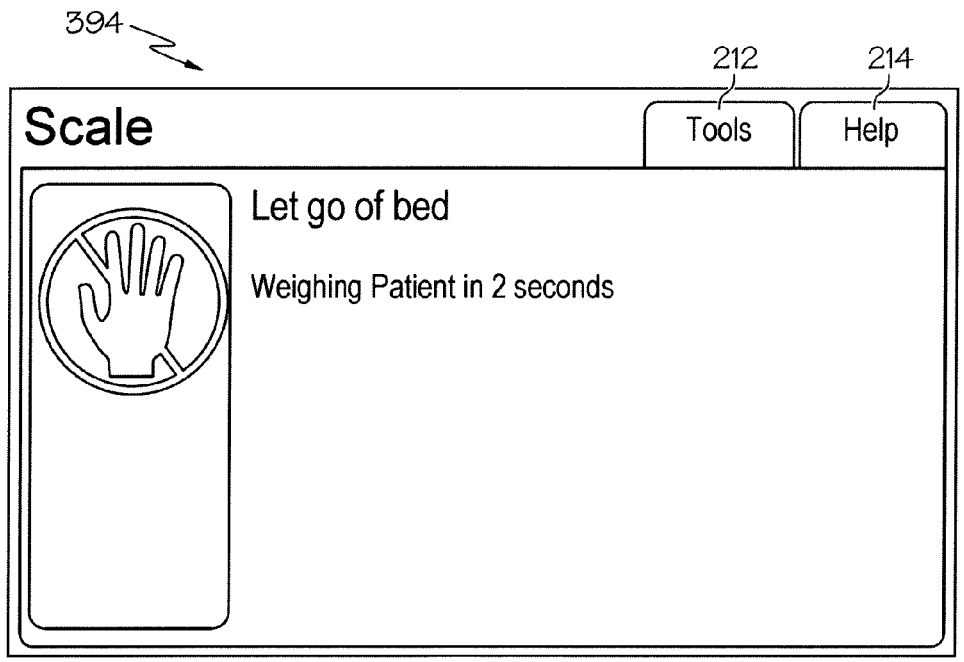
FIG. 28 is a Scale Let Go screen that appears on the graphical user interface for a threshold amount of time after the user touches a Weigh Patient button or field on the Scale screen of FIG. 27.
Figure 29:
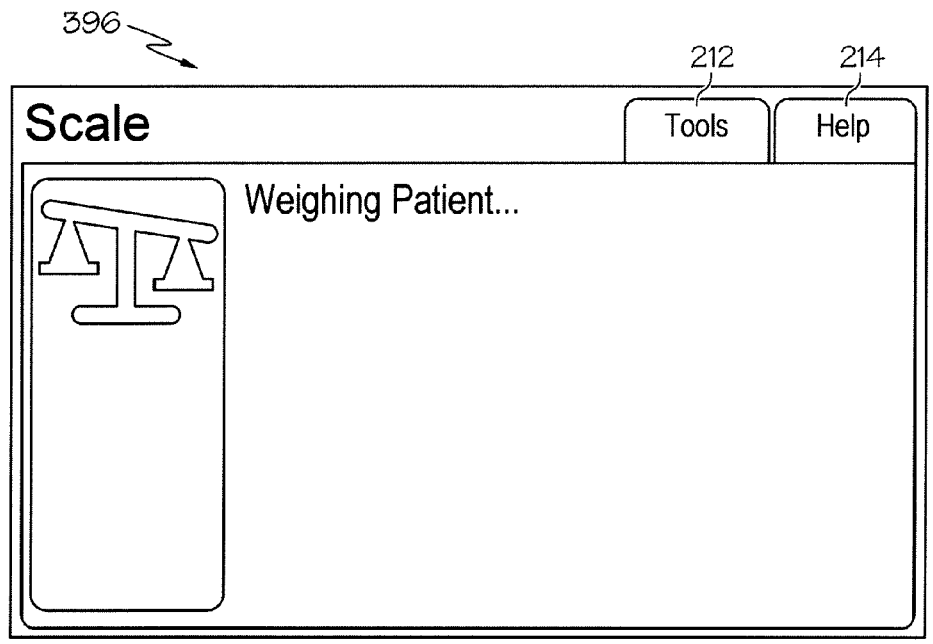
FIG. 29 is an example of a Scale Weighing screen that appears on the graphical user interface while a scale system of the hospital bed weighs the patient.

If the caregiver selects the Weigh Patient button 392 on screen 372, a Scale Let Go screen 394, shown in FIG. 28, appears on the graphical user interface 142 for a threshold amount of time, such as three seconds in the illustrative example. Screen 394 has the text "Let go of bed" and "Weighing Patient in 2 seconds." Thus, in the illustrative embodiment, the text on screen 394 counts down in one second increments from the three second threshold. After the threshold amount of time, a Scale Weighing screen 396 appears on the graphical user interface 142 as shown in FIG. 29. Screen 396 is shown on interface 142 while scale system 270 of hospital bed 10 weighs the patient.

Figure 30:
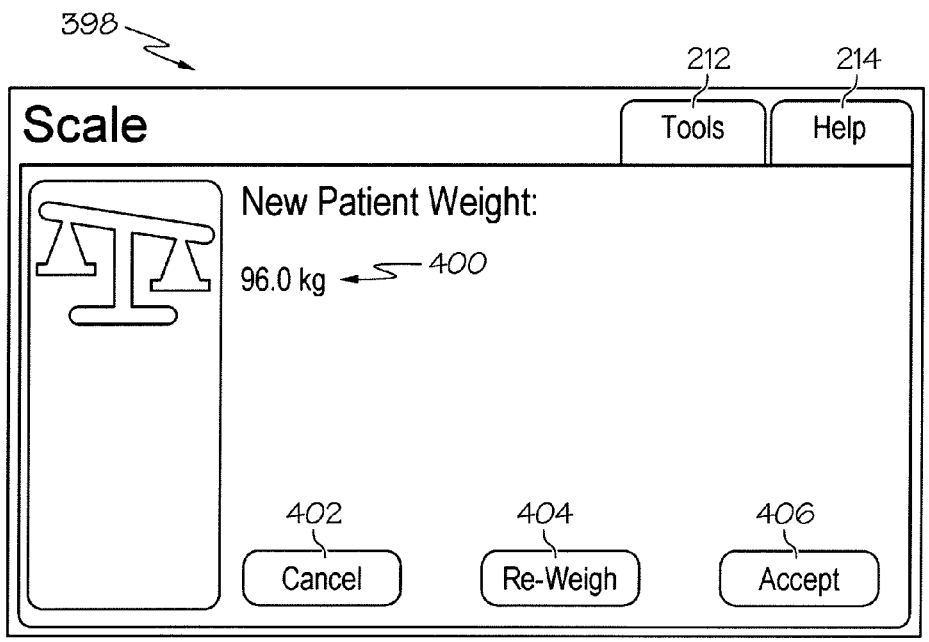
FIG. 30 is an example of a Scale Accept screen that appears on the graphical user interface after the patient has been weighed, the patient's weight being displayed on the Scale Accept screen.

After scale system 270 has weighed the patient, a Scale Accept screen 398 appears on the graphical user interface 142 as shown, for example, in FIG. 30. Scale Accept screen 398 has a New Patient Weight field 400 in which the measured patient weight is displayed. In the illustrative example, the patient's weight is 96.0 kg. Screen 398 also has a Cancel button or icon 402, a Re-Weigh button or icon 404, and an Accept button or icon 406. Cancel button 402 is selected to cancel the weight reading that has just been taken. Re-Weigh button 404 is selected if the caregiver wishes to re-weigh the patient for some reason, such as the bed being bumped or the patient moving at the time during which the previous weight reading was being taken.

The Accept button 406 is pressed to accept the weight after the patient has been weighed. Depending upon whether an EMR Autosend feature is enabled or disabled, as will be discussed below in connection with FIGS. 31-34, the selection of Accept 406 either stores the patient weight in memory 174 of control circuitry 98 and initiates the charting of the weight reading to the EMR system 176 (if the EMR Autosend feature is enabled) or stores the patient weight in memory 174 of control circuitry 98 and does not initiate the charting of the weight reading to the EMR system 176 (if the EMR Autosend feature is disabled).

Figure 31:
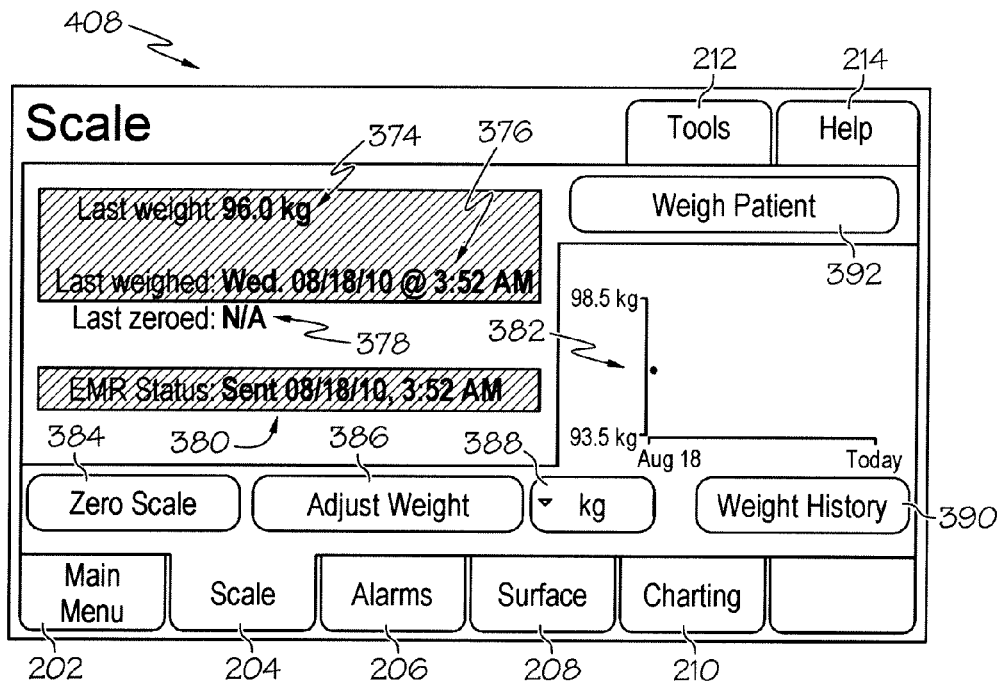
FIG. 31 is an example of a Scale Yellow screen that appears on the graphical user interface after an Accept button of the Scale Accept screen of FIG. 30 is touched if an EMR Autosend feature of the hospital bed is enabled and that appears on the graphical user interface after the Accept button is pressed and after the Yes button has been touched on the resulting Charting Confirmation pop up window which appears if the EMR Autosend feature is disabled, the Scale Yellow screen having a number of fields highlighted yellow to indicate the information that has been charted to the patient's EMR.
Figure 32:
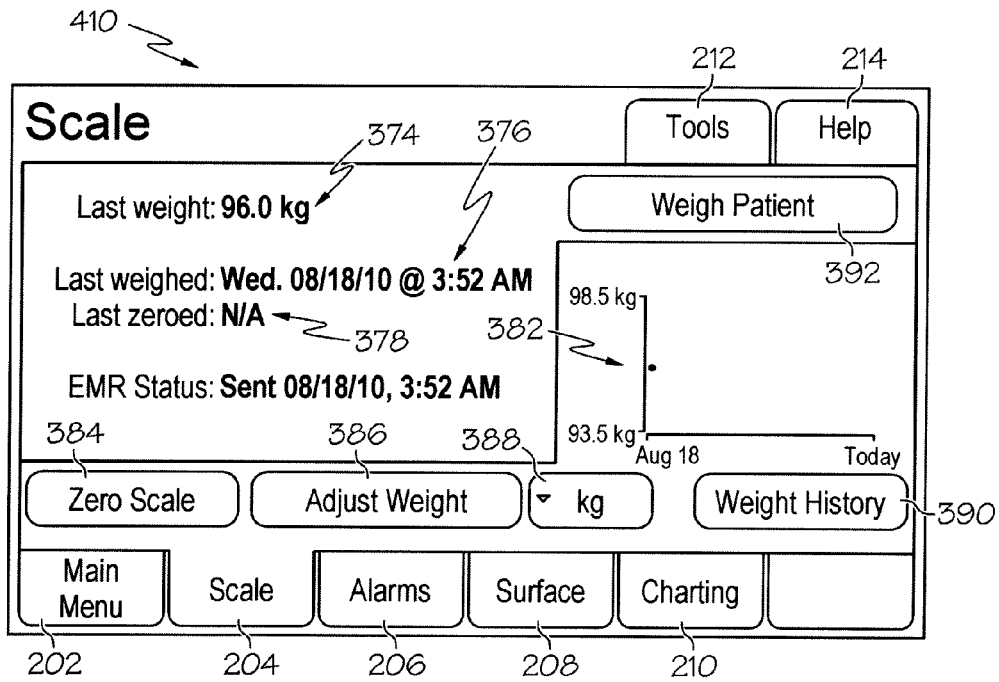
FIG. 32 is an example of a Scale Final screen that appears on the graphical user interface after a threshold amount of time during which the yellow highlighting of the Scale Yellow screen fades.

If the EMR Autosend feature is disabled, then after selection of the Accept button 406 on screen 398, a Scale Yellow screen 408 appears on the graphical user interface 142 as shown, for example, in FIG. 31. If the EMR Autosend feature is enabled, then after the Accept button 406 is selected and the Chart Confirmation window 278 of FIG. 11 appears on the graphical user interface 142. Selection of the Yes button 282 on window 278 results in the Scale Yellow screen 408 appearing on interface 142 and the patient's weight is sent to the EMR system 176 for charting in the patient's EMR as mentioned above. Screen 408 has fields 374, 376, 380 highlighted yellow, as indicated by the cross hatching in FIG. 31, to indicate the new information that is being stored in memory 174 of bed 10 and, if the EMR Autosend feature is enabled, is also being charted to the patient's EMR. During a threshold amount of time, such as three seconds in the illustrative example, the yellow highlighting of fields 374, 376, 380 fades at which point a Scale Final screen 410 appears on the graphical user interface 142 as shown, for example in FIG. 32.

On screens 408, 410, field 382 shows a graph including the patient's current weight. If the patient had been weighed multiple times, then additional data points would appear on the graph in field 382. In the illustrative example, the text "Sent 08/18/10, 3:52 AM" appears in field 380 to indicate the date and time at which the patient's weight was charted in the EMR system 176. Thus, the EMR Autosend feature is enabled in the illustrative example. If the EMR Autosend feature were disabled, then the text N/A would have remained in field 380 on screens 408, 410.

Figure 33:
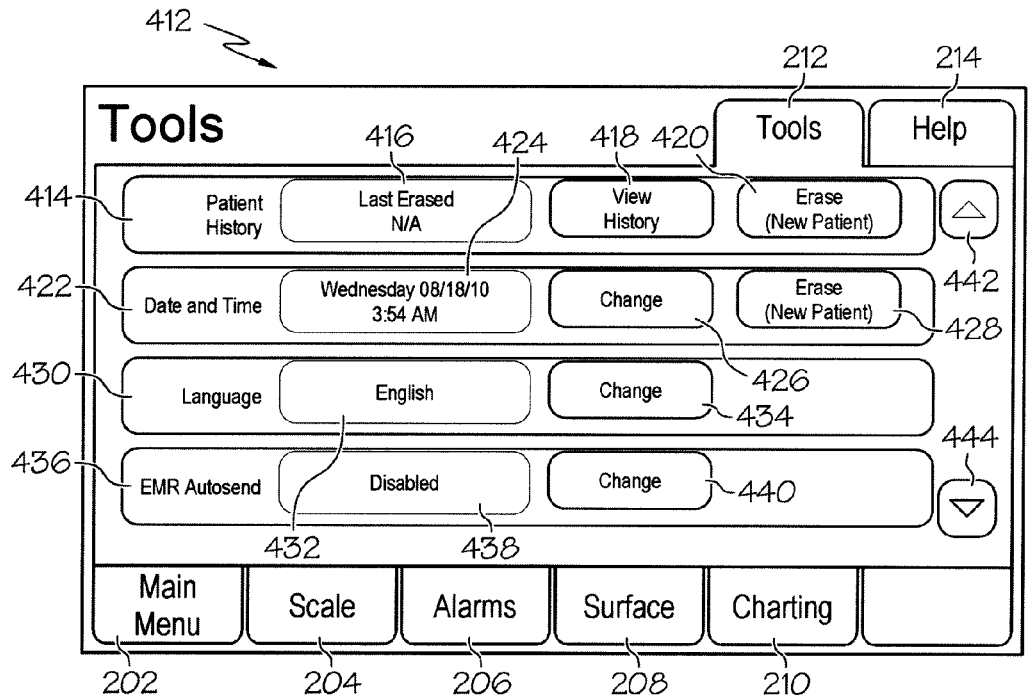
FIG. 33 is a Tools Autosend Disabled screen that appears on the graphical user interface in response to a Tools tab being touched if the Autosend feature of the hospital bed is disabled.
Figure 34:
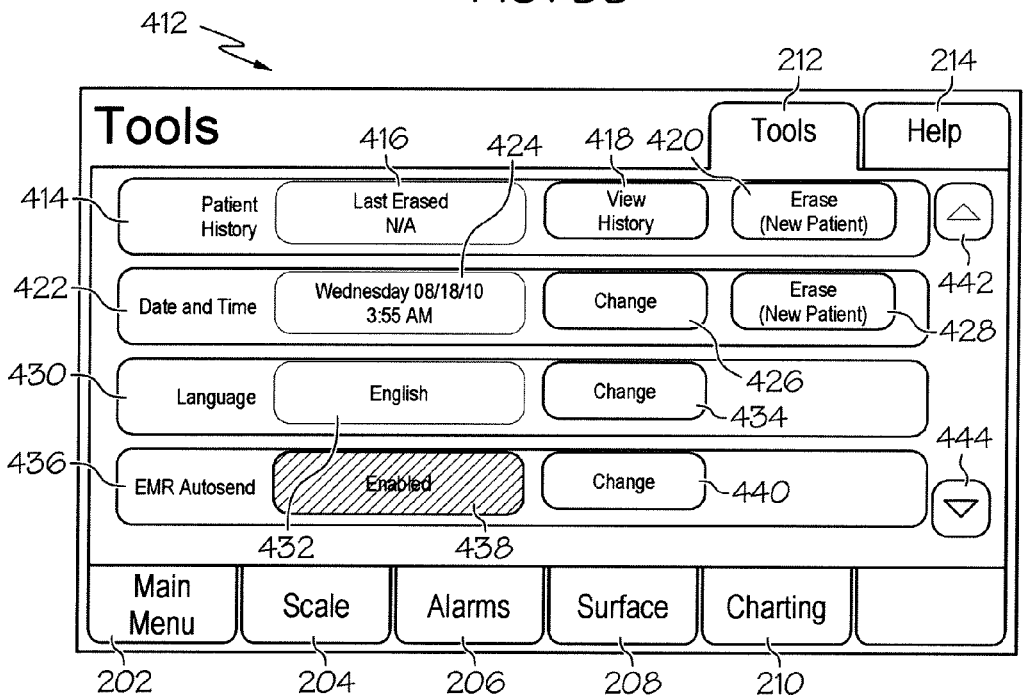
FIG. 34 is a Tools Autosend Switch to Enabled screen that appears on the graphical user interface in response to a Change button or field associated with the Autosend feature being touched on the Tools Autosend Disabled screen of FIG. 33, a Disabled field changing to an Enabled field and being highlighted yellow after the Change button of the Tools Autosend Disabled screen of FIG. 33 is touched.

Referring now to FIG. 33, if Tools tab 212 is selected when the EMR Autosend feature is disabled, a Tools Autosend Disabled screen 412 appears on the graphical user interface 142. Screen 412 includes a Patient History bar 414 with a Last Erased field 416, a View History icon or button 418, and an Erase (New Patient) button or icon 420. Button 420 is selected, in some embodiments, to erase the data stored in memory 174 of bed 10 for a previous patient so that only new data associated with a new patient is shown on the various screens discussed herein on the graphical user interface 142. In other embodiments, memory 174 still stores the data from previous patients, it just is not shown on interface 142 once a new patient has been assigned to bed 10. Button 418 is selected to view the history information associated with the patient assigned to bed 10. The last erased field 416 indicates the date and time at which the patient history data was last erased.

Screen 412 also includes a Date and Time bar 422 that includes a Date and Time field 424, a Change button or icon 426, and an Erase (New Patient) button or icon 428. Button 428 is selected to erase the date and time information for the previous patient. Field 424 shows the current date and time. Change button 426 is used to change the date and time, for example, if the date and time shown in field 424 is inaccurate. Selection of change button 426 results in keys being displayed for changing the date and time.

Screen 412 further has a Language bar 430 that includes a Language field 432 and a Change icon or button 434. The word "English" appears in the Language field 432 in the illustrative example. Button 434 is selected to change the language of the various screens that appear on graphical user interface 142. Selection of button 434 results in a menu of language options being displayed on interface 142 and the caregiver can then select the desired language on the menu of language options.

Figure 35:
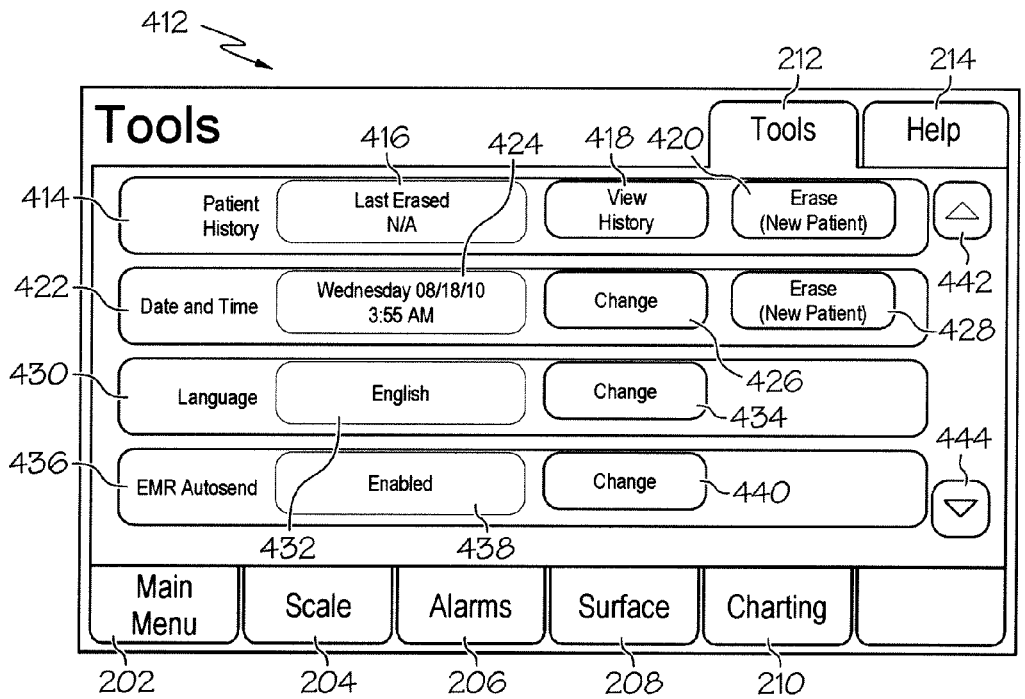
FIG. 35 is a Tools Autosend Enabled screen that appears on the graphical user interface after a threshold amount of time during which the yellow highlighting of the Enabled field fades.
Figure 36:
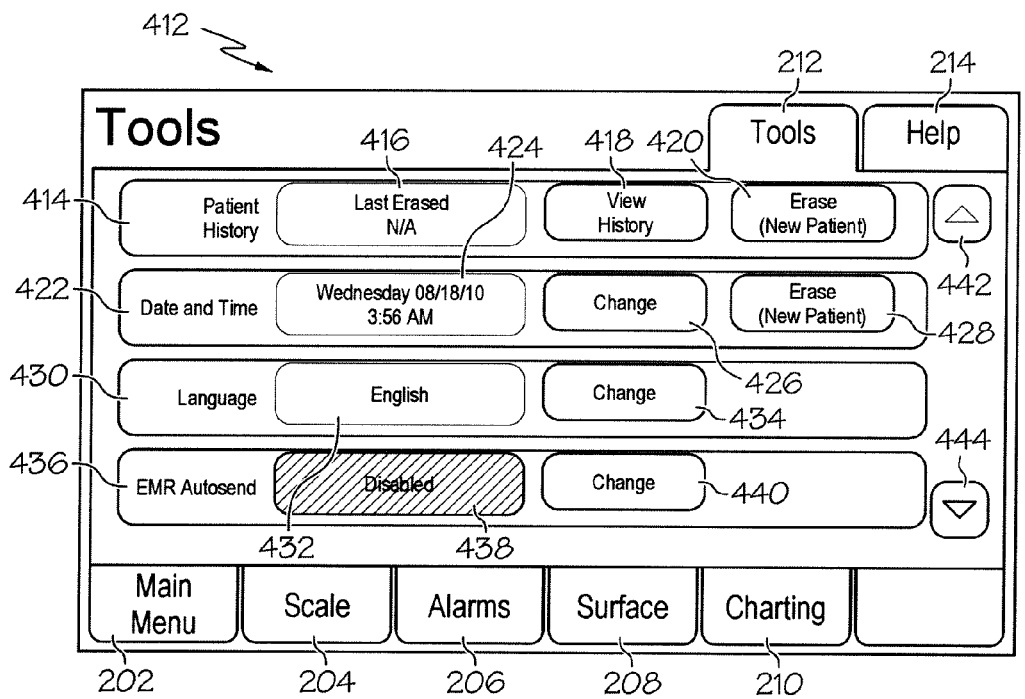
FIG. 36 is a Tools Autosend Switch to Disabled screen that appears on the graphical user interface in response to the Change button or field associated with the Autosend feature being touched on the Tools Autosend Enabled screen of FIG. 35, the Enabled field changing back to the Disabled field and being highlighted yellow after the Change button of the Tools Autosend Enabled screen of FIG. 35 is touched.

Screen 412 has an EMR Autosend bar 436 that includes an Enabled/Disabled field 438 and a Change button or icon 440. The word "Disabled" appears in field 438 to indicate that the EMR Autosend feature of bed 10 is disabled. If the caregiver touches button 440 on screen 412 of FIG. 33, field 438 becomes highlighted, such as yellow highlighting, as indicated by the cross hatching in FIG. 34 and the word "Disabled" changes to "Enabled" to indicate that the EMR Autosend feature of bed 10 is enabled. After a threshold period of time, such as three seconds, for example, the highlighting fades and disappears as shown in FIG. 35. If the EMR Autosend feature is enabled and the caregiver wishes to disabled that feature, the caregiver touches button 440 and field 438 becomes highlighted, as indicated by the cross hatching in FIG. 36, and the word "Enabled" changes to "Disabled." The highlighting of field 438 in FIG. 36 fades and disappears after a threshold amount of time. Thus, button 440 is used to toggle the EMR Autosend feature between being enabled and being disabled and field 438 visually indicates whether or not the EMR Autosend feature is enabled or disabled.

Figure 37:
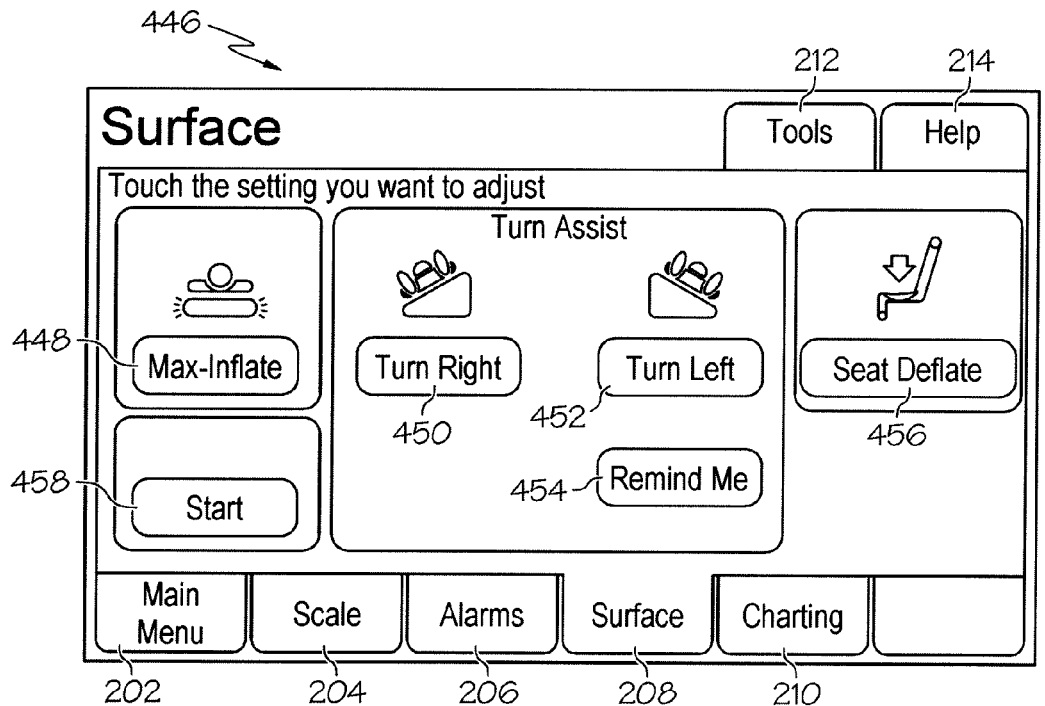
FIG. 37 is a Surface screen that appears on the graphical user interface in response to a Surface tab being selected, the Surface screen having user inputs that are touched to control various functions of a mattress of the hospital bed.
Figure 38:
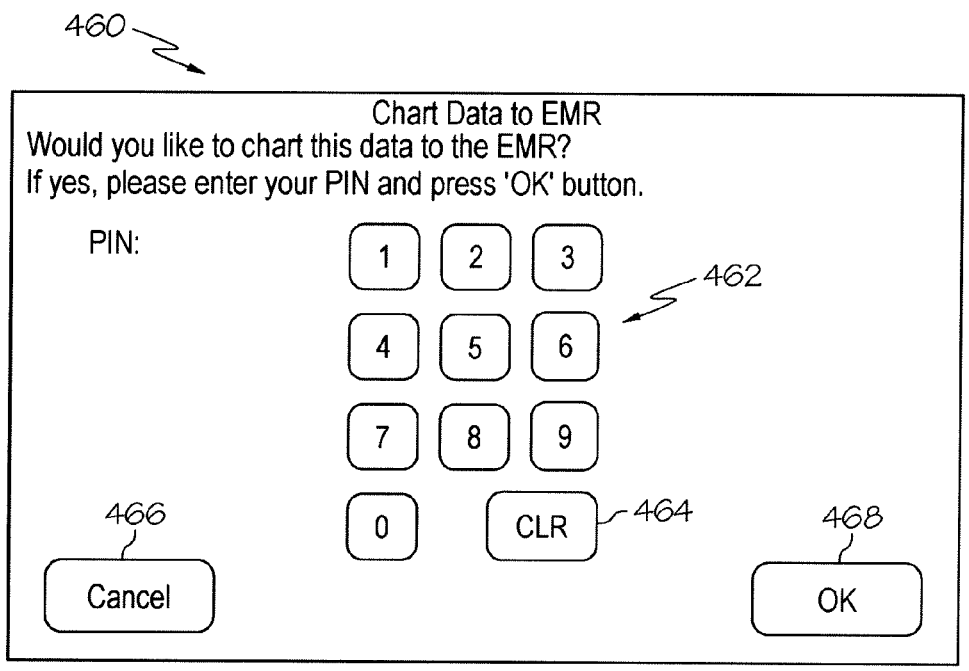
FIG. 38 is a Chart Data to EMR screen that appears on the graphical user interface in response to any of the user inputs of the Surface screen being touched.

Referring now to FIG. 37, a Surface screen 446 appears on the graphical user interface 142 in response to the Surface tab 208 being selected. Surface screen 446 has user inputs that are touched to control various functions of mattress 22 of hospital bed 10. In the illustrative example, screen 446 has a Max-Inflate button or icon 448 that is selected to inflate the bladders of the mattress 22 to their maximum programmed pressures, a Turn Right icon 450 that is selected to inflate a right turn bladder of mattress 22 to turn the patient onto their right side, a Turn Left button 452 that is selected to inflate a left turn bladder of mattress 22 to turn the patient onto their left side, a Remind Me icon or button 454 that is selected to set a timer for reminding the caregiver when to turn the patient, a Seat Deflate button or icon 456 that is selected to deflate bladders of mattress 22 in the seat section to facilitate easier side egress and ingress of the patient, and a Start button or icon 458 that is pressed to begin the function selected using icons 448, 450, 452, 456.

In response to one of buttons 448, 450, 452, 456 and then start button 458 being selected, a Chart Data to EMR screen 460 appears on the graphical user interface 142. In some embodiments, the Start button 458 is omitted such that the surface function associated with buttons 448, 450, 452, 456 begins in response to the respective button being selected. Chart Data to EMR screen 460 allows the caregiver to send information to the EMR for charting regarding use of the surface functions of mattress 22 for the patient. Screen 460 has a keyboard 462 in which the caregiver types his or her PIN and then an OK button 468 that is selected to chart the data to the EMR system 176. A Clear button 464, having the letters "CLR" therein, is provided in keyboard 462 and is selected if a mistake is made in entering the PIN. If the caregiver does not wish to chart the surface information to the EMR system 176, icon 466 is selected.

Figure 39:
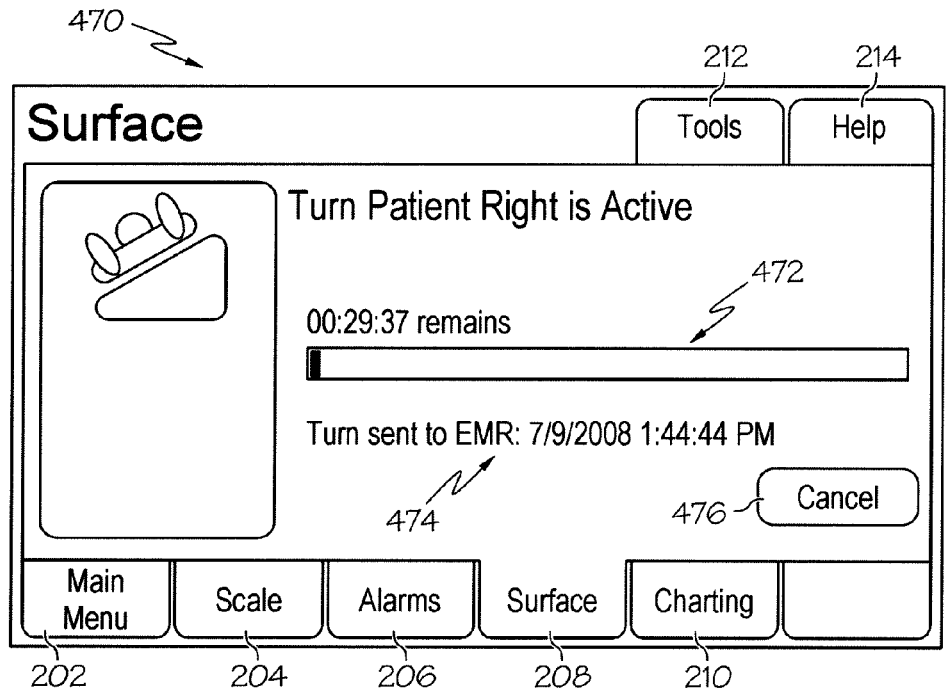
FIG. 39 is a first Turn Patient Right screen that appears on the graphical user interface in response to a PIN being entered and the OK button being touched on the Chart Data to EMR screen after a Turn Right button has been touched on the Surface screen, the first Turn Patient Right screen having a line of text confirming that turn data has been sent to the EMR for charting.

Referring to FIG. 39, a first Turn Patient Right screen 470 appears on the graphical user interface 142 in response to a valid PIN being entered and the OK button 468 being touched on the Chart Data to EMR screen 460 after Turn Right button 450 has been touched on the Surface screen. The first Turn Patient Right screen 470 has a line of text 474 stating "Turn sent to EMR: 7/9/2008 1:44:44 PM" to confirm that turn data has been sent to the EMR for charting. Screen 470 also has a countdown timer bar 472 that indicates how much time is left in the turn. In the illustrative example, 29 minutes, 37 seconds remains in the turn. Bar 472 fills in as time elapses during the turn.

Figure 40:
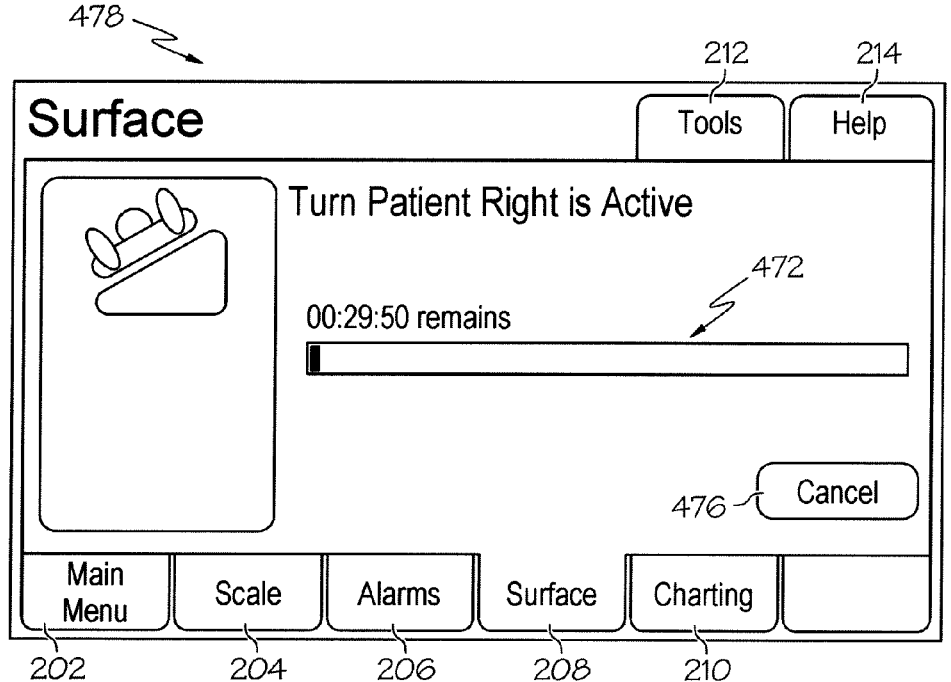
FIG. 40 is a second Turn Patient Right screen that appears on the graphical user interface in response to a Cancel button being touched on the Chart Data to EMR screen after the Turn Right button has been touched on the Surface screen.

As shown in FIG. 40, a second Turn Patient Right screen 478 appears on the graphical user interface 142 in response to Cancel button 466 being touched on the Chart Data to EMR screen 460 after the Turn Right button 450 has been touched on the Surface screen 446. Screen 478 is basically the same as screen 470 except that the line of text 474 appearing on screen 470 of FIG. 39 is omitted from screen 478 of FIG. 40. Each of screens 470, 478 has a Cancel button or icon 476 that is selected to cancel the turn before the full amount of time for the term has been reached. Screens substantially the same as screens 470, 478 appear on the graphical user interface 142 in response to Left Turn icon 452 being selected on screen 446 rather than Right Turn icon 450 being selected and after the desired selections are made on screen 460 of FIG. 38. Similar screens to screens 470, 478 are provided in response to use of icons 448, 456 on screen 446 and after desired selections are made on screen 460.

Figure 41:
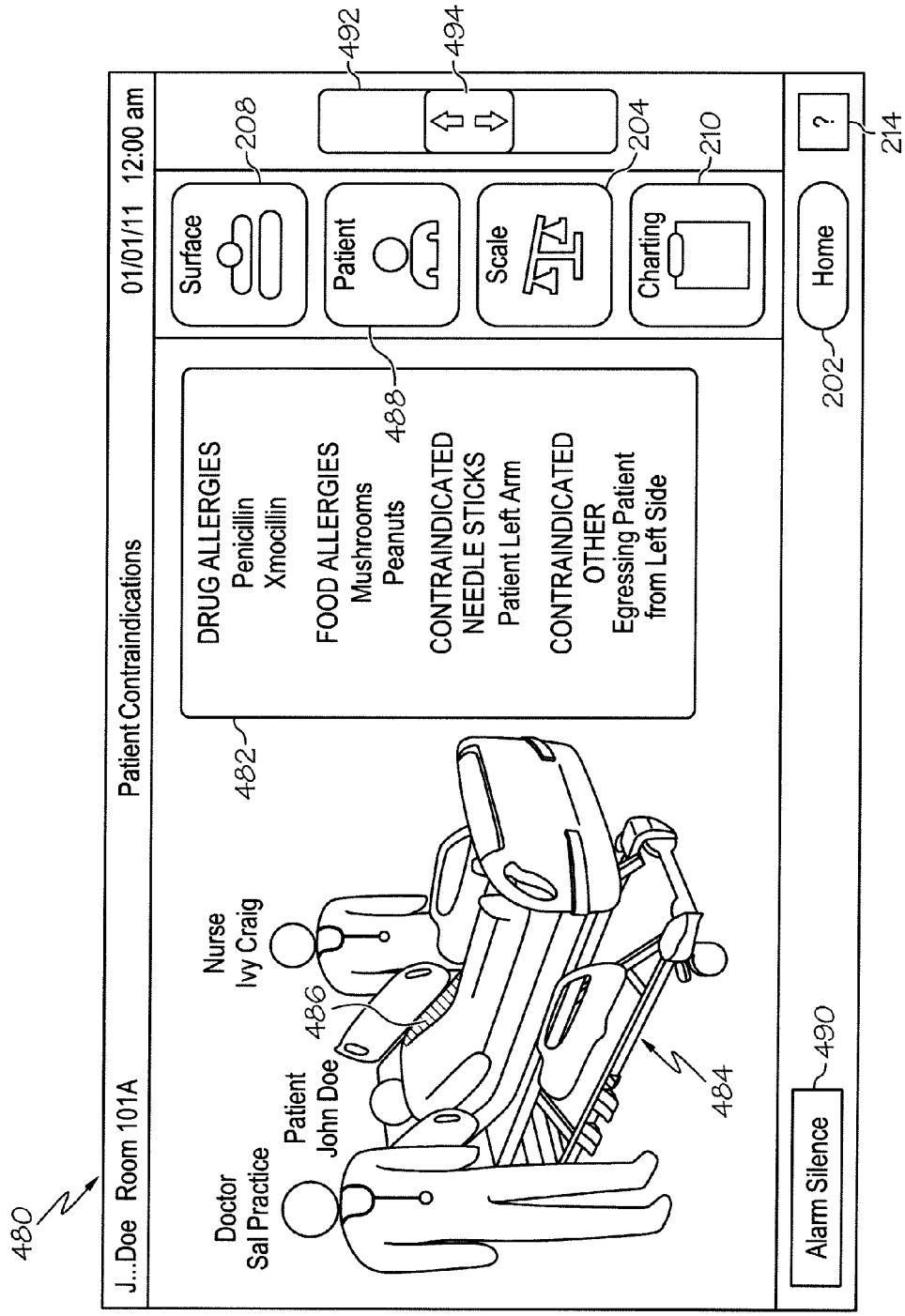
FIG. 41 is a Patient Contraindications screen that appears on the graphical user interface to show a list of a patient's drug and food allergies, to show that the patient is contraindicated for needle sticks in the left arm, and to show other contraindications for the patient.

Referring now to FIG. 41, a Patient Contraindications screen 480 is another example of a screen that appears on the graphical user interface 142 in some embodiments. Screen 480 includes a contraindications window 482 in which a list of a patient's drug and food allergies, a patient's needle sticks contraindications, and other contraindications for the patient appears. In the illustrative example, window 482 indicates that the associated patient has drug allergies of penicillin and xmocillin under the "Drug Allergies" heading and has food allergies of mushrooms and peanuts under the "Food Allergies" heading. Furthermore, in the illustrative example, the patient's left arm is contraindicated for needle sticks under the "Contraindicated Needle Sticks" heading. This contraindication is also shown graphically on a patient/bed icon via a colored region 486 corresponding to a patient's left arm. For example, region 486 is colored red in some embodiments, although other colors or graphical indicia such as patterns, shading, and so on can be used if desired. Also in the illustrative example, a contraindication relating to patient egress from the patient's left side is indicated in window 482 under the "Contraindicated Other" heading.

Other portions of screen 480 that are substantially similar to portions of the screens described above are indicated by like reference numerals. However, in screen 480, icons or buttons 202, 204, 208, 210 are provided rather than tabs. Also, help button 214 includes a question mark ("?") therein rather than the word "Help." Furthermore, screen 480 includes a patient button or icon 488 that is touched or selected to bring up window 482. An Alarm Silence icon or button 490 is also provided on screen 480 and is selectable to silence any alarms that may occur on bed 10. A vertical scroll bar 492 with a scroll icon 494 is provided on screen 480 to permit a caregiver to scroll to other buttons or icons such as, for example, a charting icon or alarms icon that will appear in the same area on screen 490 as is occupied by buttons 204, 208, 210 and 488 in FIG. 41. As was the case with some prior screens in this disclosure, screen 480 indicates the name of the patient, the patient's doctor, and the patient's assigned nurse, although, in some embodiments, some or all of this information is omitted.

The information regarding contraindications listed in window 482 of screen 480 is communicated to bed from remote computer 176 in some embodiments. This occurs in response to button 488 being selected in some embodiments. In other embodiments, the information is communicated to bed 10 for storage in memory 174 once a particular patient is associated with bed 10. In such embodiments, when button 488 is selected the contraindications information stored in memory 174 is displayed. In still other embodiments, graphical user interface 142 provides for the direct entry of such information via a displayed keyboard, for example, or via drop down menus that list common contraindications in the relevant categories under the headings provided in window 482.

With regard to the contraindications window 482, in some embodiments, the information displayed is obtained from doctor's orders that are entered into and/or stored in remote computer 176 and/or entered using graphical display screen 142. Thus, it is within the scope of this disclosure to receive doctor's orders at the bedside from an EMR or ADT computer 176, for example, and display them locally on display screen 142. Alternatively or additionally, the information displayed on screen 142 includes a patient schedule so that caregivers can see at the bedside what operations and times the patient has in a "Day-At-A-Glance" type of format for calendars. This type of information is useful in determining the contraindications that appear in window 482. For example, after the patient has had spinal surgery, the bed 10 should be configured in a reverse Trendelenburg position with a lowered head section 40. The head section 40 should not be raised after the patient has returned from spinal surgery.

Another example of a contraindicated bed movement is moving the foot and thigh sections 43, 44 of the bed after a patient has had leg surgery. In some instances it may be desirable to keep the foot and thigh sections 43, 44 lowered and in other instances, it may be desirable to keep the thigh section 43 raised with the foot section 44 horizontal, for example. Thus, under the Contradicted Other heading in table 482, examples of messages that appear include "Patient Movement—Keep head section lowered and Keep upper frame in the reverse Trendelenburg position," "Patient Movement—Keep thigh and foot sections flat," "Patient Movement—Keep thigh and foot sections raised," "Do not raise head section," "Do not lower thigh and foot sections" and so forth depending upon the type of patient and/or bed movement to be avoided.

According to this disclosure, when a contraindicated bed movement is attempted contrary to doctor's orders or otherwise contrary to information in a patient's record, display screen 142 displays a warning message such as, for example, "The motion you are trying, [attempted motion listed here], is contraindicated to the following doctor's orders: [doctor order listed here]. Please contact [doctor's name obtained from ADT or EMR system listed here] for more information or to lift the order." Displaying warnings on the graphical user interface 142 if the caregiver attempts to move the bed in a manner that is contraindicated based on information from remote computer 176 improves patient safety and enhances patient outcomes. In some embodiments, display screen 142 has one or more override icons that are selectable to move the bed in the contraindicated manner. The caregiver is required to make the proper override selections on a series of two or more screens or windows in some embodiments.

By providing contraindicated orders on display screen 142, caregivers are aided in remembering the status of each patient and what doctor's orders are currently in effect for the various patients that caregivers are caring for during their shift. This also facilitates in shift hand off of patients from one set of caregivers to another. By warning caregivers about contraindicated bed or patient movements, unwanted bed or patient movements are avoided. This also reduces accidental activation by the patient inadvertently pressing on the outside controls (e.g., the user inputs on the side of the siderail facing away from the patient) because the patient would not be able to see display screen 142 and click through the proper sequence of steps to override the contraindication and proceed with the bed movement.

Figure 42:
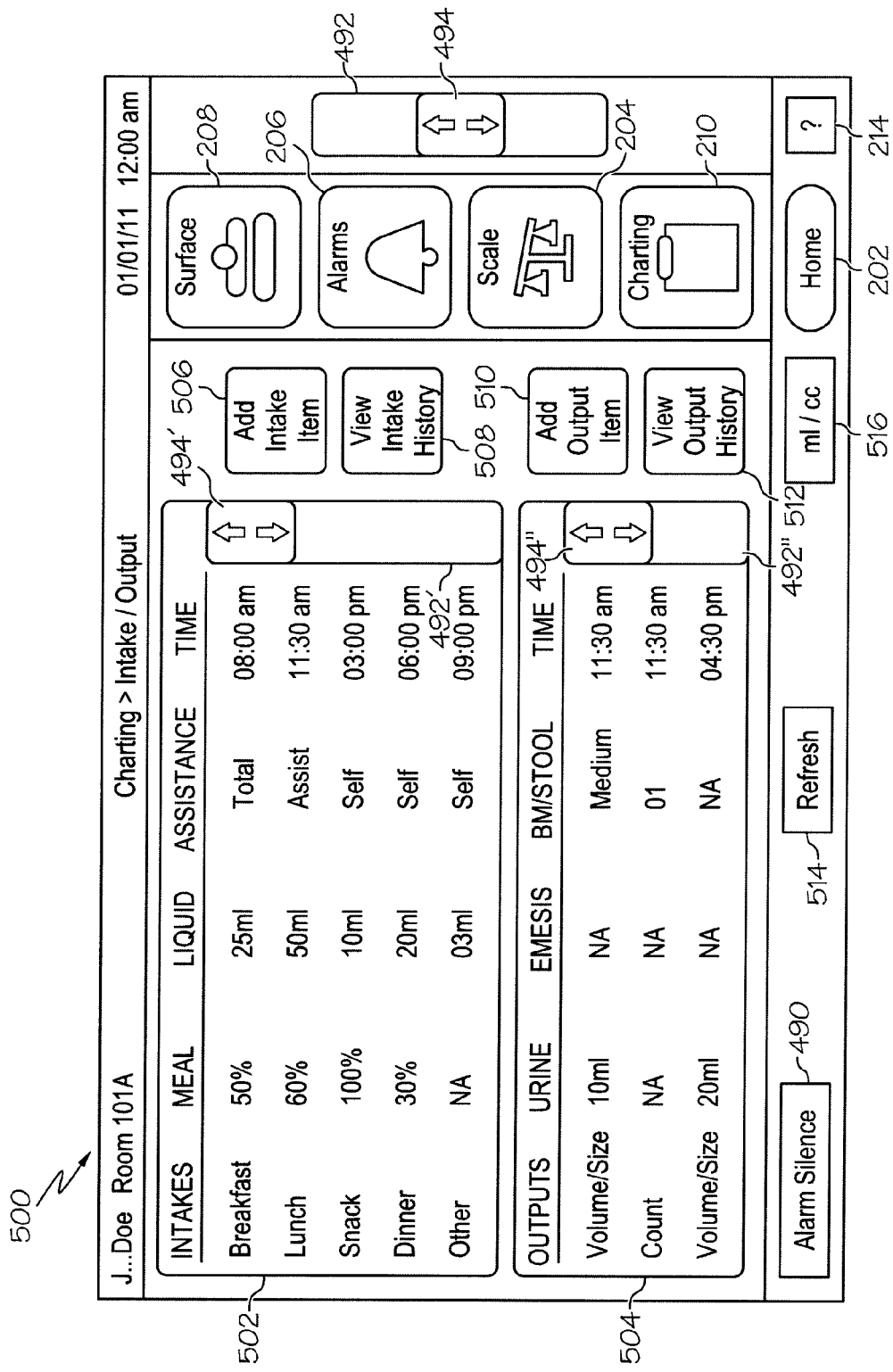
FIG. 42 is a Charting Intake/Output screen showing an Intakes table that appears on the graphical user interface to show information about the food and beverages the patient has consumed at various times and to show an Outputs table having information about the patient's excretions.

Referring now to FIG. 42, a Charting Intake/Output screen 500 includes an Intakes table 502 that appears on the graphical user interface to show information about the food and beverages the patient has consumed at various times and to show an Outputs table 504 having information about the patient's excretions. To navigate to screen 500, Charting button 210 is selected which, in some embodiments, results in a list of various charting options. The charting options are described on buttons in some embodiments and appear on a menu of options in other embodiments. For example, after Charting icon 210 is selected, an Intake/Output button (not shown) and a Vital Signs button (not shown) may appear. Selection of the Intake/Output button results in screen 500 being displayed on the graphical user interface 142. Selection of the Vital Signs button results in screens that are similar or identical to screen 294 of FIG. 13 appearing on the graphical user interface 142. In some embodiments, the user must first enter a PIN on a log in screen as is described above, for example, in connection with screen 226 of FIG. 4.

In the illustrative example, table 502 includes columns with the headings Intakes, Meal, Liquid, Assistance and Time as shown in FIG. 42. The Intakes column includes entries such as Breakfast, Lunch, Snack, Dinner and Other to indicate the type of intake the patient had. The Meal column indicates the percent amount of the intake the patient consumed. In the illustrative example, the patient ate half of his or her breakfast as indicated by the "50%" next to the word Breakfast and the patient ate all of his or her snack as indicated by the "100%" next to the word Snack in table 502. The Liquid column indicates the volume or amount of liquid consumed by the patient in units of milliliters (ml). The Assistance column indicates the amount of help provided by a caregiver to the patient during the meal. In the illustrative example, a caregiver had to feed the entire breakfast to the patient as indicated by the word "Total" in table 502, a caregiver provided some amount of help to the patient during lunch as indicated by the word "Assist" in table 502, and the patient was able to feed himself or herself the remainder of the intakes in table 502 as indicated by the word "Self" shown in each of the remaining rows of table 502. The Time column indicates the time of day that the patient had the particular intake. In some embodiments, a Date column (not shown) is also shown in table 502. A scroll bar 492' and scroll icon 494' are provided on the right hand side of table 502 in the illustrative example for scrolling up and down to other entries of table 502.

Screen 500 further has an Add Intake Item button or icon 506 and a View Intake History button or icon 508 to the right of table 502 in the illustrative example of screen 500. Selection of button 506 permits a caregiver to add another row of information in table 502 via drop down menus or a keyboard or the like. Selection of button 508 provides a caregiver with access to the patient's historical intake information in table 502. The historical intake information corresponds to the patient's intake on one or more preceding days, for example. The intake information is retrieved from remote computer 176 in response to selection of button 508 in some embodiments. Thus, according to this disclosure, intake information entered on table 502 is transmitted by bed 10 to computer 176 for storage in the patient's electronic medical record. The intakes information is transmitted automatically at preset times or periodically to computer 176 from bed 10 in some embodiments. In other embodiments, the intakes information is retrieved from bed 10 by a user at computer 176. Alternatively or additionally, it is within the scope of this disclosure for the intakes information to be stored locally in the memory 174 of bed 10.

In the illustrative example, table 504 includes columns with the headings Outputs, Urine, Emesis, BM/Stool and Time as shown in FIG. 42. The Outputs column indicates the manner in which the output is to be measured, either Volume/Size or Count. Volume/Size and Count correspond to the rows of table 504 in which information is input. The Urine column indicates the amount or volume, in milliliters (ml), when a patient urinates. The Emesis column indicates the amount or volume when a patient vomits. In the illustrative example, the patient has not vomited so Not Applicable ("NA") is indicated in the Emesis column for all outputs. The BM/Stool column indicates a Volume/Size of Medium and a Count of 01 for the patient's bowel movement which, as indicated in the Time column, occurred at 11:30 am. The Time column indicates the time of day that the patient had the particular output. In some embodiments, a Date column (not shown) is also shown in table 504. A scroll bar 492" and scroll icon 494" are provided on the right hand side of table 502 in the illustrative example for scrolling up and down to other entries of table 504.

Screen 500 further has an Add Output Item button or icon 510 and a View Output History button or icon 512 to the right of table 504 in the illustrative example of screen 500. Selection of button 510 permits a caregiver to add another row of information in table 504 via drop down menus or a keyboard or the like. Selection of button 512 provides a caregiver with access to the patient's historical outputs information in table 504. The historical outputs information corresponds to the patient's outputs on one or more preceding days, for example. The outputs information is retrieved from remote computer 176 in response to selection of button 512 in some embodiments. Thus, according to this disclosure, outputs information entered on table 504 is transmitted by bed 10 to computer 176 for storage in the patient's electronic medical record. The outputs information is transmitted automatically at preset times or periodically to computer 176 from bed 10 in some embodiments. In other embodiments, the outputs information is retrieved from bed 10 by a user at computer 176. Alternatively or additionally, it is within the scope of this disclosure for the outputs information to be stored locally in the memory 174 of bed 10.

In some embodiments, the patient's intakes and outputs information is not input at bed 10 but is input at remote computer 176. In such embodiments, a Refresh button or icon 514, an example of which is shown in FIG. 42, is provided on screen 500. Selection of icon 514 results in retrieval by bed 10 of the inputs and outputs information from the remote computer 176. Thus, in some embodiments, the graphical user interface 142 is used to enter the inputs and outputs information for a patient into memory 176 of bed 10 and then, bed 10 pushes that information out to the remote computer 176 for storage in a patient's electronic medical record, for example. In other embodiments, the graphical user interface 142 is used to request or pull the inputs and outputs information from the remote computer 176 for display. Screen includes 500 further includes a ml/cc button or icon 516 for toggling between volume units of milliliters (ml) and cubic centimeters (cc).

Figure 43:
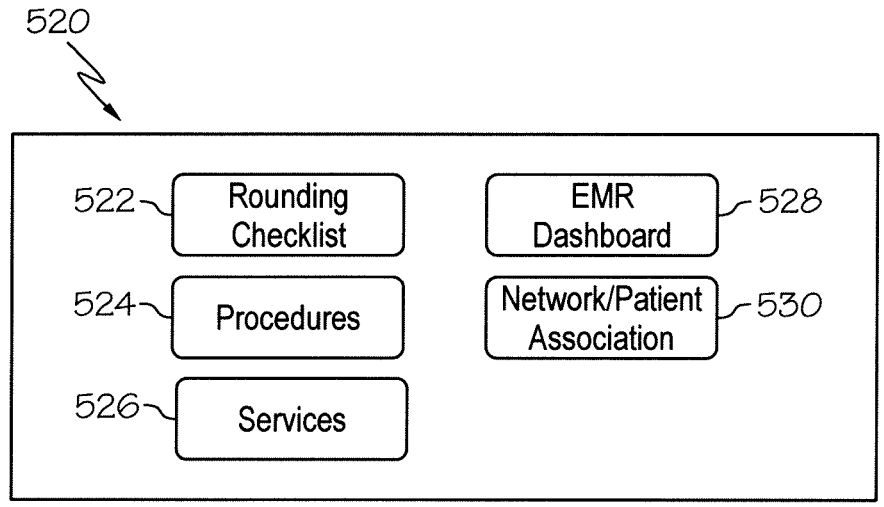
FIG. 43 is a Miscellaneous Functions screen showing icons or buttons that are selected to navigate to the screens of FIGS. 44-48.

Referring now to FIG. 43, a Miscellaneous Functions screen 520 includes icons or buttons that are selected to navigate to the screens of FIGS. 44-48 as will be further discussed below. To navigate to screen 520, in some embodiments, a user scrolls using icon 494 until a Miscellaneous Functions or Other Functions button or icon (not shown) appears on the graphical user interface 142 and then, selection of that button, causes screen 520 to appear. Screen 520 includes a Rounding Checklist button or icon 522, a Procedures icon or button 524, a Services icon or button 526, an EMR Dashboard button or icon 528, and a Network/Patient Association button or icon 530.

Figure 44:
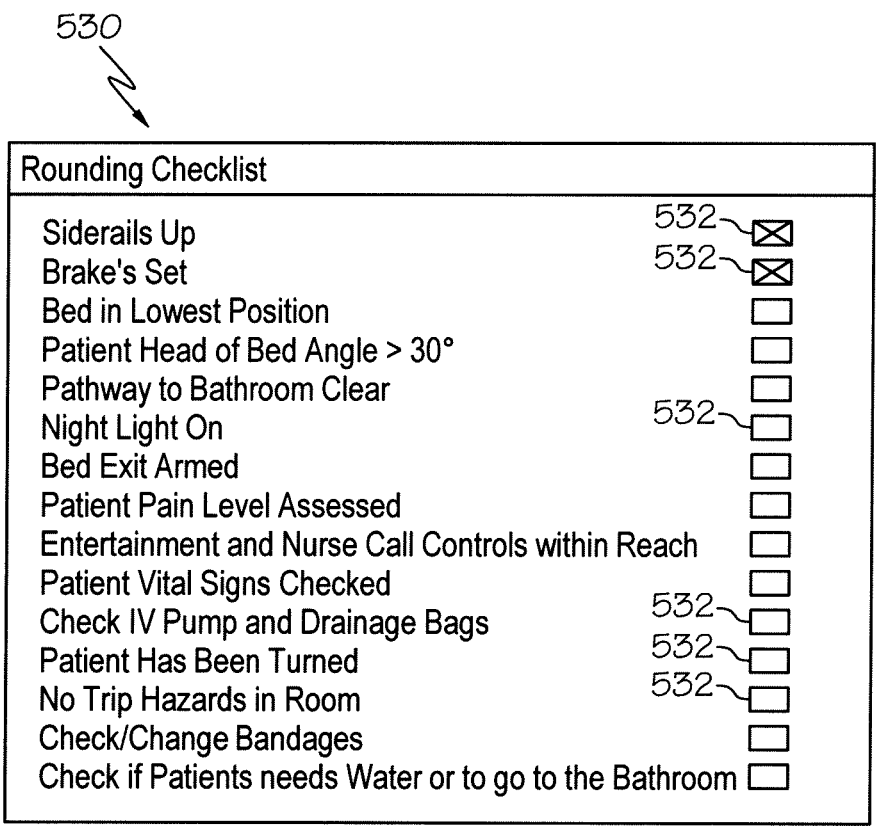
FIG. 44 is a Rounding Checklist screen that appears on the graphical user interface in response to selection of a Rounding Checklist icon of the Miscellaneous Functions screen, the Rounding Checklist screen having a list of tasks or functions that a caregiver should perform in connection with an associated patient.

Selection of button 522 on screen 520 results in a Rounding Checklist screen 530 appearing on the graphical user interface 142 as shown, for example, in FIG. 44. Screen 530 has a list of tasks or functions that a caregiver should perform in connection with an associated patient. In the illustrative example, the rounding checklist include the following tasks and functions: putting siderails up, setting brakes, putting an upper frame of the hospital bed in its lowest position, raising a head section of the hospital bed to a position above 30° of elevation, making sure a pathway to a bathroom is clear, making sure a night light is on, arming a bed exit system, assessing a pain level of a patient, making sure entertainment or nurse call controls are with reach of a patient, checking a patient's vital signs, checking whether IV pump bag or drainage receptacle needs to be replaced or emptied, turning a patient, making sure no trip hazards are present in a room, checking or changing bandages, checking to see if a patient needs drinking water, and checking to see if a patient needs to go to a bathroom.

Check boxes 532 are provided on screen 530 for selection by a caregiver as the tasks or functions are completed. In the illustrative example, the first two tasks at the top of the Rounding Checklist have been completed but the remaining tasks and functions have not. Provision of a rounding check list on the graphical user interface 142 to permit caregivers to check off tasks or items on the check list that have been completed. It will be appreciated that different hospitals have different rounding check lists. Accordingly, it is within the scope of this disclosure for the tasks and functions provided on screen 530 to be custom tailored to a particular healthcare facility. Another example of a task or item on these sorts of check lists includes changing a bed pan or urine bottle.

Figure 45:
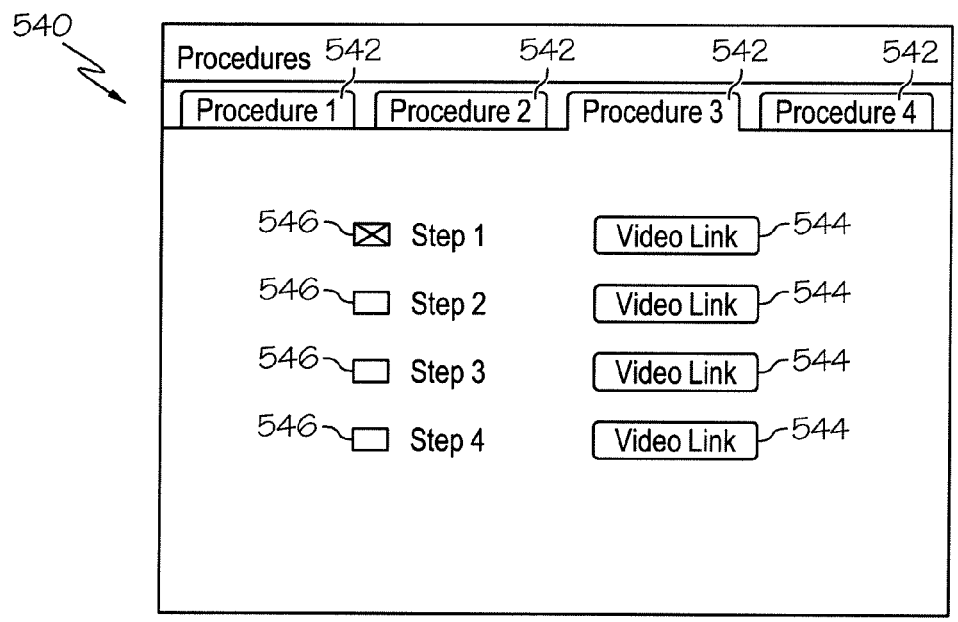
FIG. 45 is a Procedures screen that appears on the graphical user interface in response to selection of a Procedures icon on the Miscellaneous Functions screen, the Procedures screen having a number of Procedures tabs that are selectable to view a list of steps of a procedure and a set of Video Links buttons or icons that are selectable to view a video of an associated step of a procedure.

Selection of button 524 on screen 520 results in a Procedures screen 540 appearing on the graphical user interface 142 as shown, for example, in FIG. 45. Screen 540 has a number of Procedures tabs 542 that are selectable to view a list of steps of an associated procedure. In the illustrative example of screen 540, tabs 542 are depicted generically as being related to Procedure 1, Procedure 2, Procedure 3, and Procedure 4. In a real world implementation, the wording in tabs 542 is edited to be more descriptive of the associated procedure. Such editing is accomplished using a keyboard or other administrative tool such as a lap top or other computer that interfaces with control circuitry 98 of bed 10 via a suitable port or coupler, including wireless coupling devices.

In the illustrative example, Procedure 3 has been selected and a set of Video Links buttons or icons 544 are provided adjacent to each step of the list of steps on screen 540. Selection of a particular icon 544 permits a caregiver to view a video of an associated step of the procedure. The video plays on the graphical user interface 142 and then once the video is finished, screen 540 automatically reappears on the interface 142. In some embodiments, the video played on interface 142 is retrieved from remote computer 176 in response to selection of the corresponding button 544. Thus, it is contemplated by this disclosure that the graphical user interface 142 of bed 10 is used to link to video clips which demonstrate on the graphical user interface 142 at least a portion of a procedure. Screen 540 has check boxes 546 adjacent to each step for selection by a caregiver as the steps of an associated procedure are completed.

Figure 46:
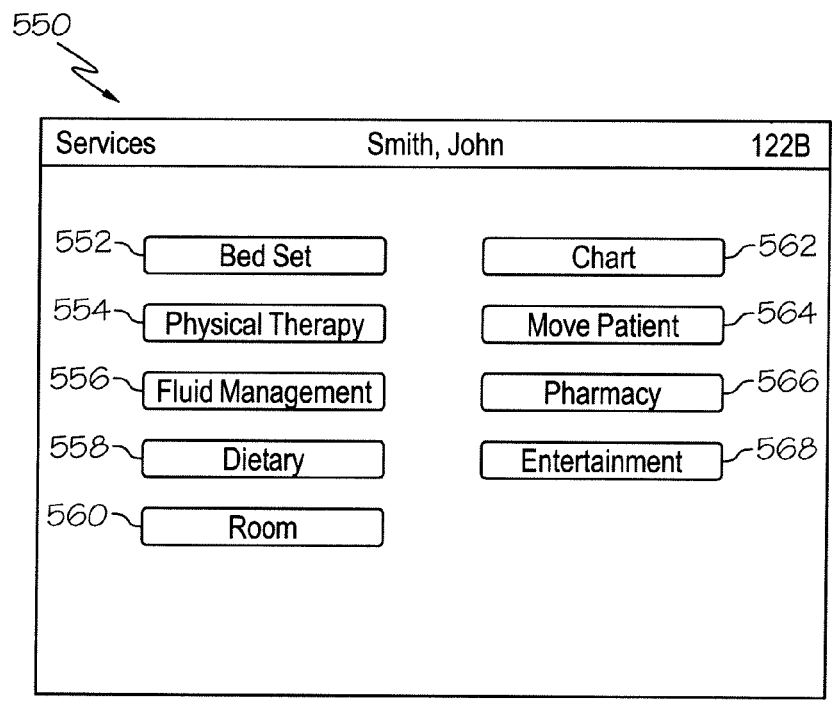
FIG. 46 is a Services screen that appears on the graphical user interface in response to selection of a Services icon on the Miscellaneous Functions screen, the Services screen having a set of Service buttons or icons associated with other services available in the healthcare setting.
Figure 47:
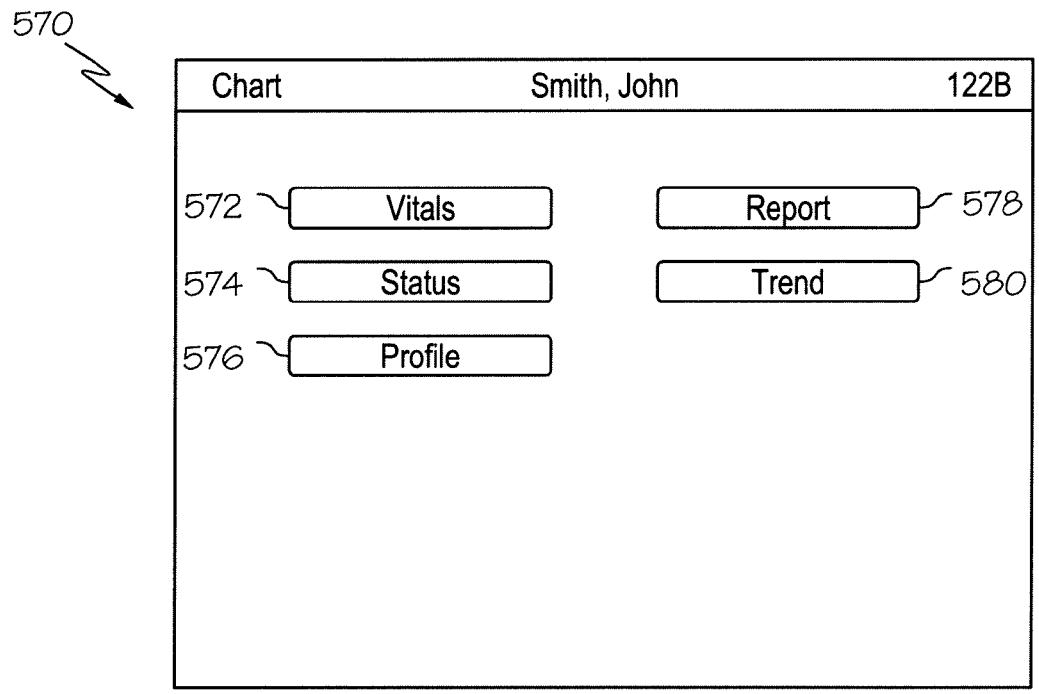
FIG. 47 is a Chart screen that appears on the graphical user interface in response to selection of an EMR Dashboard icon on the Miscellaneous Functions screen, the Chart screen having a set of Chart buttons or icons associated that are selectable to view various data sets available in a patient's electronic medical record.

Selection of button 526 on screen 520 results in a Services screen 550 appearing on the graphical user interface 142 as shown, for example, in FIG. 46. Services screen 550 has a set of service buttons or icons associated with other services available in the healthcare setting. Thus, graphical user interface 142 is capable of providing caregiver and/or patient access to a full range and variety of services at the bed side or point of care. Some of these services are hospital information technology (IT) access related (e.g., EMR, pharmacy, food service, peripheral control, room control), product service and maintenance related, bed function related, and entertainment related (e.g., television control, radio control, web browsing). A patient's healthcare needs relating to charting, dietary and nutrition needs, statistics reporting and/or trending, pharmacy or prescriptions and other activities are able to be carried out using graphical user interface 142 on bed 10 in a HIPAA-compliant, validated use environment in close proximity to the patient and optimized for use case.

In the illustrative example, screen 550 has a Bed Set button or icon 552, a Physical Therapy icon or button 554, a Fluid Management button or icon 556, a Dietary button or icon 558, a Room icon or button 560, a Chart icon or button 562, a Move Patient button or icon 564, a Pharmacy button or icon 566, and an Entertainment button or icon 568 as shown in FIG. 46. Selection of Bed Set button 552 results in a signal being sent from bed 10 to remote computer 176 (e.g., a computer associated with housekeeping scheduling) to indicate that bed 10 is ready to be set up for the next patient. Selection of Physical Therapy button 554 results in information about physical therapy, such as the associated patient's physical therapy schedule, being displayed on the graphical user interface 142. In some embodiments, graphical user interface 142 displays icons or buttons that are used to set up or change a time for one or more of the patient's physical therapy sessions. When button 554 is selected, communication with a remote computer 176 associated with a healthcare facilities' physical therapy department is established.

Selection of Fluid Management button 556 on screen 550 results in information about fluid management being shown on graphical user interface 142. For example, interface 142 has buttons or icons that are selected to indicate that a new IV fluid container is needed and/or that a new Foley bag is needed and/or to indicate that the patient needs more juice or water. Such requests are communicated from bed 10 to remote computer 176 at a master nurse station in some embodiments. Selection of Dietary button 558 results in dietary information being shown on graphical user interface 142. For example, interface 142 has buttons or icons for making food and/or drink choice selections for the patient's upcoming meals or snacks in some embodiments. In some embodiments, the options for such food and/or drink choices are communicated to bed 10 from a remote computer 176 associated with a healthcare facilities' food services department and the food and/or drink choice selections are communicated from the bed 10 to the remote computer 176 of the food services department.

Selection of Room button 560 on screen 550 results in room environmental controls being displayed on graphical user interface 142. Such room controls include buttons or icons that are used to control room lighting and/or room temperature. Selection of Entertainment button 568 results in entertainment controls being displayed on graphical user interface 142. Such entertainment controls include buttons or icons that are used to control a television and/or a radio that are present in the patient's room or included as part of bed 10. The entertainment controls, therefore, include channel selection and volume control icons or buttons.

Selection of Pharmacy icon 566 results in pharmacy information, such as the associated patient's scheduled medicines, being displayed on the graphical user interface 142. In some embodiments, graphical user interface 142 displays icons or buttons that are used to request additional medicine for the patient. When button 566 is selected, communication with remote computer 176 associated with a healthcare facilities' pharmacy department is established. In some embodiments, the pharmacy information is communicated to bed 10 from a remote computer 176 associated with a healthcare facilities' pharmacy department and any pharmacy requests made via graphical user interface 142 of bed 10 are communicated from the bed 10 to the remote computer 176 of the pharmacy department.

Selection of Move Patient button 564 results in a signal being sent from bed 10 to remote computer 176 (e.g., a computer associated with orderly and/or transporter scheduling) to indicate that the associated patient needs to be moved, such as being moved from bed 10 to a stretcher or chair. Selection of Chart button 562 results in a Chart screen 570 being displayed on graphical user interface 142 as shown, for example, in FIG. 47. The Chart screen has a set of Chart buttons or icons that are selectable to view various data sets available in a patient's electronic medical record. In the illustrative example, screen 570 includes a Vitals button or icon 572, a Status icon or button 574, a Profile icon or button 576, a Report button or icon 578, and a Trend icon or button 580.

Selection of Vitals button 572 on screen 550 results in the associated patient's vital signs information being displayed on graphical user interface 142. In some embodiments, the vital signs information is retrieved from the patient's electronic medical record without the ability to edit or enter any of the vital signs information on graphical user interface of bed 10. In other embodiments, selection of button 572 results in a screen substantially similar or identical to screen 294 of FIG. 13 being displayed on interface 142 for entry of the patient's vital signs to the electronic medical record via bed 10.

Selection of Status button 574 on screen 570 results in the associated patient's status information being displayed on graphical user interface 142. In some embodiments, the status information is retrieved from the patient's electronic medical record without the ability to edit or enter any of the status information on graphical user interface of bed 10. In other embodiments, selection of button 574 results in a screen being displayed on interface 142 for entry of the patient's status information into the electronic medical record via bed 10. Selection of Profile button 576 on screen 570 results in the associated patient's profile information being displayed on graphical user interface 142. In some embodiments, the profile information is retrieved from the patient's electronic medical record without the ability to edit or enter any of the profile information on graphical user interface of bed 10. In other embodiments, selection of button 576 results in a screen being displayed on interface 142 for entry of the patient's profile information into the electronic medical record via bed 10.

Selection of Report icon 578 results in the associated patient's medical report information being displayed on graphical user interface 142. In some embodiments, the medical report information is retrieved from the patient's electronic medical record without the ability to edit or enter any of the report information on graphical user interface of bed 10. In other embodiments, selection of button 578 results in a screen being displayed on interface 142 for entry of the patient's medical report information into the electronic medical record via bed 10. Selection of Trend icon 580 results in the associated patient's historical trending information being displayed on graphical user interface 142. Screen 330 of FIG. 21 is an example of the type of trending information that is displayed on interface 142 in response to selection of icon 580.

Figure 48:
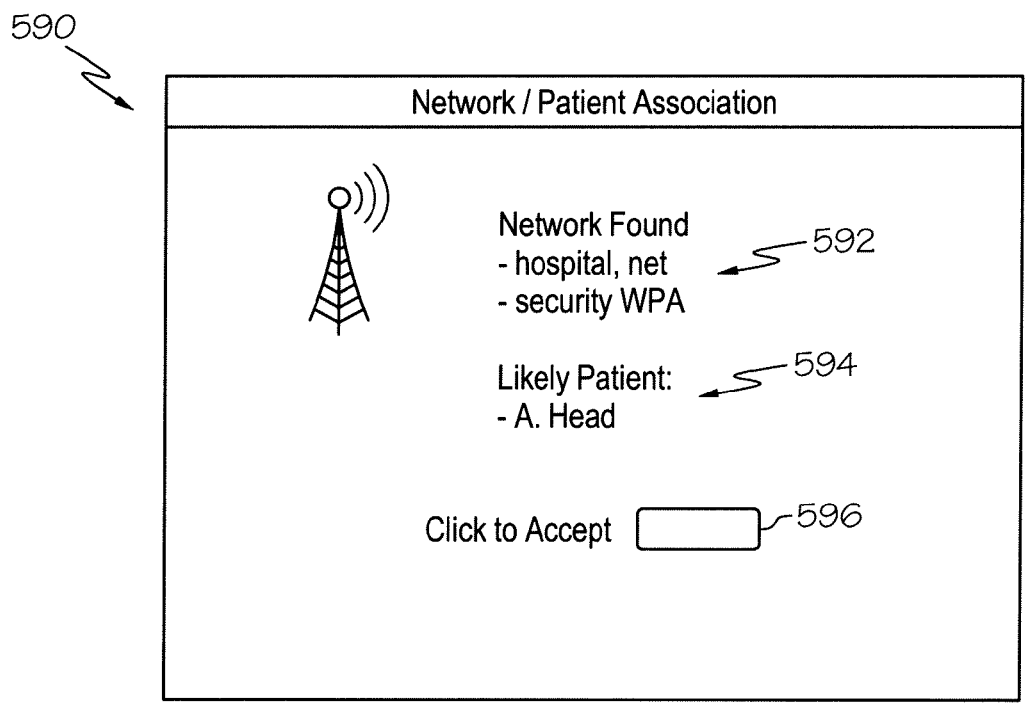
FIG. 48 is a Network/Patient Association screen that appears on the graphical user interface in response to selection of a Network/Patient Association icon on the Miscellaneous function screen, the Network/Patient Association screen having a first block of text providing information about network connectivity and a second block of text providing information about a patient to be associated with the corresponding bed.

Referring now to FIG. 48, a Network/Patient Association screen 590 that appears on the graphical user interface in response to selection of a Network/Patient Association icon 530 on the Miscellaneous function screen 520 is shown. Screen 590 has a first block of text 592 providing information about network connectivity and a second block of text 594 providing information about a likely patient to be associated with the corresponding bed 10. If the bed 10 is able to communicate with more than one network, then information about the multiple available networks is displayed in block of text 592 and the user then selects which of the available networks the bed 10 should use for communications. Furthermore, block of text 594 may have a list of patients that possibly may be associated with the bed 10, in which case, the user selects the appropriate patient for association with bed 10 from the list of patients. According to this disclosure, the list of likely patients is established via programmed logic based on patient gender, weight, and so forth. For example, if a weigh scale system of bed 10 senses that the patient weighs 250 lbs., then a list of patients having similar such weight (within a tolerance range such as 10 or 20%, for example) may be displayed in block of text 594. Other biometric data such a height, fingerprint, retinal scan, for example, may be used in some embodiments to filter the list of possible patients for display in block of text 594. In such embodiment, bed 10 includes the appropriate sensors (e.g., finger print reader or retinal scanner) for sensing the patient's biometric information. An Accept button or icon 596 is provided on the graphical user interface 142 for selection by a caregiver to accept association of the patient with the hospital bed 10.

Additional concepts and features within the scope of this disclosure include the following:

Provision of a look-up table of patient names on the graphical user interface 142 to permit the caregiver to select the patient assigned to bed 10 from a list of patients appearing on the look-up table or to confirm at the bedside that the patient-to-bed association made elsewhere, such as at a remote computer, is correct. The menu of patients is pulled from an ADT system in some embodiments. The menu is filterable or filtered in some embodiments. For example, a male/female selection and/or a race selection can be made on interface 142 and then only male or female names of the selected race, depending upon the selections, are listed in the menu. Provision of additional look-up tables to set or confirm doctor-to-patient, caregiver-to-patient, and bed-to-room associations. If the bed communicates wirelessly, the menu of possible room selections to set the bed-to-room association is filtered based on signal strength sensed by one or more wireless receivers, either on the bed or off the bed. In some embodiments, the caregiver simply types the room number on the graphical user interface of bed 10.

Messages of the graphical user interface 142 are provided at preset times in some embodiments to prompt the caregiver to confirm or edit patient-to-bed, caregiver-to-bed, bed-to-room, and doctor-to-patient associations. The preset times may correspond to shift changes, for example. Events may also trigger the caregiver to confirm or edit the various associations. For example, if the bed becomes unplugged and then is plugged back in after a threshold amount of time, which would occur when the bed is moved, then the caregiver is prompted to confirm or edit the associations on graphical user interface 142. If the bed is unplugged for a small amount of time, such as 15 seconds or 30 seconds, for example, then re-verification of the associations is skipped in some embodiments.

In some embodiments, bed 10 receives various patient scores, such as the Braden score, a falls risk scores, a modified early warning score (MEWS), etc. and displays the scores on interface 142. In some embodiments, bed 10 receives the patient's vital signs information from the EMR system 176 and displays the data on interface 142. In some embodiments, features and functions of bed 10 are configured in a certain way based on the one or more scores and/or the vital signs data received from the EMR system 176.

Provision of a Standard of Care (SoC) check list on the graphical user interface 142. For example, if the patient is a falls risk, then the patient should be wearing red footies, the patient should have a red blanket, a star should be placed on the patient's door, etc. Each of the items in the SoC can be listed on interface 142 for manual verification by the caregiver. In some embodiments, the SoC changes based on an event. For example, if bed receives data from a remote computer or an in-room device or via manual entry that a patient has started a morphine drip, the SoC protocol switches from low falls risk to high falls risk and the corresponding SoC check list is displayed on the graphical user interface 142.

Provision of a skin assessment tool, such as a series of questions to answer or selections to make, on the graphical user interface 142.

Emulating or replicating EMR computer screens on the graphical user interface 142 of the bed 10 for entry of data into the patient's EMR at the bed in the same way as is done at a remote EMR computer.

Displaying a patient's lab results on the graphical user interface 142.

Importing the patient's height and/or weight from the EMR system 176, or entering the patient's height on the graphical user interface 142, having the bed 10 calculate the patient's body mass index (BMI), and displaying the BMI on the graphical user interface 142.

Linking to a medication delivery system, such as the Pixis system, and displaying information about the patient's medication on the graphical user interface 142.

Use of a locating and tracking system in conjunction with the rounding check list to monitor caregiver's compliance with completing items on the check list prior to exiting the patient's room.

Provision of a graphical user interface, similar to interface 142, but separate from bed 10 that has the same screens and functionality as discussed herein. This separate user interface is wall mounted in some embodiments and is included as part of a graphical audio station of a nurse call system in some embodiments.

Although certain illustrative embodiments have been described in detail above, many embodiments, variations and modifications are possible that are still within the scope and spirit of this disclosure as described herein and as defined in the following claims.

The invention claimed is:

1. A hospital bed for use in a healthcare facility having an electronic medical record (EMR) system that maintains, for a plurality of patients, an electronic medical record (EMR) remote from the hospital bed for each patient, the hospital bed comprising:
  a base frame;
  an upper frame assembly including a patient support deck having a plurality of movable deck sections including a head section, the movable deck sections being movable to change a position at which a patient is supported by the patient support deck;
  a plurality of motors to move the movable deck sections;
  a lift system operable to raise, lower, and tilt the upper frame assembly relative to the base frame;
  a set of barriers coupled to the upper frame assembly, at least some of the barriers being movable relative to the upper frame assembly between a raised position and a lowered position;
  control circuitry and local memory carried by at least one of the base frame and the upper frame assembly,
  wherein the control circuitry is electrically coupled to the motors and an angle sensor to measure the angle of the head section; and
  a graphical user interface (GUI) coupled to the control circuitry, the control circuitry configured to command the GUI to display selectable tabs including a Tools tab and a Charting tab,
  wherein, in response to selection of the Tools tab at the GUI, the control circuitry is configured to command the GUI to display a switch that is selectable to enable or disable an EMR Autosend feature such that when enabled the control circuitry stores charted data in the local memory and then initiates the charting of the data to the EMR system and when disabled the control circuitry stores charted data in the local memory and then does not initiate the charting of the data to the EMR system,
  wherein, in response to selection of the Charting tab and additional user inputs received at the GUI, the control circuitry is configured to command the GUI (i) to display a bed status screen having a first charting icon that is selectable to chart the current bed status data, (ii) to display a patient information screen having a second charting icon that is selectable to chart patient vital signs data, and (iii) to display an activity screen having a third charting icon that is selectable to chart data about a position or change in position of the patient relative to the patient support deck, and
  wherein, in response to the data being charted, the GUI displays the data just charted and, when the Autosend feature is enabled, the date and time at which the data was charted to the EMR system, and when the Autosend feature is disabled, data indicating that a date and time is not available.

2. The hospital bed of claim 1, wherein, in response to the data being charted, the GUI displays the data just charted and at least one icon that is touched sequentially to access, in reverse chronological order, respective historical data that has been charted to the patient's EMR previously.

3. The hospital bed of claim 1, wherein the control circuitry further commands the GUI to display a patient information icon on the Charting tab that is selectable to display the patient information screen that the caregiver uses to manually enter vital signs data of the patient as read by the caregiver from at least one other device.

4. The hospital bed of claim 3, further comprising at least one sensor supported by the upper frame assembly and operable to output a signal representative of first vital sign data of the patient supported by the patient support deck.

5. The hospital bed of claim 4, wherein the first vital sign data is auto-populated on the patient information screen, the manually entered vital signs data being subsequently charted from the hospital bed to the patient's EMR along with the first vital sign data.

6. The hospital bed of claim 1, wherein the control circuitry requires verification of the caregiver's identity prior to sending data to the EMR system for charting in the patient's EMR.

7. The hospital bed of claim 6, wherein the control circuitry commands the GUI to display a screen requiring the caregiver to enter a personal identification number (PIN) in response to at least one input being used on the GUI and entry of the PIN by the caregiver provides the verification required by the control circuitry prior to sending data to the EMR system.

8. The hospital bed of claim 6, further comprising a card reader coupled to the control circuitry, the control circuitry requiring the caregiver to present to the card reader an identification (ID) card in response to use of at least one input being of the GUI, and the card reader presented with the ID card by the caregiver providing the verification required by the control circuitry prior to sending data to the EMR system.

9. The hospital bed of claim 6, further comprising a wireless tag reader coupled to the control circuitry, the control circuitry determining whether a wireless tag assigned to the caregiver is in communication with the wireless tag reader in response to at least one input being used on the GUI, and communication between the wireless tag and the wireless tag reader provides the verification required by the control circuitry prior to sending data to the EMR system.

10. The hospital bed of claim 1, wherein the bed status data displayed on the GUI in response to selection of the first charting icon includes one or more the following: an angle of the head section of the patient support structure, whether or not caster brakes of the patient support structure are set, whether or not the upper frame assembly is in a low position relative to the base frame, whether a patient position monitoring system of the hospital bed is armed, and whether a head of bed monitoring system of the hospital bed is armed.

11. The hospital bed of claim 10, wherein, after selection of the first charting icon, when the Autosend feature is enabled, the GUI displays a confirmation screen which the caregiver uses to confirm that the current bed status data is to be charted to the patient's EMR.

12. The hospital bed of claim 10, wherein the GUI displays a graph button that is selected to graphically show on the GUI a history of bed status data that has been charted to the patient's EMR previously.

13. The hospital bed of claim 1, wherein the patient's vital signs data includes one or more of the following: heart rate, respiration rate, blood pressure, pulse oximetry, and temperature.

14. The hospital bed of claim 13, wherein, after selection of the second charting icon, when the Autosend feature is enabled, the GUI displays a confirmation screen which the caregiver uses to confirm that the patient's vital signs data is to be charted to the patient's EMR.

15. The hospital bed of claim 13, wherein the GUI displays a graph button that is selected to graphically show on the GUI a history of the patient's vital signs data that has been charted to the patient's EMR previously.

16. The hospital bed of claim 1, wherein the GUI displays a weigh patient button that is selected to command the control circuitry to weigh the patient supported on the patient support structure and to display a fourth charting icon that the caregiver has the option of selecting to initiate the charting of the patient's weight to the patient's EMR.

17. The hospital bed of claim 1, wherein data about the position or change in position of the patient relative to the patient support deck includes at least one or more of the following:
whether the patient is lying on their back, whether the patient is lying on their right side,
whether the patient is lying on their left side, whether the patient has moved out of the hospital bed and is sitting on a chair, and whether the patient support deck has been moved to a chair position to support the patient in a sitting position.

18. The hospital bed of claim 17, wherein, after selection of the third charting icon, when the Autosend feature is enabled, the GUI displays a confirmation screen which the caregiver uses to confirm that data about the position or change in position of the patient relative to the patient support deck is to be charted to the patient's EMR.

19. The hospital bed of claim 17, wherein the GUI displays a graph button that is selected to graphically show on the GUI a history of the data about the position or change in position of the patient relative to the patient support deck the that has been charted to the patient's EMR previously.

20. The hospital bed of claim 1, wherein the control circuitry commands the GUI to display at least one or more of the following: a list of a patient's drug allergies, a list of a patient's food allergies, a contraindication relating to a needle stick, a contraindication relating to patient egress, a contraindication relating to patient movement, a contraindication relating to bed movement, and a warning message that an attempted bed movement is contrary to a doctor's orders.

21. The hospital bed of claim 1, wherein the control circuitry commands the GUI to display data regarding the patient's intakes and outputs.

22. The hospital bed of claim 21, wherein the data regarding the patient's intakes includes at least one or more of the following: a percent of the amount of food eaten by the patient during a meal or snack, a volume of liquid consumed by a the patient, an amount of eating or drinking assistance provided by a caregiver to the patient, and a time at which the patient ate or drank.

23. The hospital bed of claim 21, wherein the data regarding the patient's outputs includes at least one or more of the following: an amount of urine output by the patient, an amount of stool output by the patient, an amount of emesis output by the patient, and a time at which the patient output occurred.

24. The hospital bed of claim 1, wherein the control circuitry commands the GUI to display a rounding checklist.

25. The hospital bed of claim 24, wherein the rounding checklist includes a list of tasks or functions to be performed by a caregiver.

26. The hospital bed of claim 25, wherein the list of tasks or functions includes at least one or more of the following: putting siderails up, setting brakes, putting an upper frame of the hospital bed in its lowest position, raising a head section of the hospital bed to a position above 30° of elevation, making sure a pathway to a bathroom is clear, making sure a night light is on, arming a bed exit system, assessing a pain level of a patient, making sure entertainment or nurse call controls are within reach of the patient, checking a patient's vital signs, checking whether IV pump bag or drainage receptacle needs to be replaced or emptied, turning a patient, making sure no trip hazards are present in a room, checking or changing bandages, checking to see if the patient needs drinking water, and checking to see if the patient needs to go to a bathroom.

27. The hospital bed of claim 1, wherein the control circuitry commands the GUI to display a list of procedures.

28. The hospital bed of claim 27, wherein each procedure of the list of procedures includes a list of steps of the associated procedure.

29. The hospital bed of claim 1, wherein the GUI is operable to link to video clips which demonstrate on the GUI at least a portion of a procedure.

30. The hospital bed of claim 1, wherein the GUI is used to show at least one of data about network connectivity and data about a patient that is likely to be associated with the hospital bed.

31. The hospital bed of claim 30, wherein a button or icon is provided on the GUI for selection by a caregiver to accept association of the patient with the hospital bed.

* * * * *